United States Patent
Adachi et al.

(10) Patent No.: US 10,381,573 B2
(45) Date of Patent: Aug. 13, 2019

(54) LIGHT-EMITTING MATERIAL, ORGANIC LIGHT-EMITTING DEVICE, AND COMPOUND

(71) Applicant: KYULUX, INC., Fukuoka-shi, Fukuoka (JP)

(72) Inventors: Chihaya Adachi, Fukuoka (JP); Takuma Yasuda, Fukuoka (JP); Ryosuke Kondo, Fukuoka (JP); Masaki Numata, Fukuoka (JP); Jun-Yun Kim, Fukuoka (JP); Inseob Park, Fukuoka (JP)

(73) Assignee: KYULUX, INC., Fukuoka-Shi, Fukuoka (JP)

( * ) Notice: Subject to any disclaimer, the term of this patent is extended or adjusted under 35 U.S.C. 154(b) by 0 days.

(21) Appl. No.: 15/039,536

(22) PCT Filed: Nov. 27, 2014

(86) PCT No.: PCT/JP2014/081321
§ 371 (c)(1),
(2) Date: May 26, 2016

(87) PCT Pub. No.: WO2015/080183
PCT Pub. Date: Jun. 4, 2015

(65) Prior Publication Data
US 2016/0380205 A1     Dec. 29, 2016

(30) Foreign Application Priority Data

Nov. 28, 2013  (JP) ................. 2013-246520
May 30, 2014   (JP) ................. 2014-112563

(51) Int. Cl.
*H01L 51/00* (2006.01)
*C07C 255/58* (2006.01)
(Continued)

(52) U.S. Cl.
CPC ........ *H01L 51/0071* (2013.01); *C07C 255/58* (2013.01); *C07D 209/86* (2013.01);
(Continued)

(58) Field of Classification Search
None
See application file for complete search history.

(56) References Cited

U.S. PATENT DOCUMENTS

2007/0202358 A1*  8/2007  Sano ............... H01L 51/005
                                                        428/690
2013/0228752 A1   9/2013  Shin
2016/0301015 A1* 10/2016  Zheng ................. C09K 11/06

FOREIGN PATENT DOCUMENTS

EP    2039737    3/2009
JP    06222593   8/1994
(Continued)

OTHER PUBLICATIONS

Liu et al. (J. Phys. Org. Chem. 2007, 20, p. 600).*
(Continued)

*Primary Examiner* — Jay Yang
(74) *Attorney, Agent, or Firm* — Browdy and Neimark, PLLC

(57) ABSTRACT

A compound represented by the general formula (1) is useful as a light-emitting material. In the general formula (1), from 0 to 1 of $R^3$ to $R^5$ represents a cyano group, from 1 to 5 of $R^1$ to $R^5$ represent a group represented by the general formula (2) etc., and the balance of $R^1$ to $R^6$ represent a hydrogen atom or a substituent other than above. $R^{11}$ to $R^{20}$ represent a hydrogen atom or a substituent, $L^{12}$ represents a substituted or unsubstituted arylene group or a substituted or unsubstituted heteroarylene group.

(Continued)

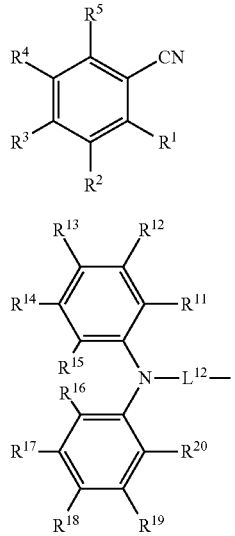

18 Claims, 33 Drawing Sheets

(51) Int. Cl.
  C07D 265/38 (2006.01)
  C07D 209/86 (2006.01)
  C09K 11/06 (2006.01)
  C07D 219/14 (2006.01)
  H01L 51/50 (2006.01)
  H01L 51/52 (2006.01)

(52) U.S. Cl.
  CPC ......... *C07D 219/14* (2013.01); *C07D 265/38* (2013.01); *C09K 11/06* (2013.01); *H01L 51/0059* (2013.01); *H01L 51/0061* (2013.01); *H01L 51/0072* (2013.01); *C09K 2211/1007* (2013.01); *C09K 2211/1029* (2013.01); *C09K 2211/1033* (2013.01); *H01L 51/0067* (2013.01); *H01L 51/0073* (2013.01); *H01L 51/0074* (2013.01); *H01L 51/5012* (2013.01); *H01L 51/5016* (2013.01); *H01L 51/5028* (2013.01); *H01L 51/5056* (2013.01); *H01L 51/5072* (2013.01); *H01L 51/5088* (2013.01); *H01L 51/5092* (2013.01); *H01L 51/5096* (2013.01); *H01L 51/5206* (2013.01); *H01L 51/5221* (2013.01); *H01L 2251/5376* (2013.01)

(56) References Cited

FOREIGN PATENT DOCUMENTS

| | | | |
|---|---|---|---|
| JP | 2003-142263 A | | 5/2003 |
| JP | 2003142263 A | * | 5/2003 |
| JP | 2004273128 | | 9/2004 |
| JP | 2007266598 A | | 10/2007 |
| JP | 2007318101 | | 12/2007 |
| JP | 2011173973 | | 9/2011 |
| JP | 2011176258 | | 9/2011 |
| JP | 2014172835 | | 9/2014 |
| NO | 2012/078005 A2 | | 6/2012 |
| WO | 2013/154064 | | 10/2013 |
| WO | 2014/208698 | | 12/2014 |
| WO | 2015/060352 | | 4/2015 |
| WO | WO-2015/175678 A1 | * | 11/2015 |

OTHER PUBLICATIONS

Cheng et al. (Tetrahedron 2011, 67, p. 734).*
Cheng, et al., A New Approach to Design Ratiometric Fluorescent Probe for Mercury(II) Based on the Hg2+-Promoted Deprotection of Thioacetals, Applied Materials & Interfaces, 2010, vol. 2, No. 4, pp. 1066-1072.
Mi, et al., Impact of substitution on the reorganization energy of bis-triarylamine derivatives, Journal of Molecular Structure: Theochem, 2010, vol. 940, pp. 1-5.
International Preliminary Report on Patentability for International Application No. PCT/JP2014/081321 dated Jun. 2, 2016 in English and Japanese.
International Search Report for International Application No. PCT/JP2014/081321 dated Feb. 17, 2015.
First Office Action in corresponding Chinese Application No. 201480065045.5, dated Apr. 12, 2017 with English translation.
CA Registry No. 1437781-99-1, STN Search (Mar. 22, 2017).
European search report dated Oct. 4, 2017 from corresponding European application No. 14866266.1.
Office Action dated Jan. 9, 2018 issued in the corresponding Chinese patent application No. 201480065045.5 with its English Machine Translation.
Office Action dated Jan. 11, 2018 issued in the corresponding Taiwanese patent application No. 103140879 with its English Translation.
Office Action in Chinese patent application No. 201480065045.5 with its English Machine Translation dated Jul. 16, 2018.
Japanese Office Action dated Aug. 28, 2018 issued in the corresponding Japanese patent application No. 2015-550976 with its English Machine Translation.
Office Action dated Dec. 21, 2018 issued in the corresponding European patent application No. 14866266.1.

* cited by examiner

LIGHT-EMITTING MATERIAL, ORGANIC LIGHT-EMITTING DEVICE, AND COMPOUND

TECHNICAL FIELD

The present invention relates to a compound that is useful as a light-emitting material, and an organic light-emitting device using the same.

BACKGROUND ART

An organic light-emitting device, such as an organic electroluminescent device (organic EL device), has been actively studied for enhancing the light emission efficiency thereof. In particular, various studies for enhancing the light-emitting efficiency have been made by newly developing and combining an electron transporting material, a hole transporting material, a light-emitting material and the like constituting an organic electroluminescent device. There are studies relating to an organic electroluminescent device utilizing a compound having a structure containing a donor, such as a carbazolyl group and a carbazolylphenyl group, bonded to an acceptor, such as a benzene ring substituted by a cyano group or the like.

Patent Literature 1 describes an example using a compound represented by the following general formula as a host material in a light-emitting layer present between a pair of electrodes constituting an organic electroluminescent device. In the following general formula, A represents an N-carbazolyl group or an atomic group that is necessary for forming carbazole along with the benzene ring, $R_1$ and $R_2$ each represent a substituent, and $R_3$ and $R_4$ each represent a hydrogen atom or a substituent, and a cyano group is exemplified as an example of the substituent capable of being represented by $R_1$ to $R_4$. However, Patent Literature 1 does not describe the light emission characteristics of the compound represented by the general formula.

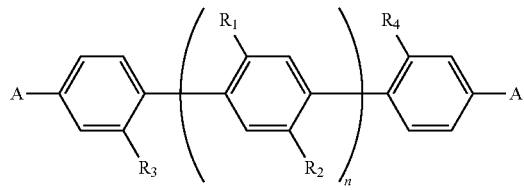

Patent Literature 2 describes an example using a compound represented by the following general formula as a host material of a light-emitting layer of an organic electroluminescent device. In the general formula, $R_1$ to $R_8$ each represent a hydrogen atom, an alkyl group, an aryl group, a heteroaryl group, or an electron withdrawing group, in which the electron withdrawing group is a cyano group, a nitro group, a perfluoroalkyl group, or a halogen atom, and $R_{1a}$ and $R_{1b}$ each represent an alkyl group, an alkoxy group, an aryl group, a heteroaryl group, a cyano group, a nitro group, a halogen atom, or an amino group. However, Patent Literature 2 does not describe the light emission characteristics of the compound represented by the general formula.

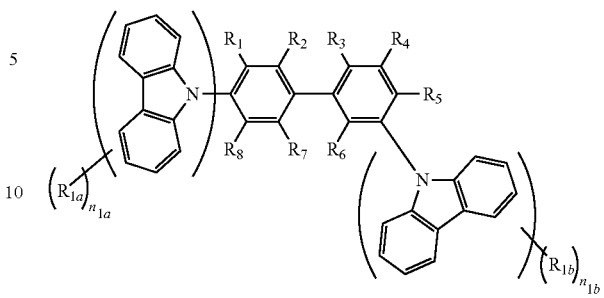

CITATION LIST

Patent Literatures

Patent Literature 1: JP-A-2004-273128
Patent Literature 2: JP-A-2011-176258

SUMMARY OF INVENTION

Technical Problem

As described above, Patent Literatures 1 and 2 describe that a compound having a structure containing a benzene ring substituted by a cyano group or the like, having bonded thereto a carbazolyl group or the like is useful as a host material of a light-emitting layer of an organic electroluminescent device, and the like. However, there has been no investigation as to whether or not the compounds described in Patent Literatures 1 and 2 are capable of functioning as a light-emitting material. A light-emitting material is different from a host material in demanded properties and functions, and therefore the usefulness of the compounds represented by the general formulae of Patent Literatures 1 and 2 as a light-emitting material is unknown. Furthermore, Patent Literatures 1 and 2 do not describe a compound having a structure containing a benzene ring substituted by two or more cyano groups, and the usefulness of the compound as a light-emitting material cannot be expected.

Under the circumstances, the present inventors have made various investigations on a group of compounds having a structure containing a benzene ring having bonded thereto a carbazolyl group or the like while changing the kind of the substituent and the substitution number, and thus have been firstly found that a group of compounds having a structure containing a benzene ring substituted by two or more cyano groups has usefulness as a light-emitting material. Furthermore, the inventors have made earnest investigations for providing a general formula of the compounds useful as a light-emitting material and generalizing the structure of an organic light-emitting material having a high light emission efficiency.

Solution to Problem

As a result of the earnest investigations performed, the inventors have found that among the compounds having a structure containing a benzene ring substituted by two or more cyano groups, having bonded thereto a carbazolyl group or the like, compounds having a particular structure have excellent properties as a light-emitting material. The inventors also have found that the group of compounds includes compounds that are useful as a delayed fluorescent material, and have clarified that an organic light-emitting device having a high light emission efficiency can be provided inexpensively. Based on the knowledge, the inventors have provided the following inventions as measures for solving the problems.

(1) A light-emitting material containing a compound represented by the following general formula (1):

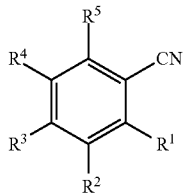

General Formula (1)

wherein in the general formula (1), from 0 to 1 of $R^1$ to $R^5$ represents a cyano group, from 1 to 5 of $R^1$ to $R^5$ each represent a group represented by the following general formula (2) or the following general formula (7), and the balance of $R^1$ to $R^5$ each represent a hydrogen atom or a substituent other than above:

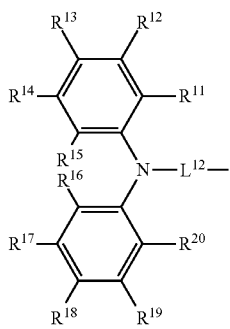

General Formula (2)

wherein in the general formula (2), $R^1$ to $R^{20}$ each independently represent a hydrogen atom or a substituent, provided that $R^{11}$ and $R^{12}$, $R^{12}$ and $R^{13}$, $R^{13}$ and $R^{14}$, $R^{14}$ and $R^{15}$, $R^{15}$ and $R^{16}$, $R^{16}$ and $R^{17}$, $R^{17}$ and $R^{18}$, $R^{18}$ and $R^{19}$, and $R^{19}$ and $R^{20}$ each may be bonded to each other to form a cyclic structure; and $L^{12}$ represents a substituted or unsubstituted arylene group or a substituted or unsubstituted heteroarylene group,

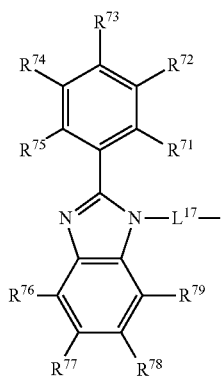

General Formula (7)

wherein in the general formula (7), $R^{71}$ to $R^{79}$ each independently represent a hydrogen atom or a substituent, provided that $R^{71}$ and $R^{72}$, $R^{72}$ and $R^{73}$, $R^{73}$ and $R^{74}$, $R^{74}$ and $R^{75}$, $R^{76}$ and $R^{77}$, $R^{77}$ and $R^{78}$, $R^{78}$ and $R^{79}$ each may be bonded to each other to form a cyclic structure; and $L^7$ represents a substituted or unsubstituted arylene group or a substituted or unsubstituted heteroarylene group.

(2) The light-emitting material according to the item (1), wherein the group represented by the general formula (2) is a group represented by any one of the following general formulae (3) to (6) and (8):

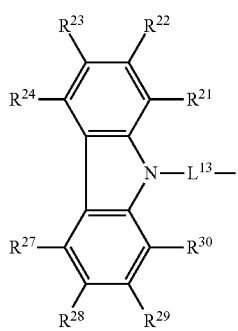

General Formula (3)

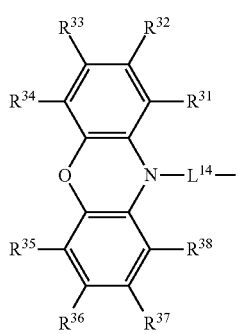

General Formula (4)

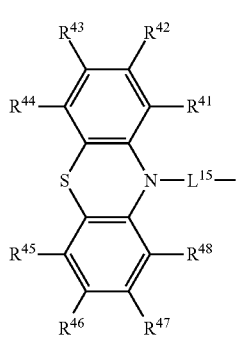

General Formula (5)

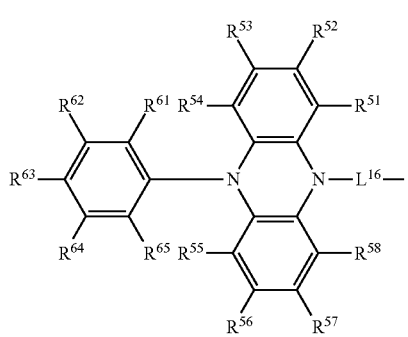

General Formula (6)

-continued

General Formula (8)

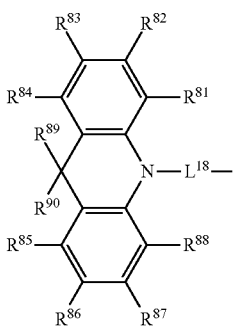

wherein in the general formulae (3) to (6) and (8), $R^{21}$ to $R^{24}$, $R^{27}$ to $R^{38}$, $R^{41}$ to $R^{48}$, $R^{51}$ to $R^{58}$, $R^{61}$ to $R^{65}$, and $R^{81}$ to $R^{90}$ each independently represent a hydrogen atom or a substituent, provided that $R^{21}$ and $R^{22}$, $R^{22}$ and $R^{23}$, $R^{23}$ and $R^{24}$, $R^{27}$ and $R^{28}$, $R^{28}$ and $R^{29}$, $R^{29}$ and $R^{30}$, $R^{31}$ and $R^{32}$, $R^{32}$ and $R^{33}$, $R^{33}$ and $R^{34}$, $R^{35}$ and $R^{36}$, $R^{36}$ and $R^{37}$, $R^{37}$ and $R^{38}$, $R^{41}$ and $R^{42}$, $R^{42}$ and $R^{43}$, $R^{43}$ and $R^{44}$, $R^{45}$ and $R^{46}$, $R^{46}$ and $R^{47}$, $R^{47}$ and $R^{48}$, $R^{51}$ and $R^{52}$, $R^{52}$ and $R^{53}$, $R^{53}$ and $R^{54}$, $R^{55}$ and $R^{56}$, $R^{56}$ and $R^{57}$, $R^{57}$ and $R^{58}$, $R^{61}$ and $R^{62}$, $R^{62}$ and $R^{63}$, $R^{63}$ and $R^{64}$, $R^{64}$ and $R^{65}$, $R^{54}$ and $R^{61}$, $R^{55}$ and $R^{65}$, $R^{81}$ and $R^{82}$, $R^{82}$ and $R^{83}$, $R^{83}$ and $R^{84}$, R and $R^{86}$, $R^{86}$ and $R^{87}$, $R^{87}$ and $R^{88}$, and $R^{89}$ and $R^{90}$ each may be bonded to each other to form a cyclic structure; and $L^{13}$ to $L^{16}$ and $L^{18}$ each independently represent a substituted or unsubstituted arylene group or a substituted or unsubstituted heteroarylene group.

(3) The light-emitting material according to the item (1) or (2), wherein in the general formula (1), $R^3$ represents a cyano group.

(4) The light-emitting material according to any one of the items (1) to (3), wherein in the general formula (1), $R^1$ and $R^4$ each represent a group represented by the general formula (2).

(5) The light-emitting material according to any one of the items (1) to (4), wherein in the general formula (2), $L^{12}$ represents a phenylene group.

(6) The light-emitting material according to any one of the items (1) to (5), wherein the group represented by the general formula (2) is a group represented by the general formula (3).

(7) The light-emitting material according to the item (6), wherein in the general formula (3), $L^{13}$ represents a 1,3-phenylene group.

(8) The light-emitting material according to any one of the items (1) to (5), wherein the group represented by the general formula (2) is a group represented by the general formula (4).

(9) The light-emitting material according to the item (8), wherein in the general formula (4), $L^{14}$ represents a 1,4-phenylene group.

(10) The light-emitting material according to any one of the items (1) to (5), wherein the group represented by the general formula (2) is a group represented by the general formula (8).

(11) The light-emitting material according to the item (10), wherein in the general formula (8), $L^{18}$ represents a 1,4-phenylene group.

(12) The light-emitting material according to the item (1) or (2), wherein in the general formula (1), $R^1$ represents a group that satisfies the following condition A, and $R^2$ represents a substituted or unsubstituted aryl group; or in the general formula (1), $R^2$ represents a group that satisfies the following condition A, and at least one of $R^1$ and $R^3$ represents a substituted or unsubstituted aryl group; or in the general formula (1), $R^3$ represents a group that satisfies the following condition A, and at least one of $R^2$ and $R^4$ represents a substituted or unsubstituted aryl group:

condition A: a group represented by the general formula (2), provided that $R^{15}$ and $R^{16}$ are not bonded to each other, or a group represented by the general formula (3).

(13) The light-emitting material according to the item (1) or (2), wherein in the general formula (1), $R^1$ represents a group represented by the general formula (4), (5), (6), or (8), and $R^2$ represents a hydrogen atom; or in the general formula (1), $R^2$ represents a group represented by the general formula (4), (5), (6), or (8), and at least one of $R^1$ and $R^3$ represents a hydrogen atom; or in the general formula (1), $R^3$ represents a group represented by the general formula (4), (5), (6), or (8), and at least one of $R^2$ and $R^4$ represents a hydrogen atom.

(14) A delayed fluorescent emitter containing a compound represented by the following general formula (1):

General Formula (1)

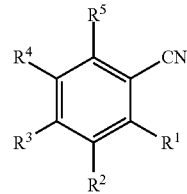

wherein in the general formula (1), from 0 to 1 of $R^1$ to $R^5$ represents a cyano group, from 1 to 5 of $R^1$ to $R^5$ each represent a group represented by the following general formula (2) or the following general formula (7), and the balance of $R^1$ to $R^5$ each represent a hydrogen atom or a substituent other than above:

General Formula (2)

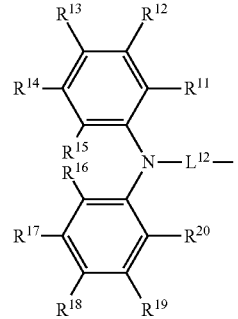

wherein in the general formula (2), $R^{11}$ to $R^{20}$ each independently represent a hydrogen atom or a substituent, provided that $R^{11}$ and $R^{12}$, $R^{12}$ and $R^{13}$, $R^{13}$ and $R^{14}$, $R^{14}$ and $R^{15}$, $R^{15}$ and $R^{16}$, $R^{16}$ and $R^{17}$, $R^{17}$ and $R^{18}$, $R^{18}$ and $R^{19}$, and $R^{19}$ and $R^{20}$ each may be bonded to each other to form a cyclic structure; and $L^{12}$ represents a substituted or unsubstituted arylene group or a substituted or unsubstituted heteroarylene group, provided that in the case where in the general formula (1), $R^3$ represents a cyano group, $R^2$ and $R^5$ each represent a hydrogen atom, and $R^1$ and $R^4$ each represent a group represented by the general formula (2), the general formula (2) does not represent a 4-(9-carbazolyl)phenyl group,

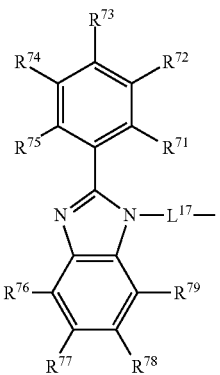

General Formula (7)

wherein in the general formula (7), $R^{71}$ to $R^{79}$ each independently represent a hydrogen atom or a substituent, provided that $R^{71}$ and $R^{72}$, $R^{72}$ and $R^{73}$, $R^{73}$ and $R^{74}$, $R^{74}$ and $R^{75}$, $R^{76}$ and $R^{77}$, $R^{77}$ and $R^{78}$, $R^{78}$ and $R^{79}$ each may be bonded to each other to form a cyclic structure; and $L^{17}$ represents a substituted or unsubstituted arylene group or a substituted or unsubstituted heteroarylene group.

(15) An organic light-emitting device containing the light-emitting material according to any one of the items (1) to (3).

(16) The organic light-emitting device according to the item (15), wherein the organic light-emitting device emits delayed fluorescent light.

(17) The organic light-emitting device according to the item (15) or (16), wherein the organic light-emitting device is an organic electroluminescent device.

(18) A compound represented by the following general formula (1'):

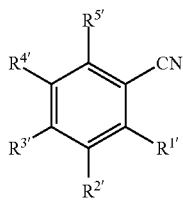

General Formula (1')

wherein in the general formula (1'), from 0 to 1 of $R^{1'}$ to $R^{5'}$ represents a cyano group, from 1 to 5 of $R^{1'}$ to $R^{5'}$ each represent a group represented by the following general formula (2') or the following general formula (7), and the balance of $R^{1'}$ to $R^{5'}$ each represent a hydrogen atom or a substituent other than above:

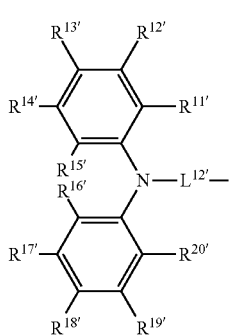

General Formula (2')

wherein in the general formula (2'), $R^{11'}$ to $R^{20'}$ each independently represent a hydrogen atom or a substituent, provided that $R^{11'}$ and $R^{12'}$, $R^{12'}$ and $R^{13'}$, $R^{13'}$ and $R^{14'}$, $R^{14'}$ and $R^{15'}$, $R^{15'}$ and $R^{16'}$, $R^{16'}$ and $R^{17'}$, $R^{17'}$ and $R^{18'}$, $R^{18'}$ and $R^{19'}$, and $R^{19'}$ and $R^{20'}$ each may be bonded to each other to form a cyclic structure; and $L^{12'}$ represents a substituted or unsubstituted arylene group or a substituted or unsubstituted heteroarylene group,

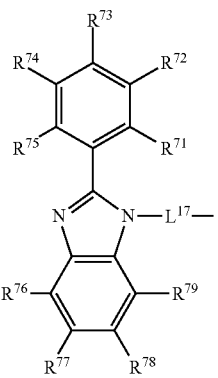

General Formula (7)

wherein in the general formula (7), $R^{71}$ to $R^{79}$ each independently represent a hydrogen atom or a substituent, provided that $R^{71}$ and $R^{72}$, $R^{72}$ and $R^{73}$, $R^{73}$ and $R^{74}$, $R^{74}$ and $R^{75}$, $R^{76}$ and $R^{77}$, $R^{77}$ and $R^{78}$, $R^{78}$ and $R^{79}$ each may be bonded to each other to form a cyclic structure; and $L^{17}$ represents a substituted or unsubstituted arylene group or a substituted or unsubstituted heteroarylene group.

Advantageous Effects of Invention

The compound of the invention is useful as a light-emitting material. The compound of the invention includes one that emits delayed fluorescent light. The organic light-emitting device using the compound of the invention as a light-emitting material is capable of achieving a high light emission efficiency (photoluminescence quantum efficiency, electroluminescence quantum efficiency, or both).

DESCRIPTION OF EMBODIMENTS

Figure 1:
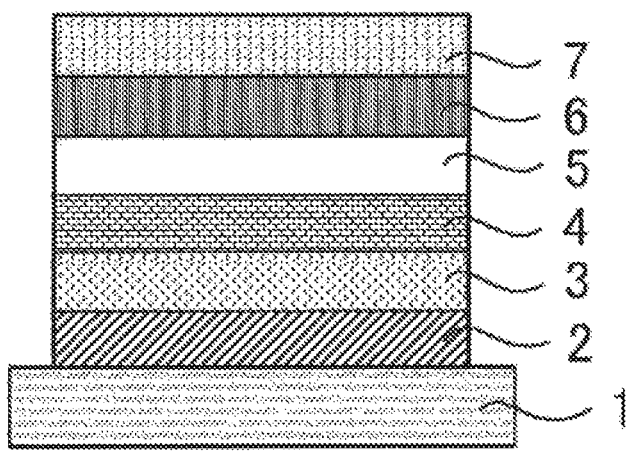
FIG. 1 shows a schematic cross sectional view showing an example of a layer structure of an organic electroluminescent device.

The contents of the invention will be described in detail below. The constitutional elements may be described below with reference to representative embodiments and specific examples of the invention, but the invention is not limited to the embodiments and the examples. In the description, a numerical range expressed with reference to an upper limit and/or a lower limit means a range that includes the upper limit and/or the lower limit. In the invention, the hydrogen atom that is present in the compound used in the invention is not particularly limited in isotope species, and for example, all the hydrogen atoms in the molecule may be $^1$H, and all or a part of them may be $^2$H (deuterium (D)).

Compound Represented by General Formula (1)

The light-emitting material of the invention contains a compound represented by the following general formula (1).

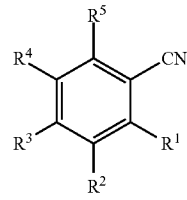

General Formula (1)

In the general formula (1), from 0 to 1 of $R^1$ to $R^5$ represents a cyano group, from 1 to 5 of $R^1$ to $R^5$ each represent a group represented by the following general formula (2) or the following general formula (7), and the balance of $R^1$ to $R^5$ each represent a hydrogen atom or a substituent other than above.

It is considered that the compound represented by the general formula (1) may have an enhanced light emission efficiency since the benzene ring as an acceptor tends to be oriented horizontally.

In the general formula (1), a cyano group may not be present in $R^1$ to $R^5$, and cyano groups may be present in only one of $R^1$ to $R^5$, or in from 2 to 4 thereof.

In the case where a cyano group is present in only one of $R^1$ to $R^5$, any one of $R^2$ to $R^4$ preferably represents a cyano group, and $R^3$ more preferably represents a cyano group.

In the case where cyano groups are present in from 2 to 4 of $R^1$ to $R^5$, at least two of $R^2$ to $R^4$ preferably represent cyano groups. For example, in the case where two of $R^1$ to $R^5$ represent cyano groups, it is preferred that $R^2$ and $R^3$ represent cyano groups, or $R^3$ and $R^4$ represent cyano groups. In the case where three of $R^1$ to $R^5$ represent cyano groups, it is preferred that $R^2$ to $R^4$ represent cyano groups. In the case where four of $R^1$ to $R^5$ represent cyano groups, it is preferred that $R^1$ to $R^4$ represent cyano groups, or $R^2$ to $R^5$ represent cyano groups.

From 1 to 5 of $R^1$ to $R^5$ each represent a group represented by the following general formula (2) or (7). The group represented by the general formula (2) or (7) may be only one of R to $R^5$, or may be from 2 to 5 thereof.

In the case where the group represented by the general formula (2) or (7) is only one of $R^1$ to $R^5$, any one of $R^1$, $R^2$, $R^4$, and $R^5$ preferably represents the group represented by the general formula (2) or (7), and $R^1$ or $R^4$ more preferably represents the group represented by the general formula (2) or (7).

In the case where from 2 to 5 of $R^1$ to $R^5$ each represent the group represented by the general formula (2) or (7), at least one of $R^1$ and $R^2$ and at least one of $R^4$ and $R^5$ each preferably represent the group represented by the general formula (2) or (7). For example, in the case where two of $R^1$ to $R^5$ each represent the group represented by the general formula (2) or (7), $R^1$ or $R^2$, and $R^4$ or $R^5$ each preferably represent the group represented by the general formula (2) or (7), and $R^1$ and $R^4$ each more preferably represent the group represented by the general formula (2) or (7). In the case where three of $R^1$ to $R^5$ each represent the group represented by the general formula (2) or (7), three of $R^1$, $R^2$, $R^4$, and $R^5$ each preferably represent the group represented by the general formula (2) or (7). In the case where four of $R^1$ to $R^5$ each represent the group represented by the general formula (2) or (7), $R^1$, $R^2$, $R^4$, and $R^5$ each preferably represent the group represented by the general formula (2) or (7).

Preferred examples of the compound include a compound represented by the general formula (1), in which $R^3$ represents a cyano group, and $R^1$ or $R^2$, and $R^4$ or $R^5$ each represent the group represented by the general formula (2) or (7), and more preferred examples of the compound include a compound represented by the general formula (1), in which $R^3$ represents a cyano group, and $R^1$ and $R^4$ each represent the group represented by the general formula (2) or (7), and a compound represented by the general formula (1), in which $R^3$ represents a cyano group, and $R^2$ and $R^5$ each represent the group represented by the general formula (2) or (7). The plural groups represented by the general formula (2) or (7) in the general formula (1) may be the same as or different from each other, and are preferably the same as each other. The compound represented by the general formula (1) preferably has a symmetric structure. Specifically, $R^1$ and $R^4$, and $R^2$ and $R^5$ each are preferably the same as each other, and $R^3$ preferably represents a cyano group.

General Formula (2)

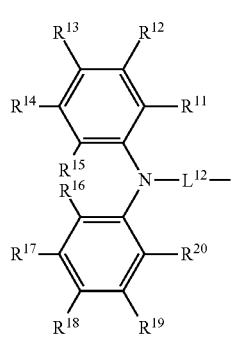

In the general formula (2), $R^{11}$ to $R^{20}$ each independently represent a hydrogen atom or a substituent. The number of the substituent is not particularly limited, and all $R^{11}$ to $R^{20}$ may be unsubstituted (i.e., hydrogen atoms). In the case where two or more of $R^{11}$ to $R^{20}$ each represent a substituent, the plural substituents may be the same as or different from each other.

Examples of the substituent that may be represented by $R^{11}$ to $R^{20}$ and the substituent that may be represented by $R^1$ to $R^5$ include a hydroxyl group, a halogen atom, a cyano group, an alkyl group having from 1 to 20 carbon atoms, an alkoxy group having from 1 to 20 carbon atoms, an alkylthio group having from 1 to 20 carbon atoms, an alkyl-substituted amino group having from 1 to 20 carbon atoms, an acyl group having from 2 to 20 carbon atoms, an aryl group having from 6 to 40 carbon atoms, a heteroaryl group having from 3 to 40 carbon atoms, an alkenyl group having from 2 to 10 carbon atoms, an alkynyl group having from 2 to 10 carbon atoms, an alkoxycarbonyl group having from 2 to 10 carbon atoms, an alkylsulfonyl group having from 1 to 10 carbon atoms, a haloalkyl group having from 1 to 10 carbon atoms, an amide group, an alkylamide group having from 2 to 10 carbon atoms, a trialkylsilyl group having from 3 to 20 carbon atoms, a trialkylsilylalkyl group having from 4 to 20 carbon atoms, a trialkylsilylalkenyl group having from 5 to 20 carbon atoms, a trialkylsilylalkynyl group having from 5 to 20 carbon atoms, and a nitro group. In these specific examples, the substituent that is capable of being further substituted with a substituent may be substituted. More preferred examples of the substituent include a halogen atom, a cyano group, a substituted or unsubstituted alkyl group having from 1 to 20 carbon atoms, an alkoxy group having from 1 to 20 carbon atoms, a substituted or unsubstituted aryl group having from 6 to 40 carbon atoms, a substituted or unsubstituted heteroaryl group having from 3 to 40 carbon atoms, and a dialkyl-substituted amino group having from 1 to 20 carbon atoms. Further preferred examples of the substituent include a fluorine atom, a chlorine atom, a cyano group, a substituted or unsubstituted alkyl group having from 1 to 10 carbon atoms, a substituted or unsubstituted alkoxy group having from 1 to 10 carbon atoms, a substituted or unsubstituted aryl group having from 6 to 15 carbon atoms, and a substituted or unsubstituted heteroaryl group having from 3 to 12 carbon atoms.

$R^{11}$ and $R^{12}$, $R^{12}$ and $R^{13}$, $R^{13}$ and $R^{14}$, $R^{14}$ and $R^{15}$, $R^{15}$ and $R^{16}$, $R^{16}$ and $R^{17}$, $R^{17}$ and $R^{18}$, $R^{18}$ and $R^{19}$, and $R^{19}$ and $R^{20}$ each may be bonded to each other to form a cyclic structure. The cyclic structure may be an aromatic ring or an aliphatic ring, and may be a structure containing a hetero atom, and the cyclic structure may be a condensed ring containing two or more rings. The hetero atom referred herein is preferably selected from the group consisting of a nitrogen atom, an oxygen atom, and a sulfur atom. Examples of the cyclic structure formed include a benzene ring, a naphthalene ring, a pyridine ring, a pyridazine ring, a pyrimidine ring, a pyrazine ring, a pyrrole ring, an imidazole ring, a pyrazole ring, a triazole ring, an imidazoline ring, an oxazole ring, an isoxazole ring, a thiazole ring, an isothiazole ring, a cyclohexadiene ring, a cyclohexene ring, a cyclopentaene ring, a cycloheptatriene ring, a cycloheptadiene ring, and a cycloheptaene ring.

In the general formula (2), $L^{12}$ represents a substituted or unsubstituted arylene group or a substituted or unsubstituted heteroarylene group. The aromatic ring constituting the arylene group represented by $L^{12}$ may be a monocyclic ring or a fused ring containing two or more aromatic rings fused to each other. The number of carbon atoms of the aromatic ring is preferably from 6 to 22, more preferably from 6 to 18, further preferably from 6 to 14, and still further preferably from 6 to 10. Specific examples of the arylene group include a phenylene group and a naphthalenediyl group. The heterocyclic ring constituting the heteroarylene group represented by $L^{12}$ may be a monocyclic ring or a fused ring containing one or more of a heterocyclic ring and an aromatic ring or a heterocyclic ring fused to each other. The number of carbon atoms of the heterocyclic ring is preferably from 5 to 22, more preferably from 5 to 18, further preferably from 5 to 14, and still further preferably from 5 to 10. The hetero atom constituting the heterocyclic ring is preferably a nitrogen atom. Specific examples of the heterocyclic ring include a pyridine ring, a pyridazine ring, a pyrimidine ring, a triazine ring, a triazole ring, and a benzotriazole ring. Preferred examples of the group represented by $L^{12}$ include a phenylene group. In the case where $L^{12}$ represents a phenylene group, the phenylene group may be any of a 1,2-phenylene group, a 1,3-phenylene group, and a 1,4-phenylene group. The group represented by $L^{12}$ may be further substituted by a substituent. The number of the substituent and the substitution position thereof on $L^{12}$ are not particularly limited, and the substituent is preferably introduced to the ortho-position with respect to the position where the nitrogen atom is bonded. For the description and the preferred range of the substituent that may be introduced to $L^{12}$, reference may be made to the description and the preferred range of the substituent that may be represented by $R^1$ to $R^5$.

The group represented by the general formula (2) is preferably a group represented by any one of the following general formulae (3) to (6) and (8).

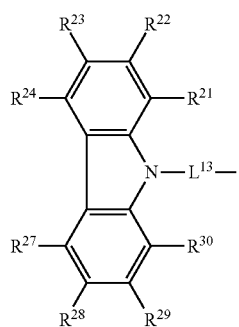

General Formula (3)

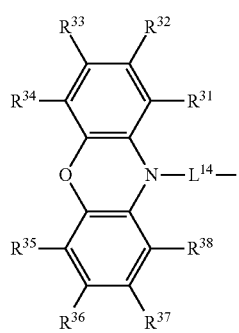

General Formula (4)

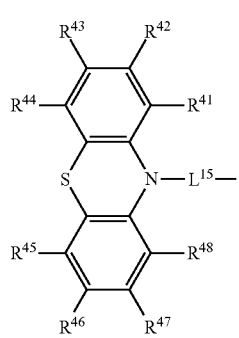

General Formula (5)

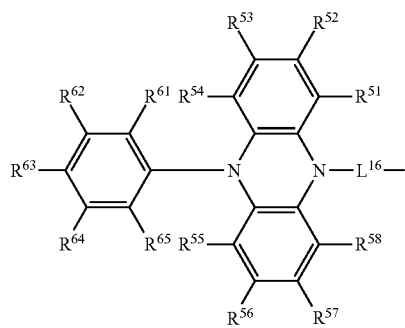

General Formula (6)

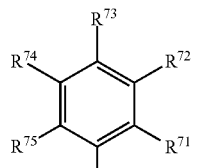

General Formula (7)

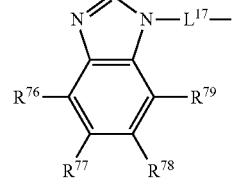

General Formula (8)

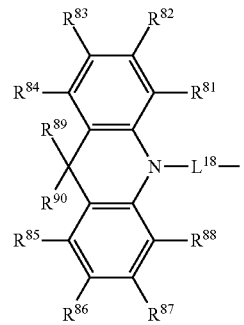

In the general formulae (3) to (8), $R^{21}$ to $R^{24}$, $R^{27}$ to $R^{38}$, $R^{41}$ to $R^{48}$, $R^{51}$ to $R^{58}$, $R^{61}$ to $R^{65}$, $R^{71}$ to $R^{79}$, and $R^{81}$ to $R^{90}$ each independently represent a hydrogen atom or a substituent. For the description and the preferred range of the substituent herein, reference may be made to the description and the preferred range of the substituent that may be represented by $R^1$ to $R^5$. $R^{21}$ to $R^{24}$, $R^{27}$ to $R^{38}$, $R^{41}$ to $R^{48}$, $R^{51}$ to $R^{58}$, $R^{61}$ to $R^{65}$, $R^{71}$ to $R^{79}$, and $R^{81}$ to $R^{90}$ each independently preferably represent a group represented by any one of the general formulae (3) to (8). $R^{89}$ and $R^{90}$ each preferably represent a substituted or unsubstituted alkyl group, and more preferably a substituted or unsubstituted alkyl group having from 1 to 6 carbon atoms. The number of the substituent in the general formulae (3) to (8) is not particularly limited. The case where all the positions are unsubstituted (i.e., hydrogen atoms) is also preferred. In the case where two or more substituents are present in the general formulae (3) to (8), the substituents may be the same as or different from each other. In the case where a substituent is present in the general formula (3) to (8), the substituent is preferably any of $R^{22}$ to $R^{24}$ and $R^{27}$ to $R^{29}$, and more preferably at least one of $R^{23}$ and $R^{28}$, for the general formula (3), is preferably any of $R^{32}$ to $R^{37}$ for the general formula (4), is preferably any of $R^{42}$ to $R^{47}$ for the general formula (5), is preferably any of $R^{52}$, $R^{53}$, $R^{56}$, $R^{57}$, and $R^{62}$ to $R^{64}$ for the general formula (6), is preferably any of $R^{72}$ to $R^{74}$, $R^{77}$, and $R^{78}$ for the general formula (7), and is preferably any of $R^{82}$ to $R^{87}$, $R^{89}$, and $R^{90}$ for the general formula (8)

In the general formulae (3) to (8), $R^{21}$ and $R^{22}$, $R^{22}$ and $R^{23}$, $R^{23}$ and $R^{24}$, $R^{27}$ and $R^{28}$, $R^{28}$ and $R^{29}$, $R^{29}$ and $R^{30}$, $R^{31}$ and $R^{32}$, $R^{32}$ and $R^{33}$, $R^{33}$ and $R^{34}$, $R^{35}$ and $R^{36}$, $R^{36}$ and $R^{37}$, $R^{37}$ and $R^{38}$, $R^{41}$ and $R^{42}$, $R^{42}$ and $R^{43}$, $R^{43}$ and $R^{44}$, $R^{45}$ and $R^{46}$, $R^{46}$ and $R^{47}$, $R^{47}$ and $R^{48}$, $R^{51}$ and $R^{52}$, $R^{52}$ and $R^{53}$, $R^{53}$ and $R^{54}$, $R^{55}$ and $R^{56}$, $R^{56}$ and $R^{57}$, $R^{57}$ and $R^{58}$, $R^{61}$ and $R^{62}$, $R^{62}$ and $R^{63}$, $R^{63}$ and $R^{64}$, $R^{64}$ and $R^{65}$, $R^{54}$ and $R^{61}$, $R^{55}$ and $R^{65}$, $R^{71}$ and $R^{72}$, $R^{72}$ and $R^{73}$, $R^{73}$ and $R^{74}$, $R^{74}$ and $R^{75}$, $R^{76}$ and $R^{77}$, $R^{77}$ and $R^{78}$, $R^{78}$ and $R^{79}$, $R^{81}$ and $R^{78}$, $R^{82}$ and $R^{83}$, $R^{83}$ and $R^{84}$, $R^{85}$ and $R^{86}$, $R^{86}$ and $R^{87}$, $R^{87}$ and $R^{88}$, and $R^{89}$ and $R^{90}$ each may be bonded to each other to form a cyclic structure. For the description and the preferred examples of the cyclic structure, reference may be made to the description and the preferred examples of the cyclic structure formed by bonding $R^{11}$, $R^{12}$ and the like in the general formula (2).

In the general formula (3) to (8), $L^{13}$ to $L^{18}$ each independently represent a substituted or unsubstituted arylene group or a substituted or unsubstituted heteroarylene group. For the descriptions and the preferred ranges of the arylene group and the heteroarylene group represented by $L^{13}$ to $L^{18}$ and the substituent that may be introduced to the groups, reference may be made to the descriptions and the preferred ranges of the arylene group and the heteroarylene group represented by $L^{12}$ and the substituent that may be introduced to the groups. In the case where the group represented by the general formula (2) is a group represented by the general formula (3), $L^{13}$ preferably represents a 1,3-phenylene group; in the case where the group represented by the general formula (2) is a group represented by the general formula (4), $L^{14}$ preferably represents a 1,4-phenylene group; and in the case where the group represented by the general formula (2) is a group represented by the general formula (8), $L^{18}$ preferably represents a 1,4-phenylene group.

All the groups represented by the general formula (2) present in the general formula (1) each preferably represent a group represented by any one of the general formulae (3) to (8). For example, such a case may be exemplified that all the groups each represent a group represented by the general formula (3), (4), or (8). In the case where all the groups each represent a 4-(9-carbazolyl)phenyl group, which is one embodiment of the general formula (3), three or more of the groups are preferably present in one molecule, and in the case where two or less of the groups are present in one molecule, the groups each are preferably substituted by an alkyl group or the like. In the compound represented by the general formula (1), examples of the preferred compound include the following compounds (I) to (III) and (IV) to (VI).

(I) A compound represented by the general formula (1), in which $R^1$ represents a group that satisfies the following condition A, and $R^2$ represents a substituted or unsubstituted aryl group (II) A compound represented by the general formula (1), in which $R^2$ represents a group that satisfies the following condition A, and at least one of $R^1$ and $R^3$ represents a substituted or unsubstituted aryl group (III) A compound represented by the general formula (1), in which $R^3$ represents a group that satisfies the following condition A, and at least one of $R^2$ and $R^4$ represents a substituted or unsubstituted aryl group Condition A: The group is a group represented by the general formula (2), in which $R^{15}$ and $R^{16}$ are groups that are not bonded to each other, or is a group represented by the general formula (3).

(IV) A compound represented by the general formula (1), in which $R^1$ represents a group represented by the general formula (4), (5), (6), or (8), and $R^2$ represents a hydrogen atom (V) A compound represented by the general formula (1), in which $R^2$ represents a group represented by the general formula (4), (5), (6), or (8), and at least one of $R^1$ and $R^3$ represents a hydrogen atom (VI) A compound represented by the general formula (1), in which $R^3$ represents a group represented by the general formula (4), (5), (6), or (8), and at least one of $R^2$ and $R^4$ represents a hydrogen atom In the compound (II), any one of $R^1$ and $R^3$ may represents a substituted or unsubstituted aryl group, or both of them each represent a substituted or unsubstituted aryl group, and both $R^1$ and $R^3$ each preferably represents a substituted or unsubstituted aryl group. In the compound (III), any one of $R^2$ and $R^4$ may represents a substituted or unsubstituted aryl group, or both of them each represent a substituted or unsubstituted aryl group, and both $R^2$ and $R^4$ each preferably represents a substituted or unsubstituted aryl group.

For the description and the preferred range of the aromatic ring constituting the substituted or unsubstituted aryl group in the compounds (I) to (III), reference may be made to the description and the preferred range of the aromatic ring constituting $L^{12}$ in the general formula (2). In the compounds (I) to (III), the substituted or unsubstituted aryl group is preferably a substituted or unsubstituted phenyl group, and more preferably an unsubstituted phenyl group. For the description and the preferred range of the substituent that may be substituted on the aryl group, reference may be made to the description and the preferred range of the substituent that may be represented by $R^1$ to $R^5$ and the like. The substituted or substituted aryl group may be a group that satisfies the condition A.

Specific examples of the compound represented by the general formula (1) shown below. However, the compound represented by the general formula (1) capable of being used in the invention is not construed as being limited to the specific examples.

Compound 1

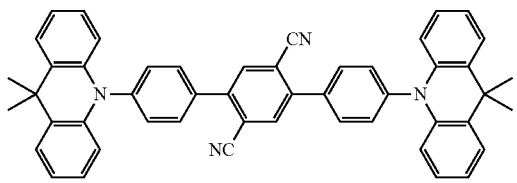

Compound 2

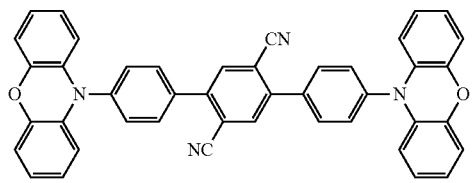

-continued
Compound 3
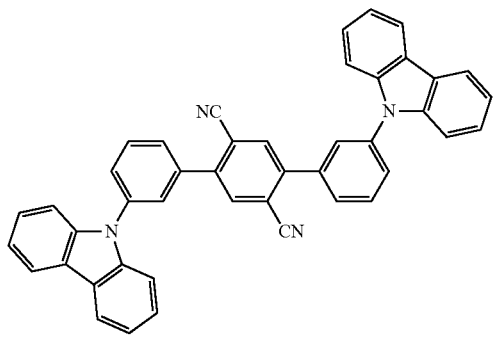
Compound 4
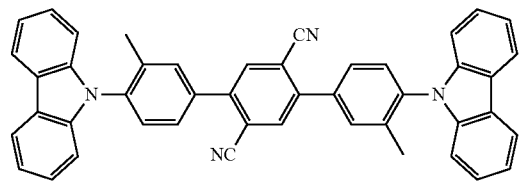
Compound 5
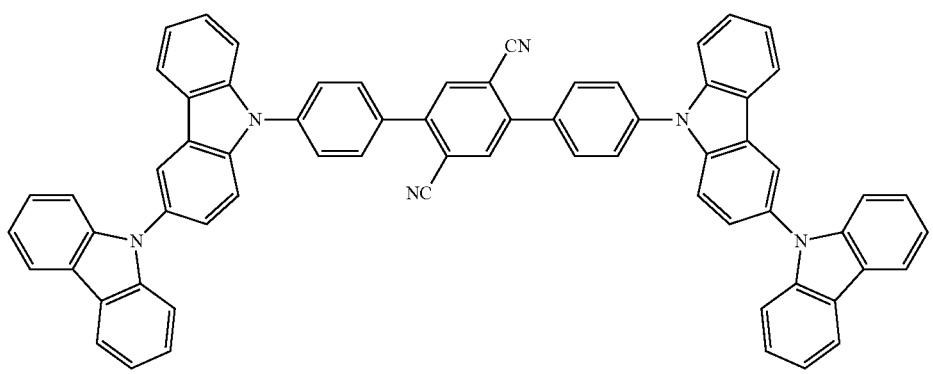
Compound 6
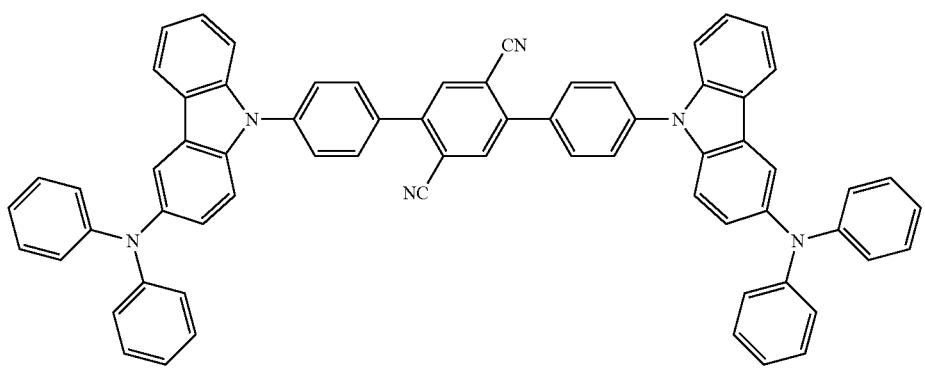
Compound 7
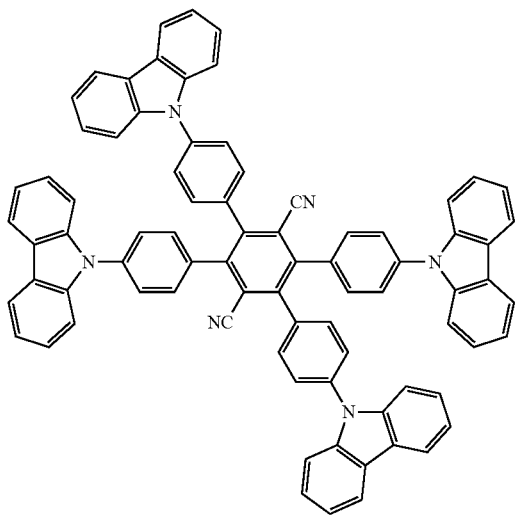
Compound 8
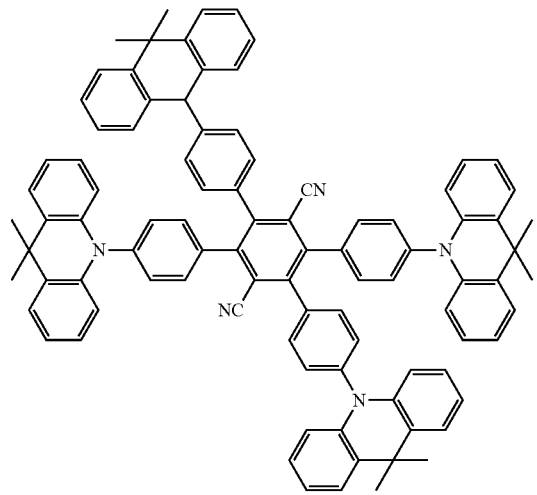

Compound 9
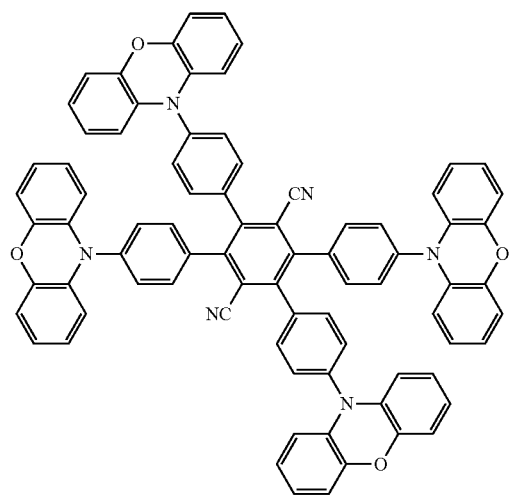
Compound 10
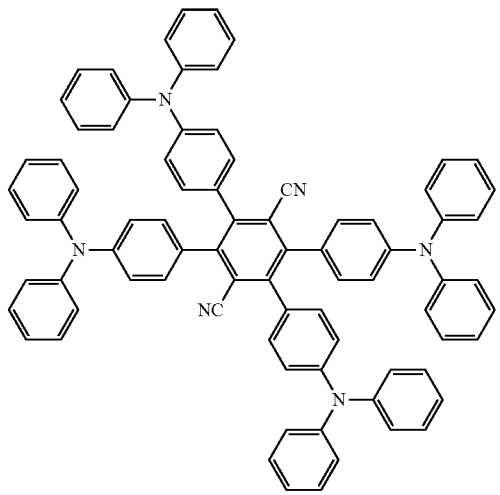
Compound 11
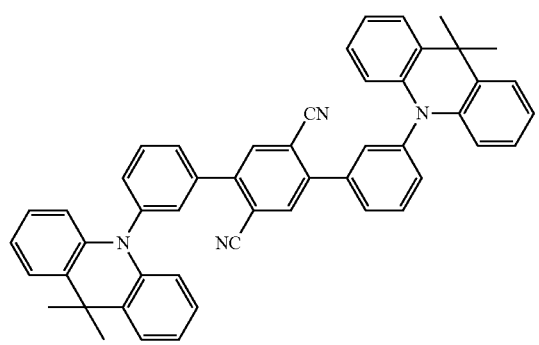
Compound 12
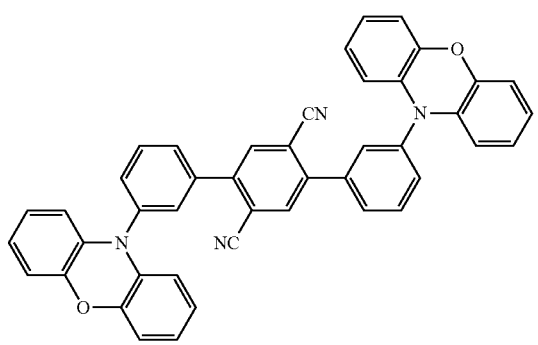
Compound 13
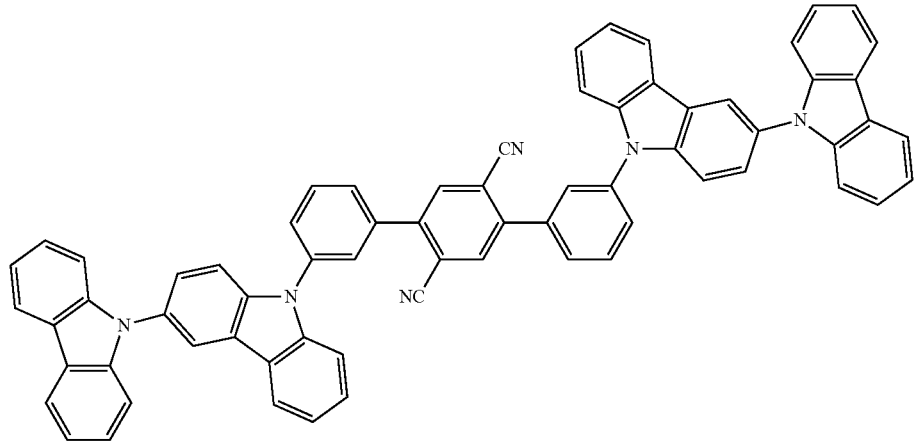

-continued
Compound 14
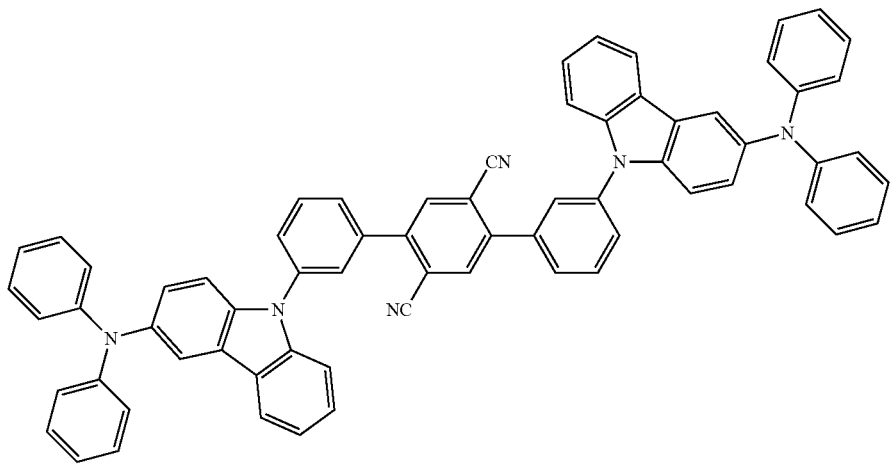
Compound 15
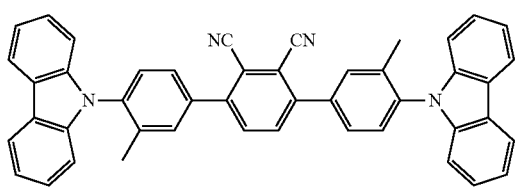
Compound 16
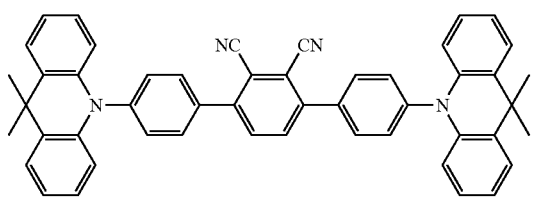
Compound 17
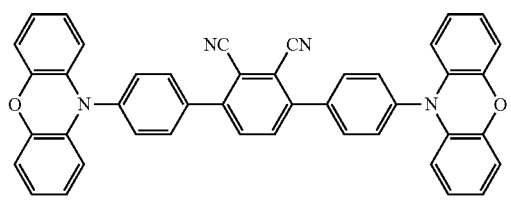
Compound 18
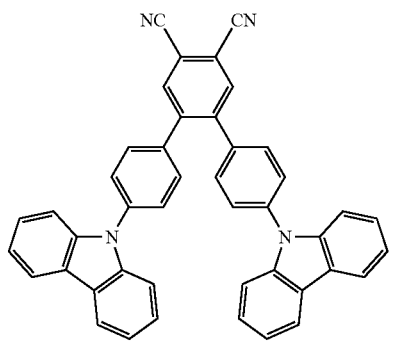
Compound 19
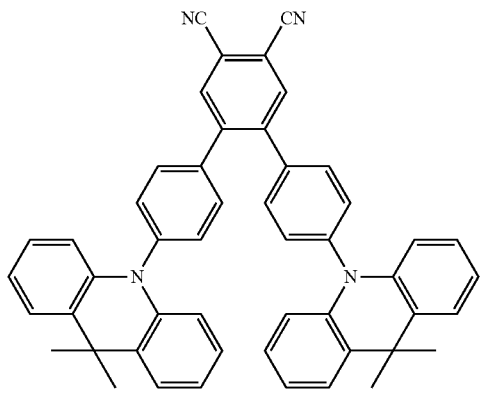
Compound 20
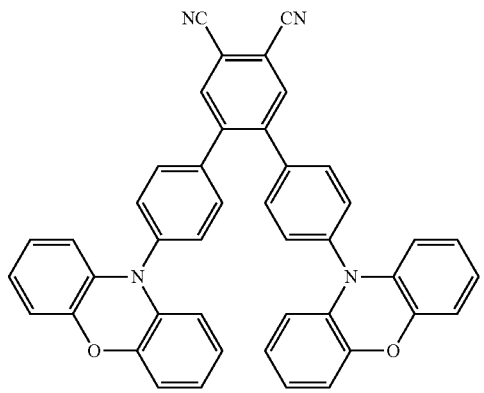

-continued
Compound 21
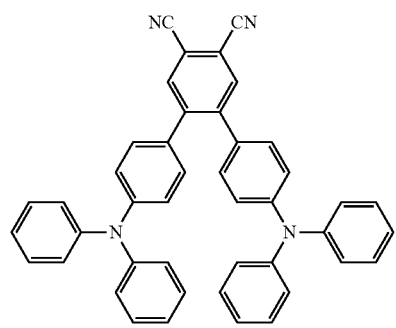
Compound 22
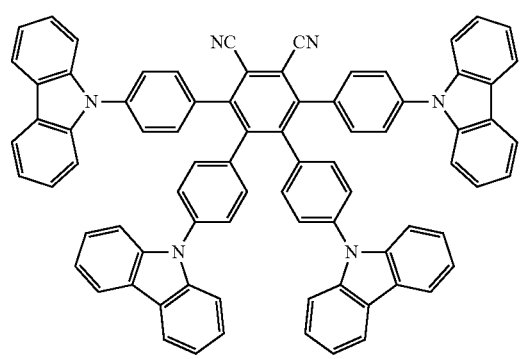
Compound 23
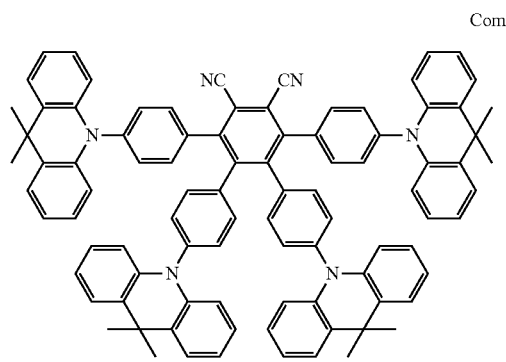
Compound 24
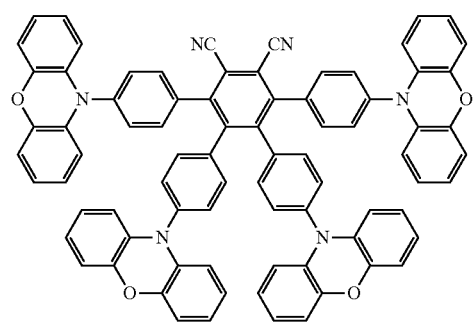
Compound 25
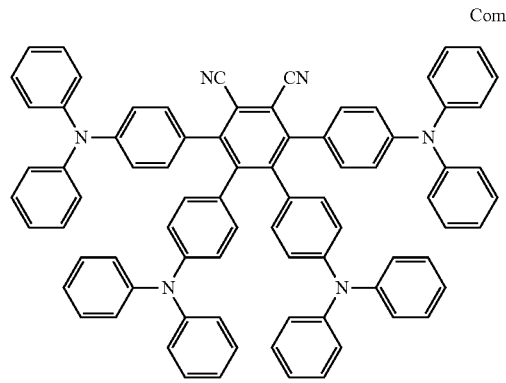
Compound 26
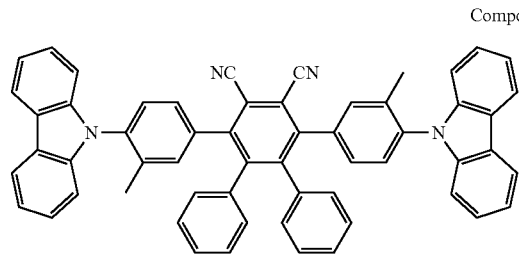
Compound 27
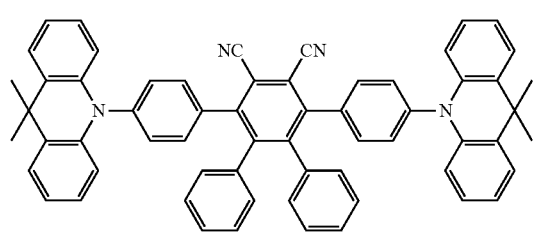
Compound 28
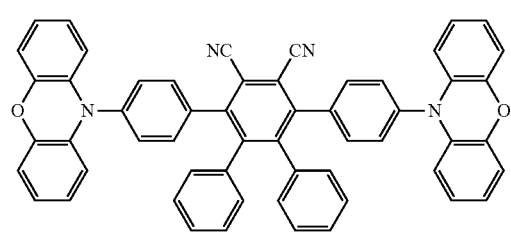

Compound 29

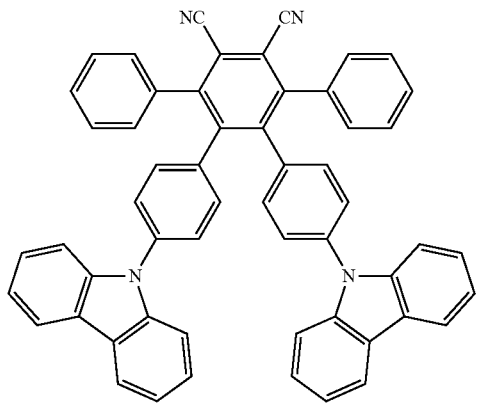

Compound 30

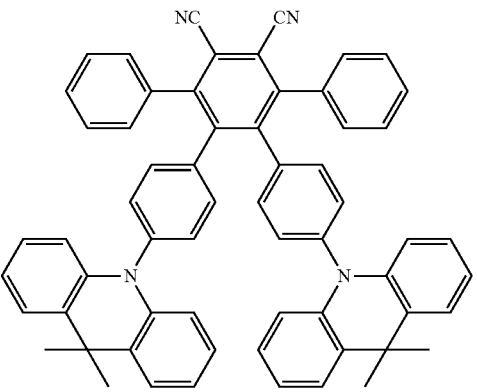

Compound 31

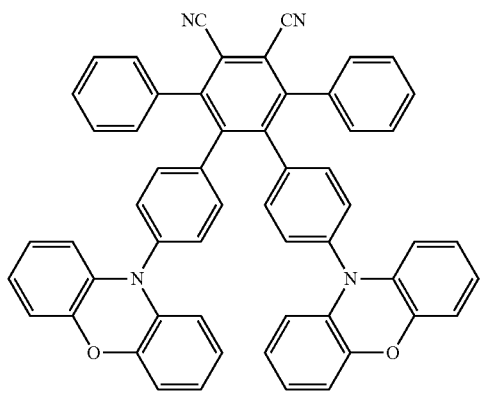

Compound 32

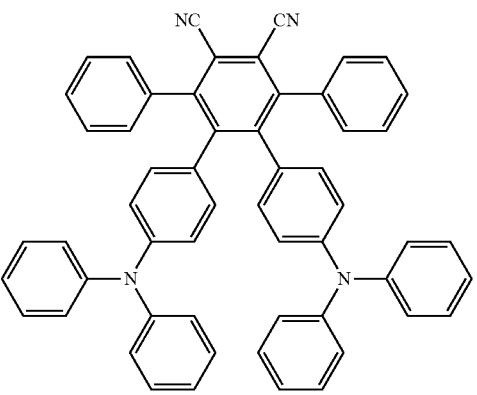

Compound 33

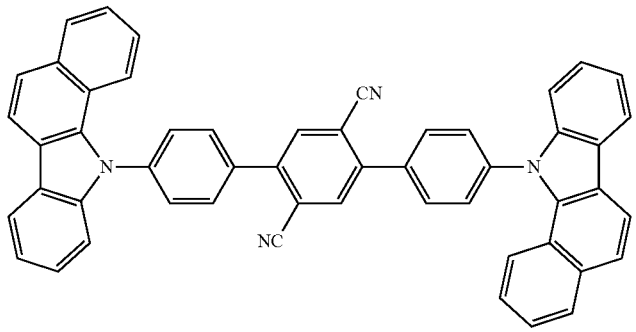

The molecular weight of the compound represented by the general formula (1) is preferably 1,500 or less, more preferably 1,200 or less, further preferably 1,000 or less, and still further preferably 800 or less, for example, in the case where an organic layer containing the compound represented by the general formula (1) is intended to be formed as a film by a vapor deposition method. The lower limit of the molecular weight is the molecular weight of the smallest compound represented by the general formula (1).

The compound represented by the general formula (1) may be formed into a film by a coating method irrespective of the molecular weight thereof. The compound that has a relatively large molecular weight may be formed into a film by a coating method.

As an application of the invention, it may be considered that a compound that contains plural structures each represented by the general formula (1) in the molecule is used as a light-emitting material.

For example, it may be considered that a polymerizable group is introduced in advance to the structure represented by the general formula (1), and a polymer obtained by polymerizing the polymerizable group is used as a light-emitting material. Specifically, it may be considered that a monomer that has a polymerizable functional group at any of $R^1$ to $R^5$ in the general formula (1) is prepared, and is homopolymerized or copolymerized with another monomer to prepare a polymer containing repeating units, and the polymer is used as a light-emitting material. In alternative, it may be considered that the compounds represented by the general formula (1) are reacted to form a dimer or a trimer, and the dimer or the trimer is used as a light-emitting material.

Examples of the polymer having the repeating unit containing the structure represented by the general formula (1) include a polymer containing a structure represented by the following general formula (9) or (10).

General Formula (9)

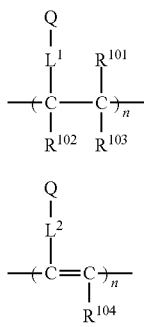

General Formula (10)

In the general formulae (9) and (10), Q represents a group containing the structure represented by the general formula (1), and $L^1$ and $L^2$ each represent a linking group. The linking group preferably has from 0 to 20 carbon atoms, more preferably from 1 to 15 carbon atoms, and further preferably from 2 to 10 carbon atoms. The linking group preferably has a structure represented by $—X^{11}-L^{11}-$, wherein $X^{11}$ represents an oxygen atom or a sulfur atom, and preferably an oxygen atom, and $L^{11}$ represents a linking group, preferably a substituted or unsubstituted alkylene group or a substituted or unsubstituted arylene group, and more preferably a substituted or unsubstituted alkylene group having from 1 to 10 carbon atoms or a substituted or unsubstituted phenylene group.

In the general formulae (9) and (10), $R^{101}$, $R^{102}$, $R^{103}$ and $R^{104}$ each independently represent a substituent, preferably a substituted or unsubstituted alkyl group having from 1 to 6 carbon atoms, a substituted or unsubstituted alkoxy group having from 1 to 6 carbon atoms, or a halogen atom, more preferably an unsubstituted alkyl group having from 1 to 3 carbon atoms, an unsubstituted alkoxy group having from 1 to 3 carbon atoms, a fluorine atom or a chlorine atom, and further preferably an unsubstituted alkyl group having from 1 to 3 carbon atoms or an unsubstituted alkoxy group having from 1 to 3 carbon atoms.

The linking group represented by L and $L^2$ may be bonded to any of $R^1$ to $R^5$ of the structure of the general formula (1), any of $R^{11}$ to $R^{20}$ of the structure of the general formula (2), any of $R^{21}$ to $R^{24}$ and $R^{27}$ to $R^{30}$ of the structure of the general formula (3), any of $R^{31}$ to $R^{38}$ of the structure of the general formula (4), any of $R^{41}$ to $R^{48}$ of the structure of the general formula (5), any of $R^{51}$ to $R^{58}$ and $R^{61}$ to $R^{65}$ of the structure of the general formula (6), any of $R^{71}$ to $R^{78}$ of the structure of the general formula (7), and any of $R^{81}$ to $R^{90}$ of the structure of the general formula (8), constituting Q. Two or more of the linking groups may be boded to one group represented by Q to form a crosslinked structure or a network structure.

Specific examples of the structure of the repeating unit include structures represented by the following formulae (11) to (14).

Formula (11)

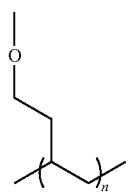

Formula (12)

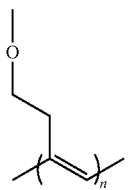

Formula (13)

Formula (14)

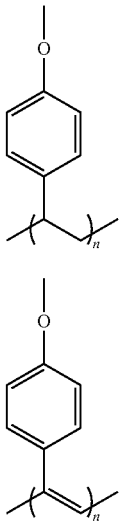

The polymer having the repeating unit containing the structure represented by any of the formulae (11) to (14) may be synthesized in such a manner that a hydroxyl group is introduced to any of $R^1$ to $R^5$ in the structure represented by the general formula (1), and the hydroxyl group as a linker is reacted with the following compound to introduce a polymerizable group thereto, followed by polymerizing the polymerizable group.

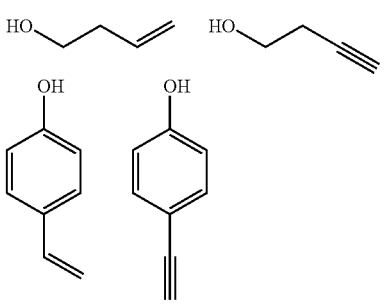

The polymer containing the structure represented by the general formula (1) in the molecule may be a polymer containing only a repeating unit having the structure represented by the general formula (1), or a polymer further containing a repeating unit having another structure. The repeating unit having the structure represented by the general formula (1) contained in the polymer may be only one kind or two or more kinds. Examples of the repeating unit that does not have the structure represented by the general formula (1) include a repeating unit derived from a monomer that is used for ordinary copolymerization. Examples of the repeating unit include a repeating unit derived from a monomer having an ethylenic unsaturated bond, such as ethylene and styrene.

Compound Represented by General Formula (1')

The compound represented by the general formula (1') is a novel compound.

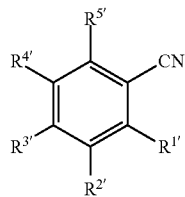

General Formula (1')

In the general formula (1'), from 0 to 1 of $R^{1'}$ to $R^{5'}$ represents a cyano group, from 1 to 5 of $R^{1'}$ to $R^{5'}$ each represent a group represented by the following general formula (2') or the following general formula (7), and the balance of $R^{1'}$ to $R^{5'}$ each represent a hydrogen atom or a substituent other than above.

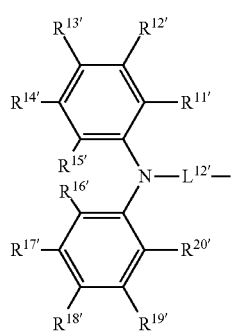

General Formula (2')

In the general formula (2'), $R^{11'}$ to $R^{20'}$ each independently represent a hydrogen atom or a substituent, provided that $R^{11'}$ and $R^{12'}$, $R^{12'}$ and $R^{13'}$, $R^{13'}$ an $R^{14'}$, $R^{14'}$ and $R^{15'}$, $R^{15'}$ and $R^{16'}$, $R^{16'}$ and $R^{17'}$, $R^{17'}$ and $R^{18'}$, $R^{18'}$ and $R^{19'}$, and $R^{19'}$ and $R^{20'}$ each may be bonded to each other to form a cyclic structure; and $L^{12'}$ represents a substituted or unsubstituted arylene group or a substituted or unsubstituted heteroarylene group.

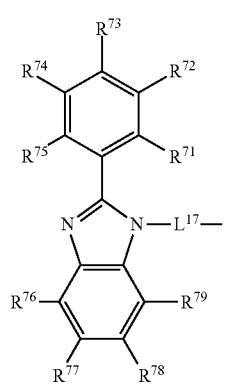

General Formula (7)

In the general formula (7), $R^{71}$ to $R^{79}$ each independently represent a hydrogen atom or a substituent, provided that $R^{71}$ and $R^{72}$, $R^{72}$ and $R^{73}$, $R^{73}$ and $R^{74}$, $R^{74}$ and $R^{75}$, $R^{76}$ and $R^{77}$, $R^{77}$ and $R^{78}$, $R^{78}$ and $R^{79}$ each may be bonded to each other to form a cyclic structure; and $L^{17}$ represents a substituted or unsubstituted arylene group or a substituted or unsubstituted heteroarylene group.

For the descriptions and the preferred ranges of $R^{1'}$ to $R^{5'}$, $R^{11'}$ to $R^{20'}$, and $L^{12'}$ in the general formula (1'), reference may be made to the descriptions of the compound represented by the general formula (1).

Synthesis Method of Compound Represented by General Formula (1')

The compound represented by the general formula (1') may be synthesized by combining the known reactions. For example, a compound represented by the general formula (1'), in which $R^{3'}$ represents a cyano group, $R^{1'}$ and $R^{4'}$ each represent a group represented by the general formula (2'), and $L^{12'}$ represents a 1,4-phenylene group, can be synthesized in such a manner that the carboxyl groups of the following dicarboxylic acid to cyano groups by a known method to synthesize the compound A, and the compound A and the compound B are reacted.

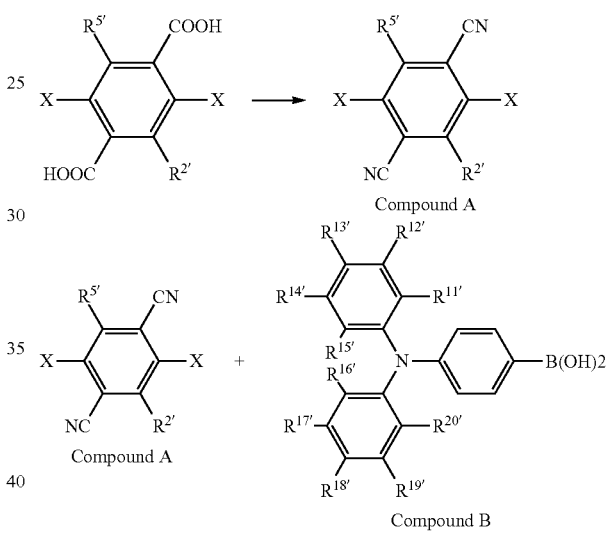

For the descriptions of $R^{2'}$, $R^{5'}$, and $R^{11'}$ to $R^{20'}$ in the aforementioned reaction scheme, reference may be made to the corresponding descriptions in the general formula (1'). X represents a halogen atom, examples of which include a fluorine atom, a chlorine atom, a bromine atom, and an iodine atom, and a chlorine atom, a bromine atom, and an iodine atom are preferred.

The reactions in the aforementioned scheme each are an application of the known reactions, and the known reaction conditions may be appropriately selected and used. For the details of the reactions, reference may be made to the synthesis examples described later. The compound represented by the general formula (1') may also be synthesized by combining the other known synthesis reactions.

Organic Light-Emitting Device

The compound represented by the general formula (1) of the invention is useful as a light-emitting material of an organic light-emitting device. Accordingly, the compound represented by the general formula (1) of the invention may be effectively used as a light-emitting material in a light-emitting layer of an organic light-emitting device. The compound represented by the general formula (1) includes a delayed fluorescent emitter emitting delayed fluorescent light. Thus, the invention provides an invention relating to a delayed fluorescent emitter having the structure represented by the general formula (1), an invention relating to the use of the compound represented by the general formula (1) as the delayed fluorescent emitter, and an invention relating to a method for emitting delayed fluorescent light with the compound represented by the general formula (1). An organic light-emitting device that uses the compound as a light-emitting material has features that the device emits delayed fluorescent light and has a high light emission efficiency. The principle of the features may be described as follows for an organic electroluminescent device as an example.

In an organic electroluminescent device, carriers are injected from an anode and a cathode to a light-emitting material to form an excited state for the light-emitting material, with which light is emitted. In the case of a carrier injection type organic electroluminescent device, in general, excitons that are excited to the excited singlet state are 25% of the total excitons generated, and the remaining 75% thereof are excited to the excited triplet state. Accordingly, the use of phosphorescence, which is light emission from the excited triplet state, provides a high energy utilization. However, the excited triplet state has a long lifetime and thus causes saturation of the excited state and deactivation of energy through mutual action with the excitons in the excited triplet state, and therefore the quantum yield of phosphorescence may generally be often not high. A delayed fluorescent material emits fluorescent light through the mechanism that the energy of excitons transits to the excited triplet state through intersystem crossing or the like, and then transits to the excited singlet state through reverse intersystem crossing due to triplet-triplet annihilation or absorption of thermal energy, thereby emitting fluorescent light. It is considered that among the materials, a thermal activation type delayed fluorescent material emitting light through absorption of thermal energy is particularly useful for an organic electroluminescent device. In the case where a delayed fluorescent material is used in an organic electroluminescent device, the excitons in the excited singlet state normally emit fluorescent light. On the other hand, the excitons in the excited triplet state emit fluorescent light through intersystem crossing to the excited singlet state by absorbing the heat generated by the device. At this time, the light emitted through reverse intersystem crossing from the excited triplet state to the excited singlet state has the same wavelength as fluorescent light since it is light emission from the excited singlet state, but has a longer lifetime (light emission lifetime) than the normal fluorescent light and phosphorescent light, and thus the light is observed as fluorescent light that is delayed from the normal fluorescent light and phosphorescent light. The light may be defined as delayed fluorescent light. The use of the thermal activation type exciton transition mechanism may raise the proportion of the compound in the excited singlet state, which is generally formed in a proportion only of 25%, to 25% or more through the absorption of the thermal energy after the carrier injection. A compound that emits strong fluorescent light and delayed fluorescent light at a low temperature of lower than 100° C. undergoes the intersystem crossing from the excited triplet state to the excited singlet state sufficiently with the heat of the device, thereby emitting delayed fluorescent light, and thus the use of the compound may drastically enhance the light emission efficiency (photoluminescence quantum efficiency, electroluminescence quantum efficiency or the both).

The use of the compound represented by the general formula (1) of the invention as a light-emitting material of a light-emitting layer may provide an excellent organic light-emitting device, such as an organic photoluminescent device (organic PL device) and an organic electroluminescent device (organic EL device). At this time, the compound represented by the general formula (1) of the invention may have a function of assisting light emission of another light-emitting material contained in the light-emitting layer, i.e., as a so-called assist dopant. Specifically, the compound represented by the general formula (1) of the invention contained in the light-emitting layer may have a lowest excited singlet energy level that is between the lowest excited singlet energy level of the host material contained in the light-emitting layer and the lowest excited singlet energy level of the another light-emitting material contained in the light-emitting layer.

The organic photoluminescent device has a structure containing a substrate having formed thereon at least a light-emitting layer. The organic electroluminescent device has a structure containing at least an anode, a cathode and an organic layer formed between the anode and the cathode. The organic layer contains at least a light-emitting layer, and may be formed only of a light-emitting layer, or may have one or more organic layer in addition to the light-emitting layer. Examples of the organic layer include a hole transporting layer, a hole injection layer, an electron barrier layer, a hole barrier layer, an electron injection layer, an electron transporting layer and an exciton barrier layer. The hole transporting layer may be a hole injection and transporting layer having a hole injection function, and the electron transporting layer may be an electron injection and transporting layer having an electron injection function. A specific structural example of an organic electroluminescent device is shown in FIG. 1. In FIG. 1, the numeral 1 denotes a substrate, 2 denotes an anode, 3 denotes a hole injection layer, 4 denotes a hole transporting layer, 5 denotes a light-emitting layer, 6 denotes an electron transporting layer, and 7 denotes a cathode.

The members and the layers of the organic electroluminescent device will be described below. The descriptions for the substrate and the light-emitting layer may also be applied to the substrate and the light-emitting layer of the organic photoluminescent device.

Substrate

The organic electroluminescent device of the invention is preferably supported by a substrate. The substrate is not particularly limited and may be those that have been commonly used in an organic electroluminescent device, and examples thereof used include those formed of glass, transparent plastics, quartz and silicon.

Anode

The anode of the organic electroluminescent device used is preferably formed of as an electrode material a metal, an alloy or an electroconductive compound each having a large work function (4 eV or more), or a mixture thereof. Specific examples of the electrode material include a metal, such as Au, and an electroconductive transparent material, such as CuI, indium tin oxide (ITO), $SnO_2$ and ZnO. A material that is amorphous and is capable of forming a transparent electroconductive film, such as IDIXO ($In_2O_3$—ZnO), may also be used. The anode may be formed in such a manner that the electrode material is formed into a thin film by such a method as vapor deposition or sputtering, and the film is patterned into a desired pattern by a photolithography method, or in the case where the pattern may not require high accuracy (for example, approximately 100 μm or more), the pattern may be formed with a mask having a desired shape on vapor deposition or sputtering of the electrode material. In alternative, in the case where a material capable of being applied as a coating, such as an organic electroconductive compound, is used, a wet film forming method, such as a printing method and a coating method, may be used. In the case where emitted light is to be taken out through the anode, the anode preferably has a transmittance of more than 10%, and the anode preferably has a sheet resistance of several hundred Ohm per square or less. The thickness thereof may be generally selected from a range of from 10 to 1,000 nm, and preferably from 10 to 200 nm, while depending on the material used.

Cathode

The cathode is preferably formed of as an electrode material a metal having a small work function (4 eV or less) (referred to as an electron injection metal), an alloy or an electroconductive compound each having a small work function (4 eV or less), or a mixture thereof. Specific examples of the electrode material include sodium, a sodium-potassium alloy, magnesium, lithium, a magnesium-cupper mixture, a magnesium-silver mixture, a magnesium-aluminum mixture, a magnesium-indium mixture, an aluminum-aluminum oxide ($Al_2O_3$) mixture, indium, a lithium-aluminum mixture, and a rare earth metal. Among these, a mixture of an electron injection metal and a second metal that is a stable metal having a larger work function than the electron injection metal, for example, a magnesium-silver mixture, a magnesium-aluminum mixture, a magnesium-indium mixture, an aluminum-aluminum oxide ($Al_2O_3$) mixture, a lithium-aluminum mixture, and aluminum, are preferred from the standpoint of the electron injection property and the durability against oxidation and the like. The cathode may be produced by forming the electrode material into a thin film by such a method as vapor deposition or sputtering. The cathode preferably has a sheet resistance of several hundred Ohm per square or less, and the thickness thereof may be generally selected from a range of from 10 nm to 5 µm, and preferably from 50 to 200 nm. For transmitting the emitted light, any one of the anode and the cathode of the organic electroluminescent device is preferably transparent or translucent, thereby enhancing the light emission luminance.

The cathode may be formed with the electroconductive transparent materials described for the anode, thereby forming a transparent or translucent cathode, and by applying the cathode, a device having an anode and a cathode, both of which have transmittance, may be produced.

Light-Emitting Layer

The light-emitting layer is a layer, in which holes and electrons injected from the anode and the cathode, respectively, are recombined to form excitons, and then the layer emits light. A light-emitting material may be solely used as the light-emitting layer, but the light-emitting layer preferably contains a light-emitting material and a host material. The light-emitting material used may be one kind or two or more kinds selected from the group of compounds represented by the general formula (1) of the invention. In order that the organic electroluminescent device and the organic photoluminescent device of the invention exhibit a high light emission efficiency, it is important that the singlet excitons and the triplet excitons generated in the light-emitting material are confined in the light-emitting material. Accordingly, a host material is preferably used in addition to the light-emitting material in the light-emitting layer. The host material used may be an organic compound that has excited singlet energy and excited triplet energy, at least one of which is higher than those of the light-emitting material of the invention. As a result, the singlet excitons and the triplet excitons generated in the light-emitting material of the invention are capable of being confined in the molecules of the light-emitting material of the invention, thereby eliciting the light emission efficiency thereof sufficiently. Even though the singlet excitons and the triplet excitons are not confined sufficiently, a high light emission efficiency may be obtained in some cases, and thus a host material that is capable of achieving a high light emission efficiency may be used in the invention without any particular limitation. In the organic light-emitting device and the organic electroluminescent device of the invention, the light emission occurs in the light-emitting material of the invention contained in the light-emitting layer. The emitted light contains both fluorescent light and delayed fluorescent light. However, a part of the emitted light may contain emitted light from the host material, or the emitted light may partially contain emitted light from the host material.

In the case where the host material is used, the amount of the compound of the invention as the light-emitting material contained in the light-emitting layer is preferably 0.1% by weight or more, and more preferably 1% by weight or more, and is preferably 50% by weight or less, more preferably 20% by weight or less, and further preferably 10% by weight or less.

The host material in the light-emitting layer is preferably an organic compound that has a hole transporting function and an electron transporting function, prevents the emitted light from being increased in wavelength, and has a high glass transition temperature.

Injection Layer

The injection layer is a layer that is provided between the electrode and the organic layer, for decreasing the driving voltage and enhancing the light emission luminance, and includes a hole injection layer and an electron injection layer, which may be provided between the anode and the light-emitting layer or the hole transporting layer and between the cathode and the light-emitting layer or the electron transporting layer. The injection layer may be provided depending on necessity.

Barrier Layer

The barrier layer is a layer that is capable of inhibiting charges (electrons or holes) and/or excitons present in the light-emitting layer from being diffused outside the light-emitting layer. The electron barrier layer may be disposed between the light-emitting layer and the hole transporting layer, and inhibits electrons from passing through the light-emitting layer toward the hole transporting layer. Similarly, the hole barrier layer may be disposed between the light-emitting layer and the electron transporting layer, and inhibits holes from passing through the light-emitting layer toward the electron transporting layer. The barrier layer may also be used for inhibiting excitons from being diffused outside the light-emitting layer. Thus, the electron barrier layer and the hole barrier layer each may also have a function as an exciton barrier layer. The term "the electron barrier layer" or "the exciton barrier layer" referred herein is intended to include a layer that has both the functions of an electron barrier layer and an exciton barrier layer by one layer.

Hole Barrier Layer

The hole barrier layer has the function of an electron transporting layer in a broad sense. The hole barrier layer has a function of inhibiting holes from reaching the electron transporting layer while transporting electrons, and thereby enhances the recombination probability of electrons and holes in the light-emitting layer. As the material for the hole barrier layer, the materials for the electron transporting layer described later may be used depending on necessity.

Electron Barrier Layer

The electron barrier layer has the function of transporting holes in abroad sense. The electron barrier layer has a function of inhibiting electrons from reaching the hole transporting layer while transporting holes, and thereby enhances the recombination probability of electrons and holes in the light-emitting layer.

Exciton Barrier Layer

The exciton barrier layer is a layer for inhibiting excitons generated through recombination of holes and electrons in the light-emitting layer from being diffused to the charge transporting layer, and the use of the layer inserted enables effective confinement of excitons in the light-emitting layer, and thereby enhances the light emission efficiency of the device. The exciton barrier layer may be inserted adjacent to the light-emitting layer on any of the side of the anode and the side of the cathode, and on both the sides. Specifically, in the case where the exciton barrier layer is present on the side of the anode, the layer may be inserted between the hole transporting layer and the light-emitting layer and adjacent to the light-emitting layer, and in the case where the layer is inserted on the side of the cathode, the layer may be inserted between the light-emitting layer and the cathode and adjacent to the light-emitting layer. Between the anode and the exciton barrier layer that is adjacent to the light-emitting layer on the side of the anode, a hole injection layer, an electron barrier layer and the like may be provided, and between the cathode and the exciton barrier layer that is adjacent to the light-emitting layer on the side of the cathode, an electron injection layer, an electron transporting layer, a hole barrier layer and the like may be provided. In the case where the barrier layer is provided, the material used for the barrier layer preferably has excited singlet energy and excited triplet energy, at least one of which is higher than the excited singlet energy and the excited triplet energy of the light-emitting layer, respectively.

Hole Transporting Layer

The hole transporting layer is formed of a hole transporting material having a function of transporting holes, and the hole transporting layer may be provided as a single layer or plural layers.

The hole transporting material has one of injection or transporting property of holes and barrier property of electrons, and may be any of an organic material and an inorganic material. Examples of known hole transporting materials that may be used herein include a triazole derivative, an oxadiazole derivative, an imidazole derivative, a carbazole derivative, an indolocarbazole derivative, a polyarylalkane derivative, a pyrazoline derivative, a pyrazolone derivative, a phenylenediamine derivative, an arylamine derivative, an amino-substituted chalcone derivative, an oxazole derivative, a styrylanthracene derivative, a fluorenone derivative, a hydrazone derivative, a stilbene derivative, a silazane derivative, an aniline copolymer and an electroconductive polymer oligomer, particularly a thiophene oligomer. Among these, a porphyrin compound, an aromatic tertiary amine compound and a styrylamine compound are preferably used, and an aromatic tertiary amine compound is more preferably used.

Electron Transporting Layer

The electron transporting layer is formed of a material having a function of transporting electrons, and the electron transporting layer may be provided as a single layer or plural layers.

The electron transporting material (which may also function as a hole barrier material in some cases) needs only to have a function of transporting electrons, which are injected from the cathode, to the light-emitting layer. Examples of the electron transporting layer that may be used herein include a nitro-substituted fluorene derivative, a diphenylquinone derivative, a thiopyran dioxide derivative, carbodiimide, a fluorenylidene methane derivative, anthraquinodimethane and anthrone derivatives, and an oxadiazole derivative. The electron transporting material used may be a thiadiazole derivative obtained by replacing the oxygen atom of the oxadiazole ring of the oxadiazole derivative by a sulfur atom, or a quinoxaline derivative having a quinoxaline ring, which is known as an electron attracting group. Furthermore, polymer materials having these materials introduced to the polymer chain or having these materials used as the main chain of the polymer may also be used.

In the production of the organic electroluminescent device, the compound represented by the general formula (1) may be used not only in the light-emitting layer but also in the other layers than the light-emitting layer. In this case, the compound represented by the general formula (1) used in the light-emitting layer and the compound represented by the general formula (1) used in the other layers than the light-emitting layer may be the same as or different from each other. For example, the compound represented by the general formula (1) may be used in the injection layer, the barrier layer, the hole barrier layer, the electron barrier layer, the exciton barrier layer, the hole transporting layer, the electron transporting layer and the like described above. The film forming method of the layers are not particularly limited, and the layers may be produced by any of a dry process and a wet process.

Specific examples of preferred materials that may be used in the organic electroluminescent device are shown below, but the materials that may be used in the invention are not construed as being limited to the example compounds. The compound that is shown as a material having a particular function may also be used as a material having another function. In the structural formulae of the example compounds, R and $R_2$ to $R_7$ each independently represent a hydrogen atom or a substituent, and n represents an integer of from 3 to 5.

Preferred examples of a compound that may also be used as the host material of the light-emitting layer are shown below.

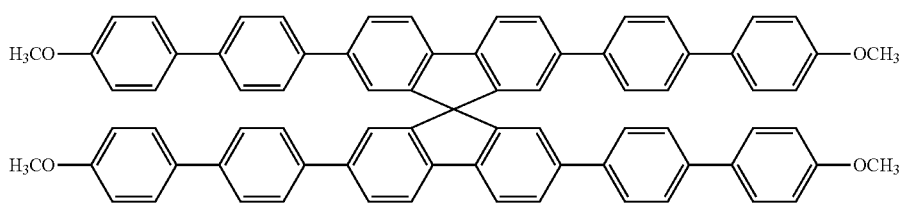

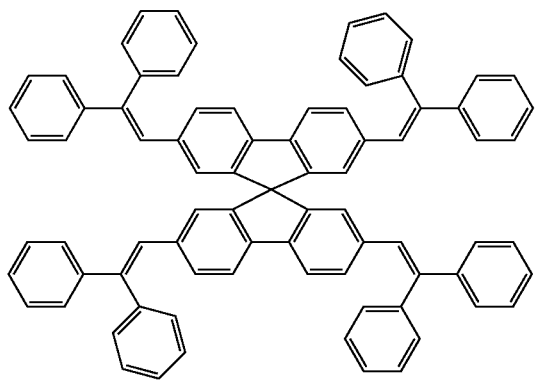
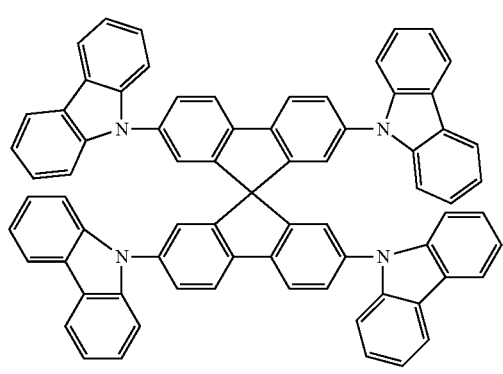
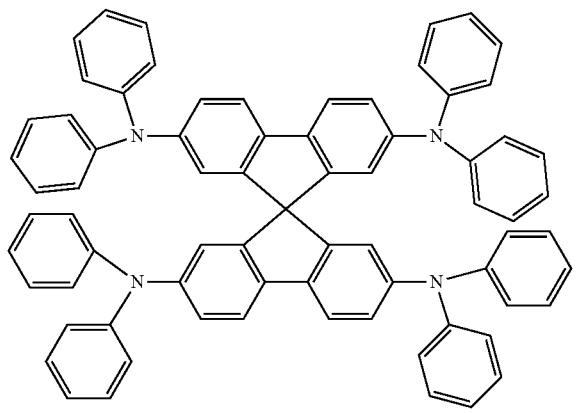
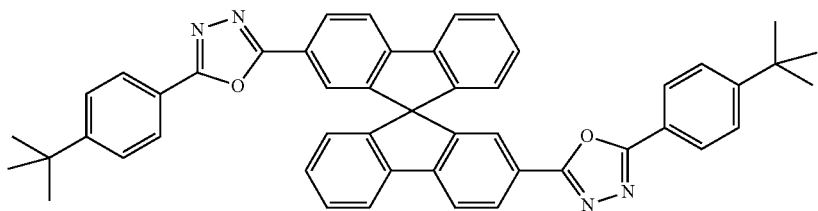
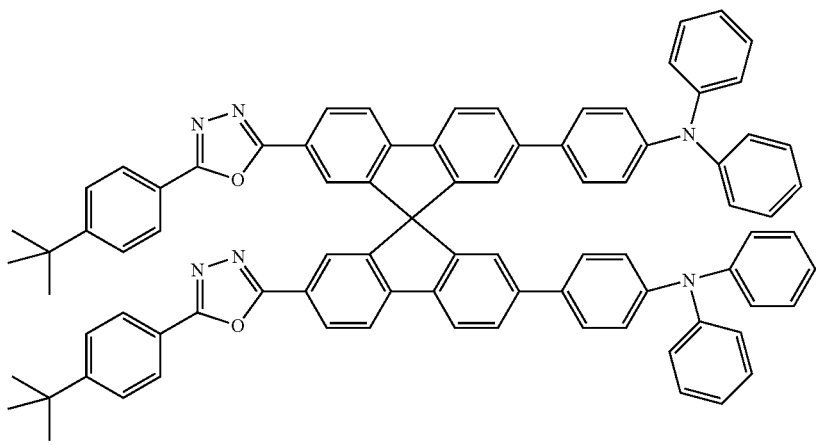
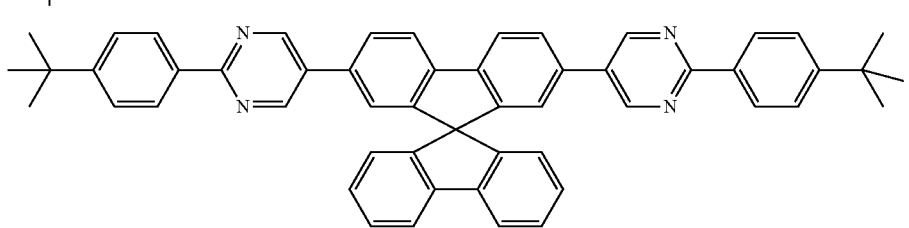

-continued
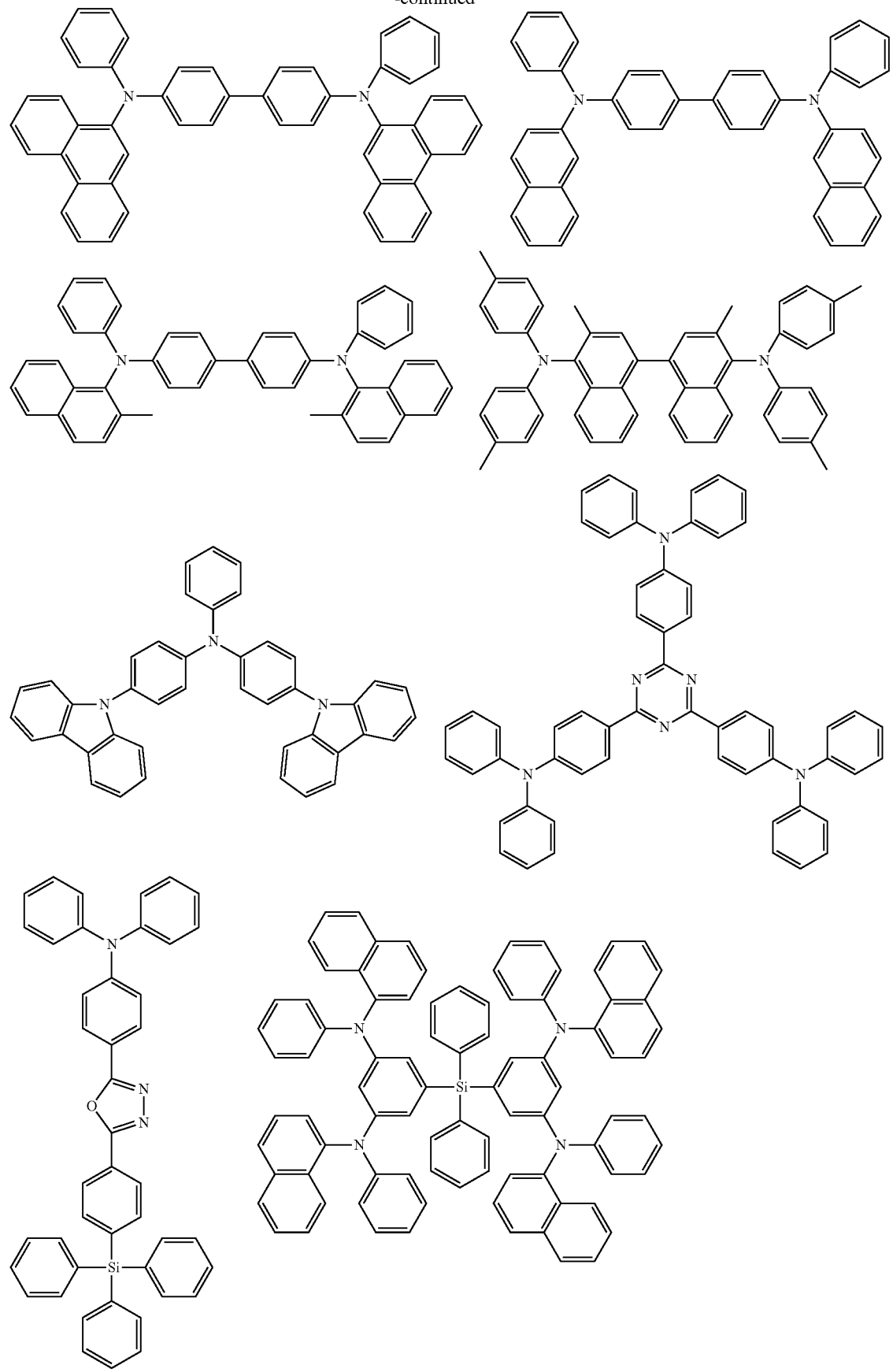

-continued
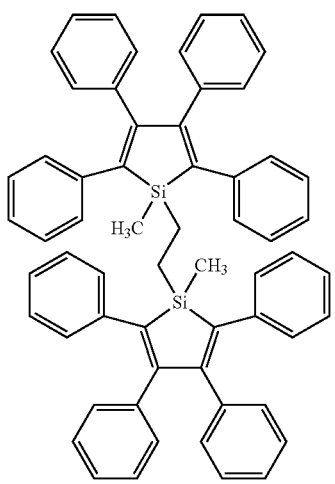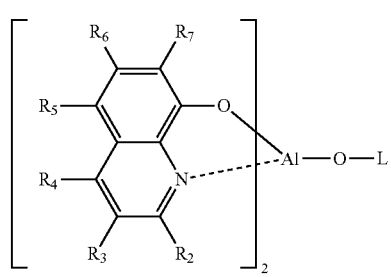
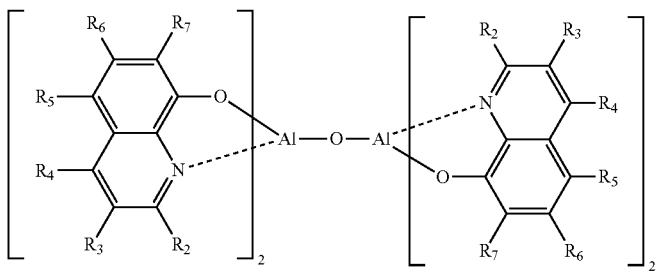
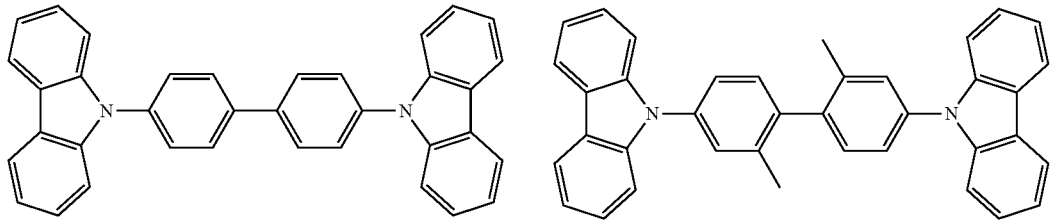
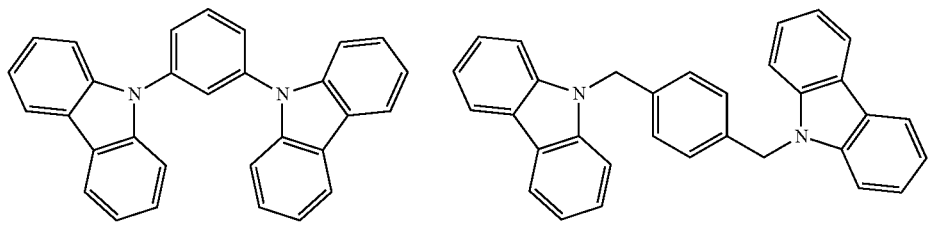
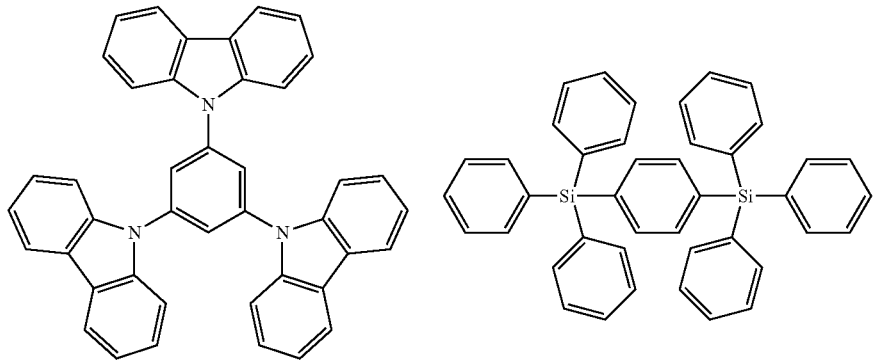

-continued
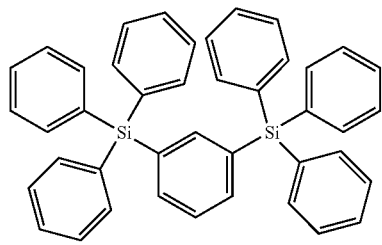
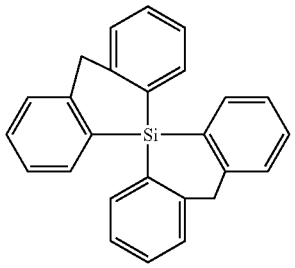
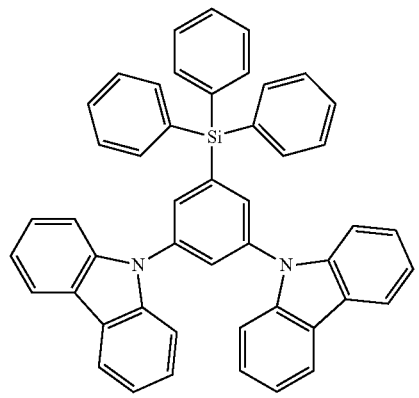
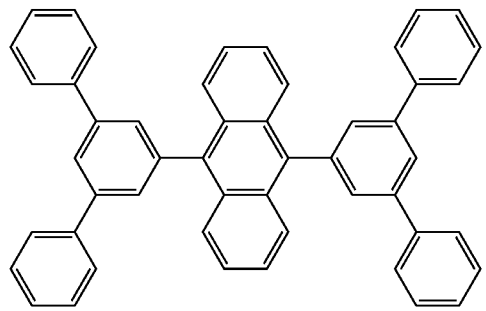
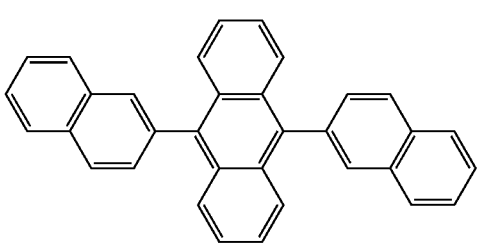
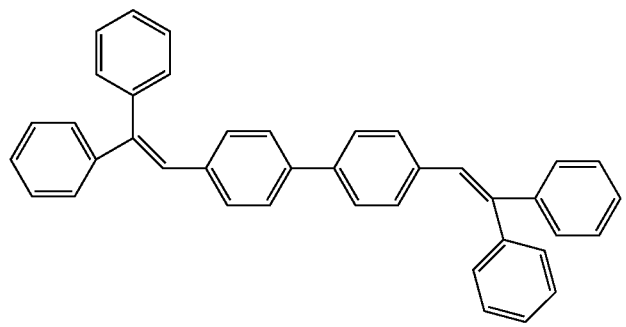
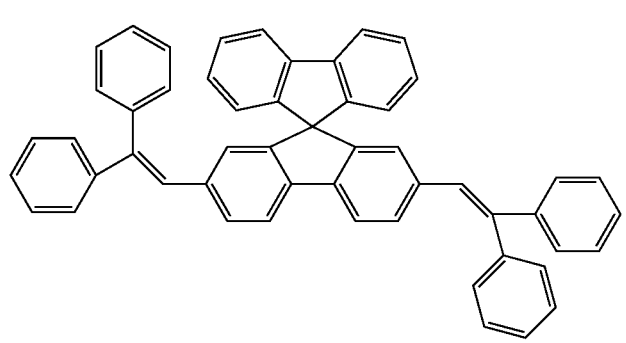
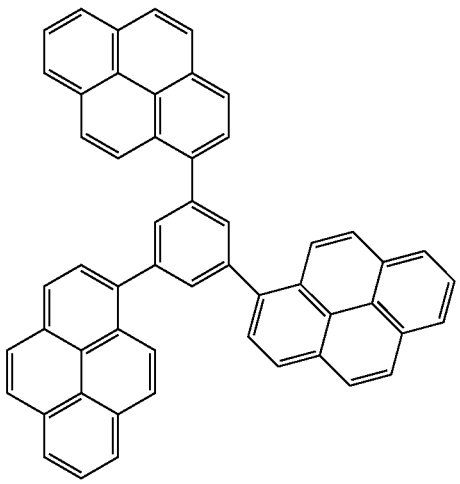

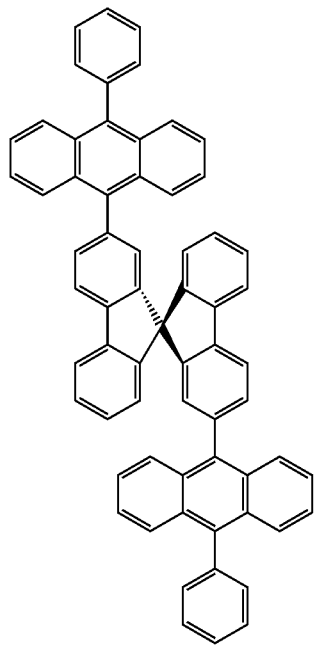
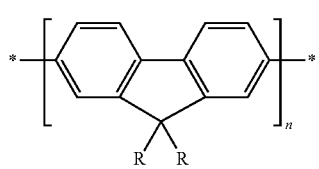
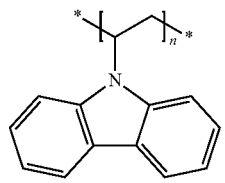
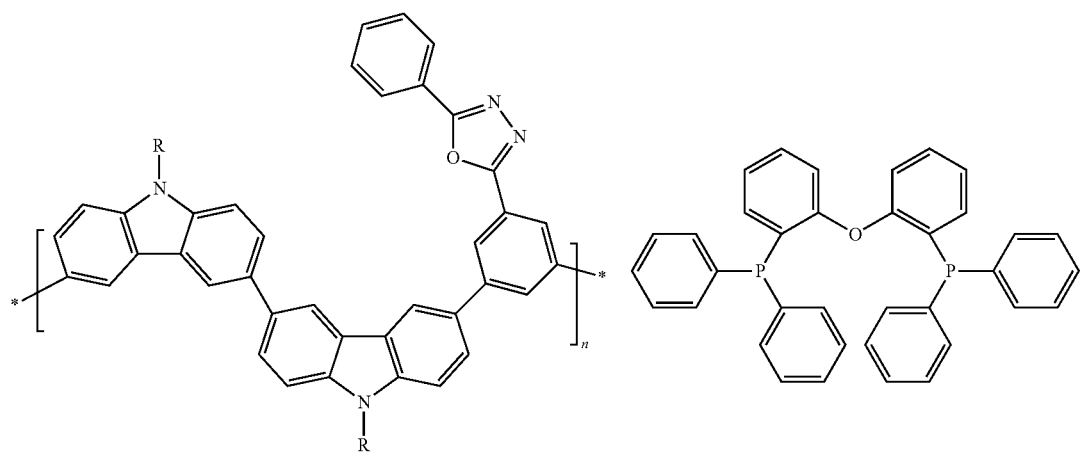
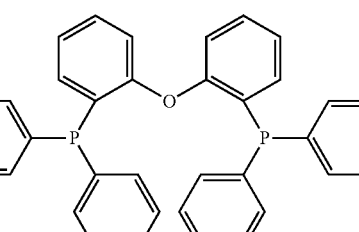
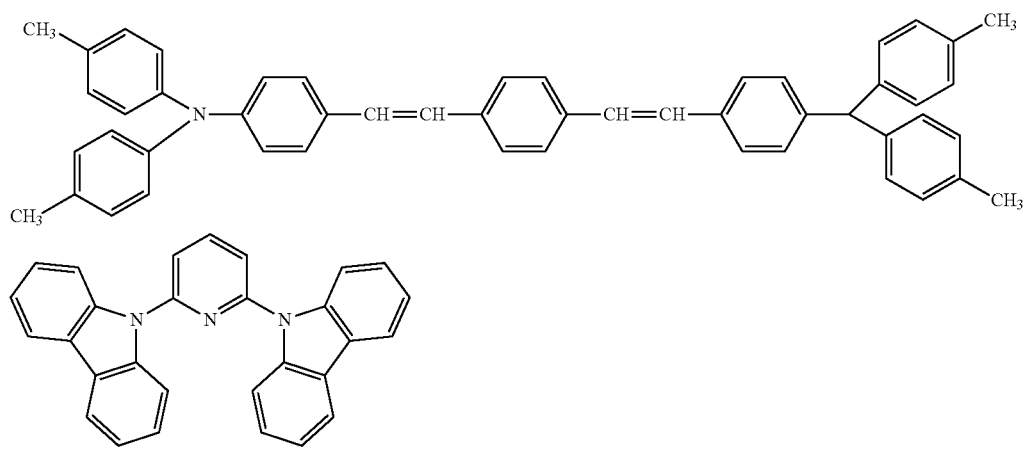
Preferred examples of a compound that may be used as the hole injection material are shown below.

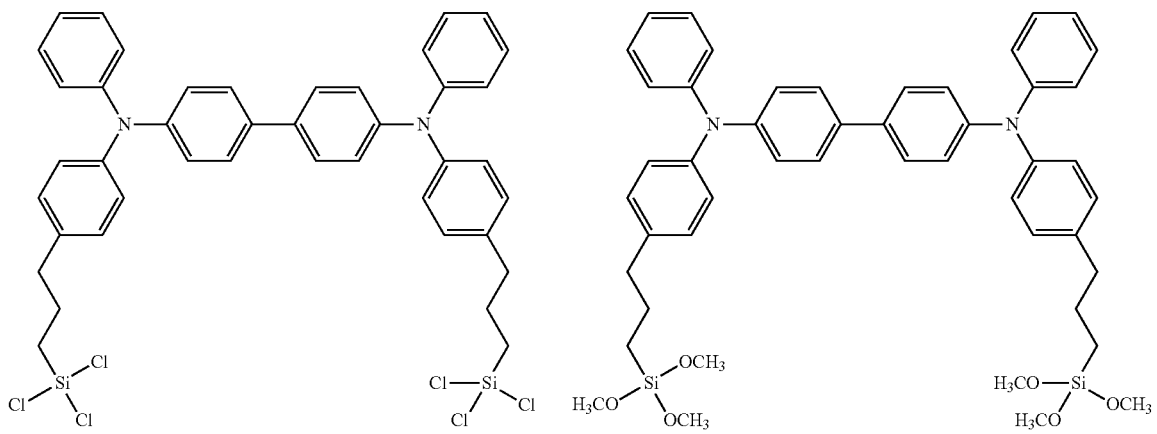
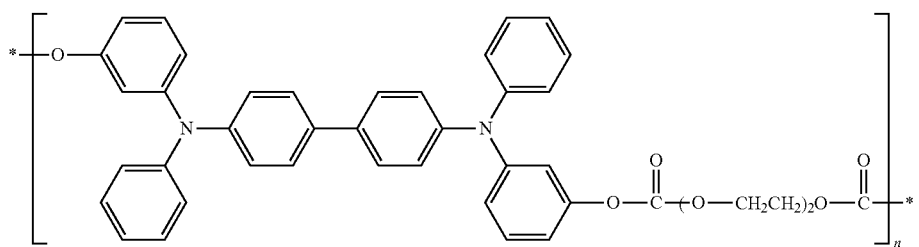
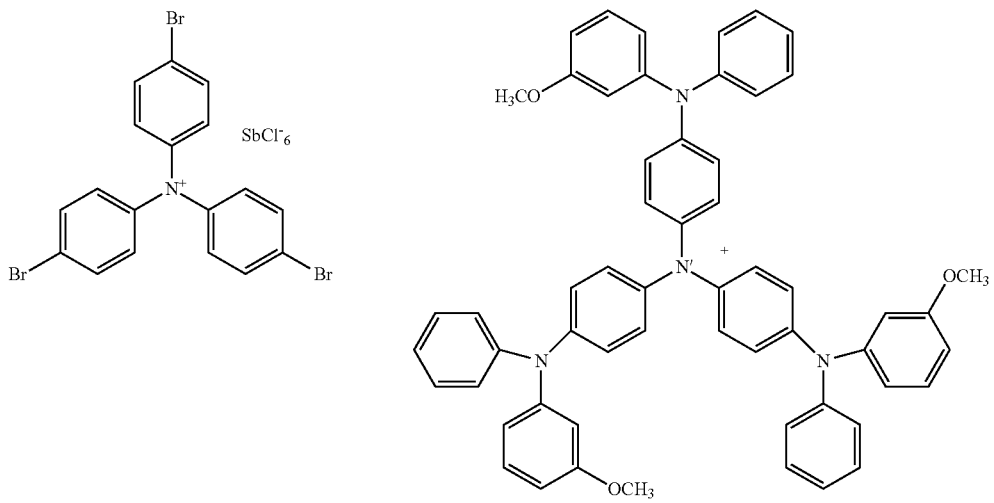
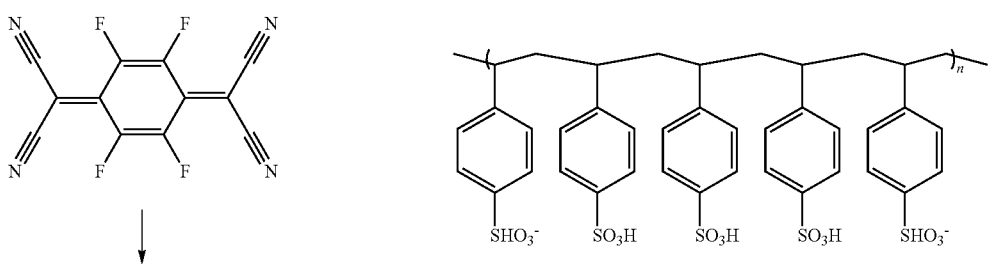
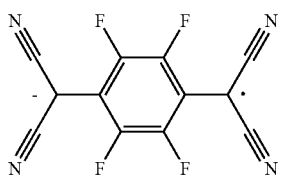

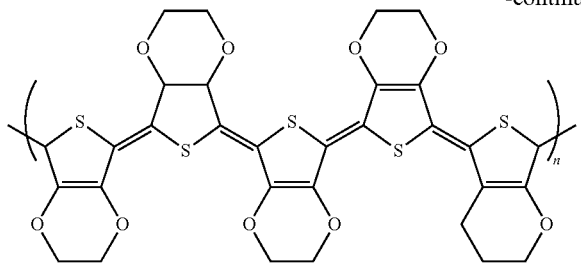
Preferred examples of a compound that may be used as the hole transporting material are shown below.
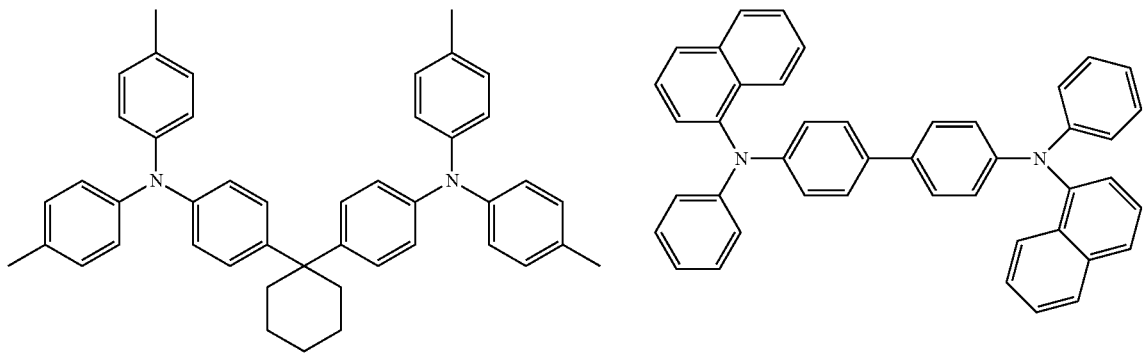
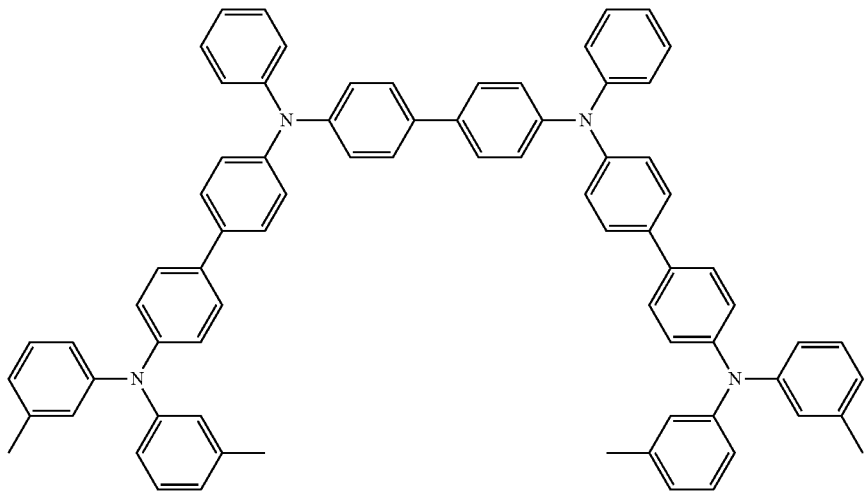
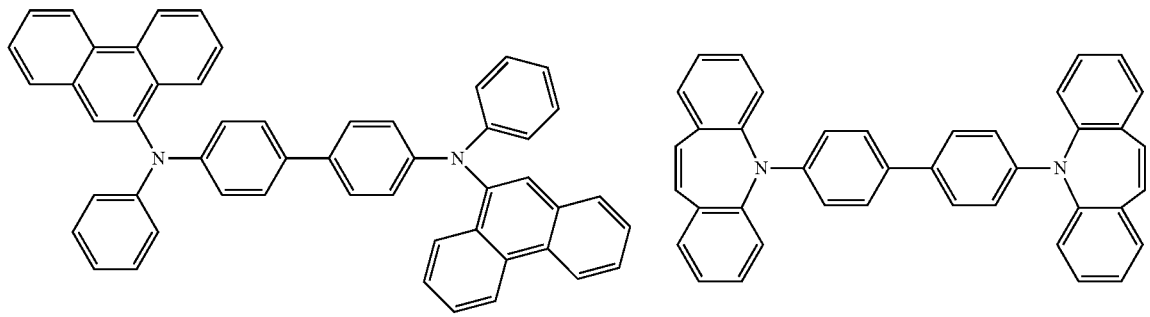

53
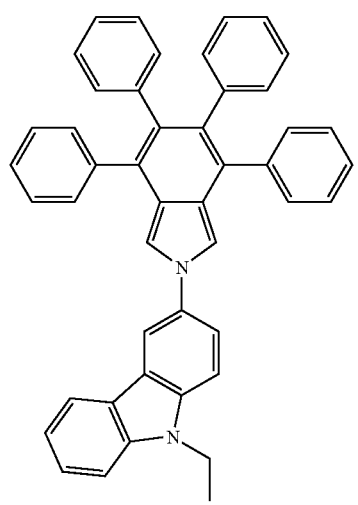
54
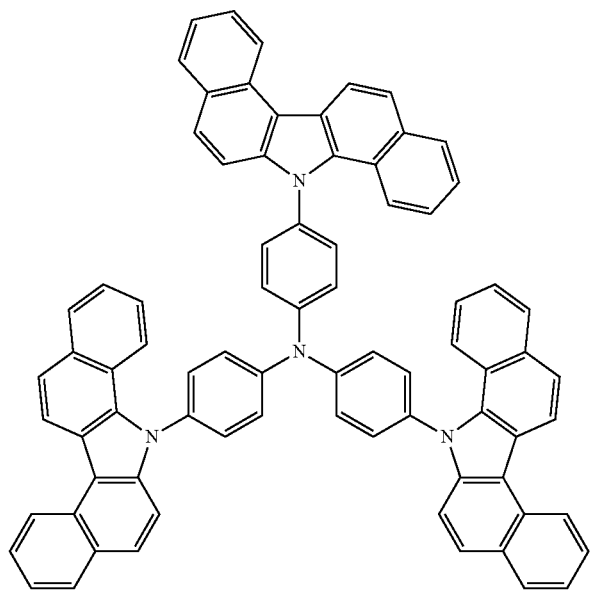
-continued
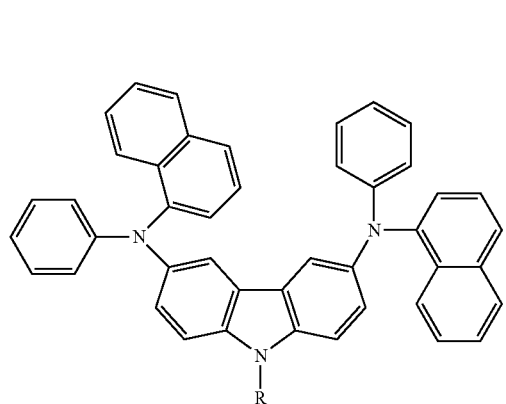
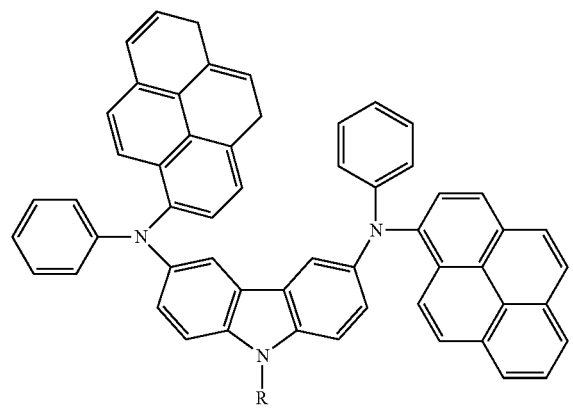
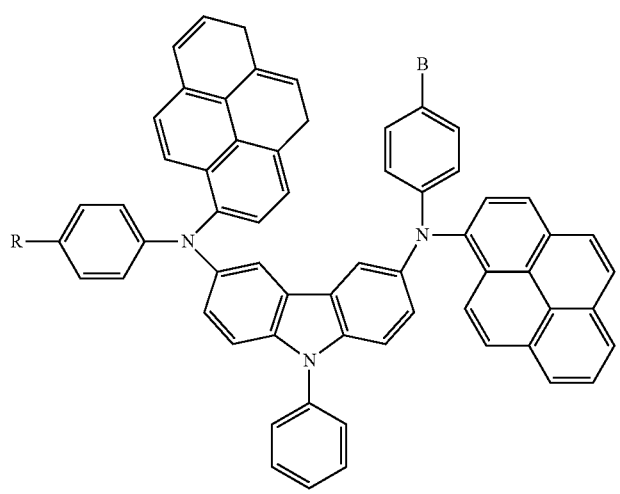

-continued
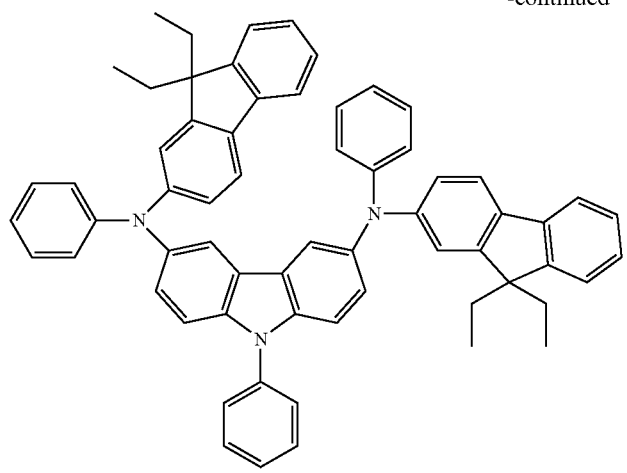
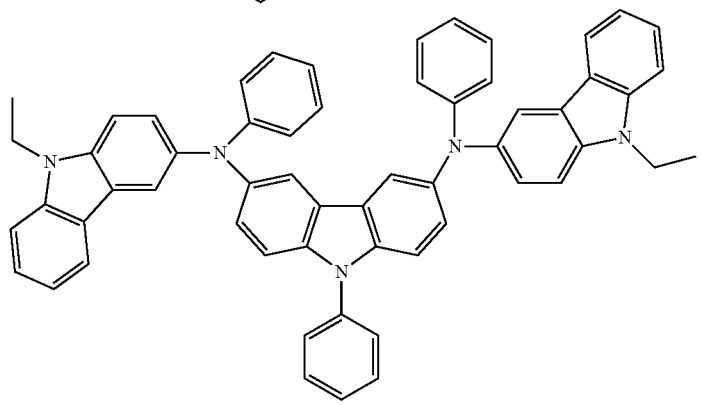
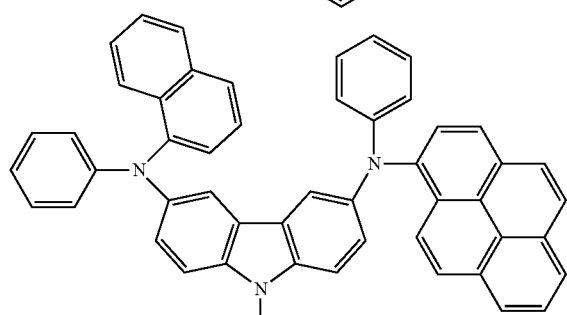
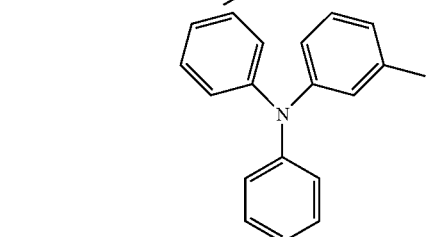
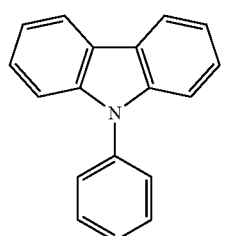
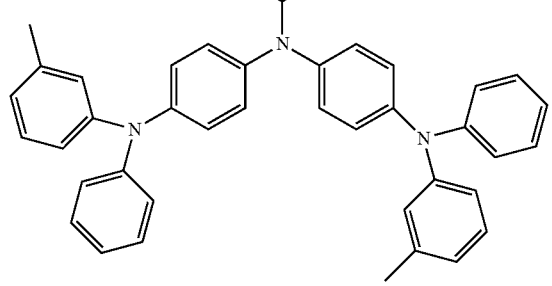
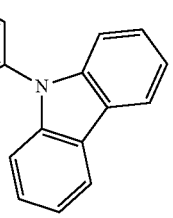

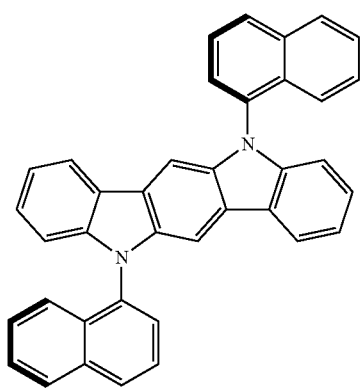
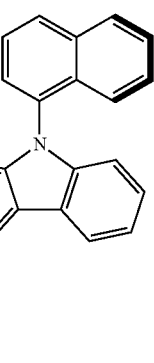
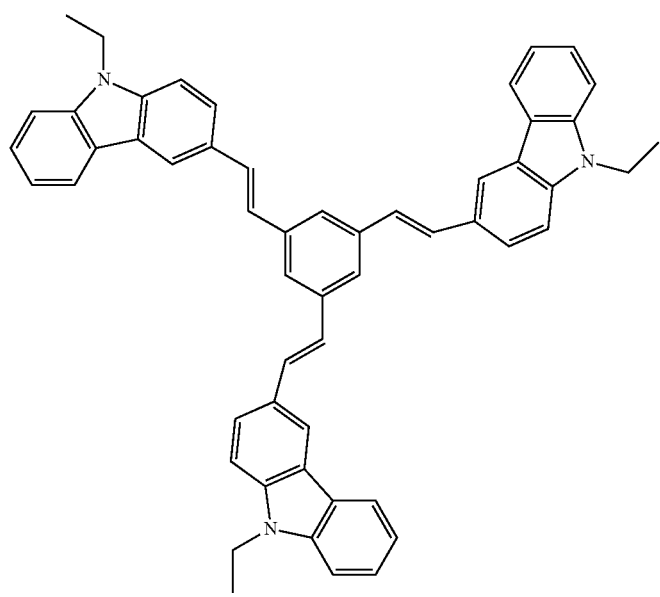
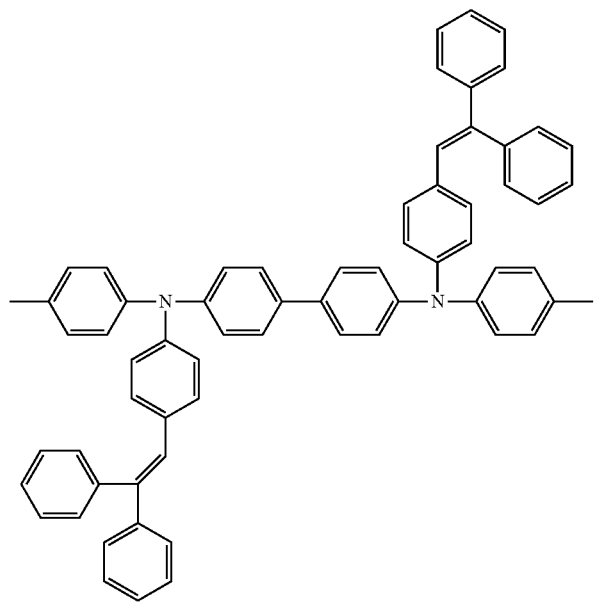
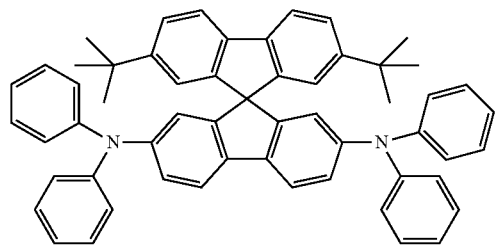

-continued
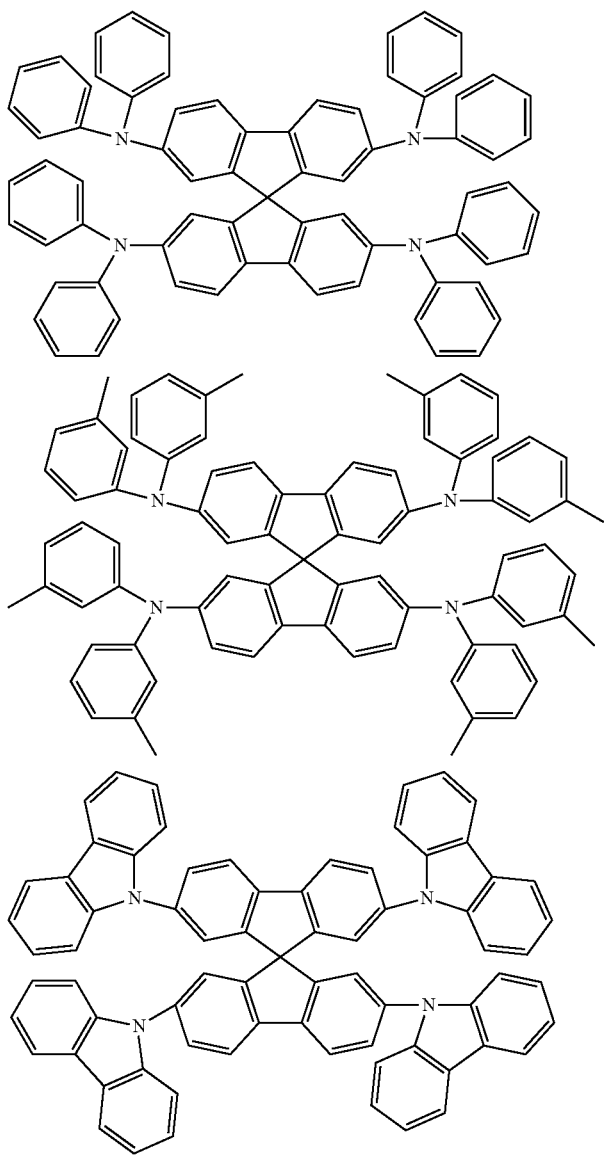
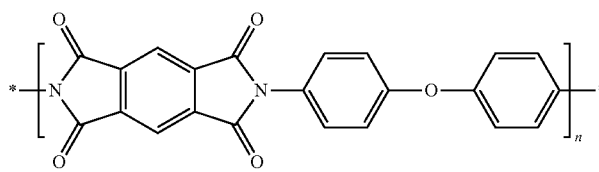
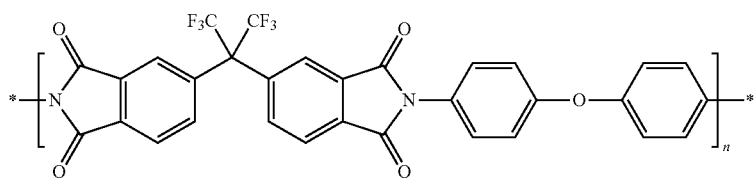
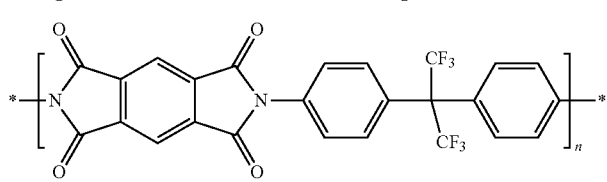

-continued
61 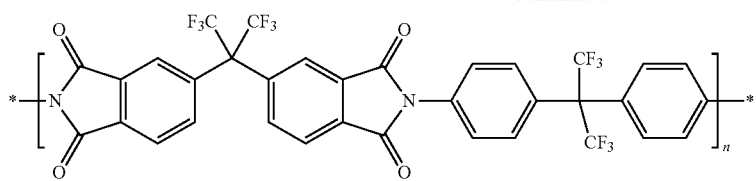
62 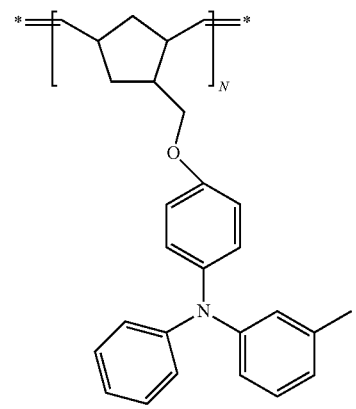
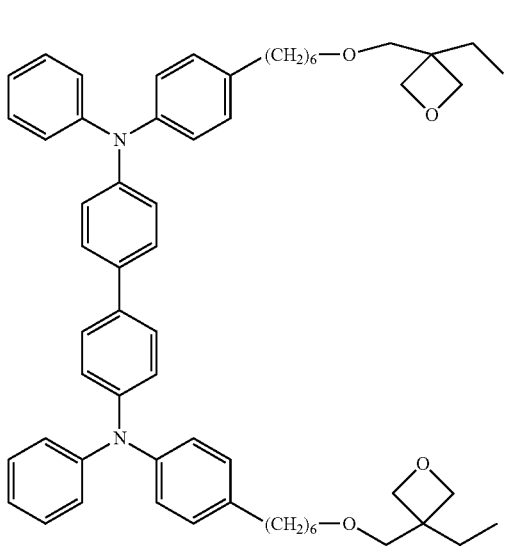
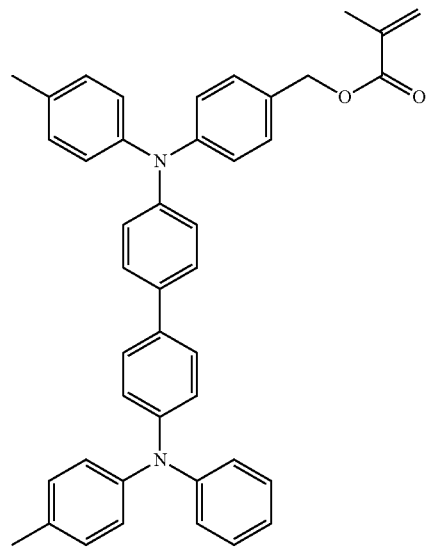
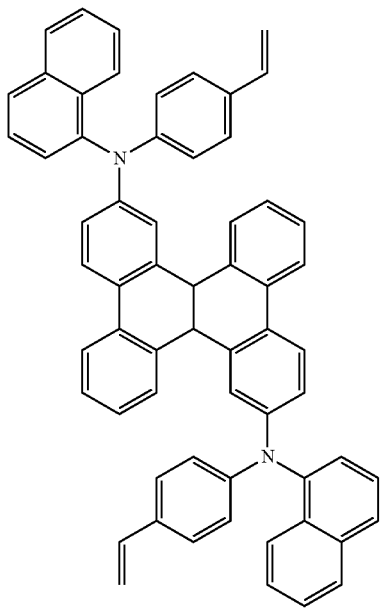
R = 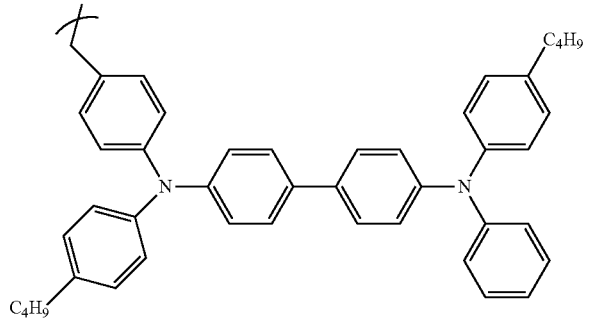

-continued
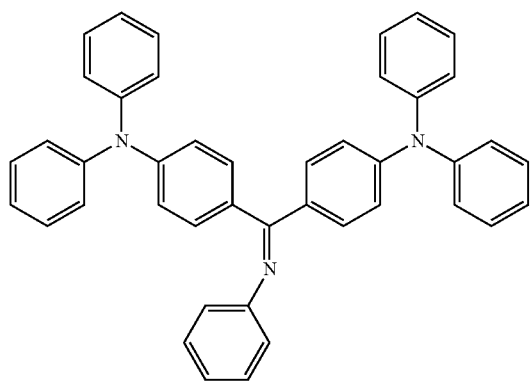
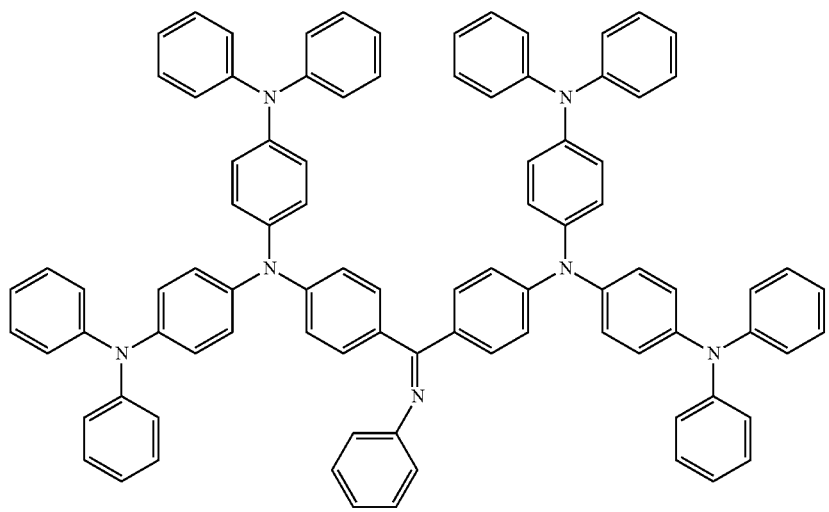
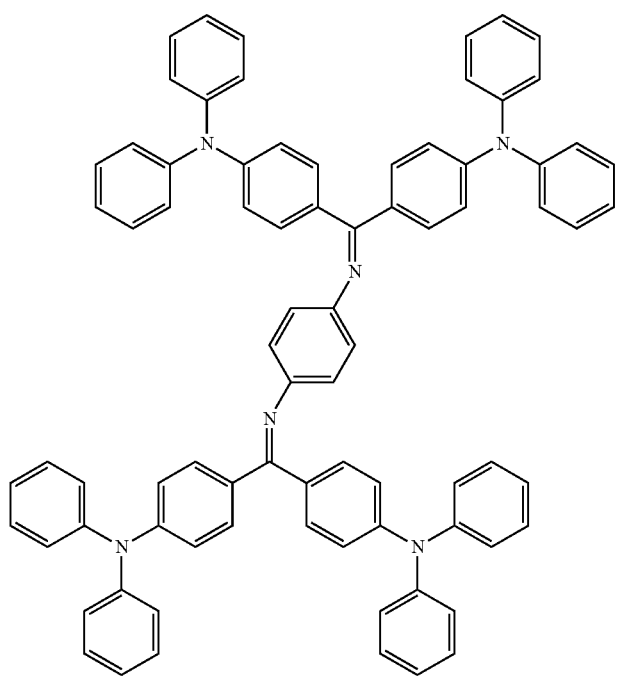

-continued
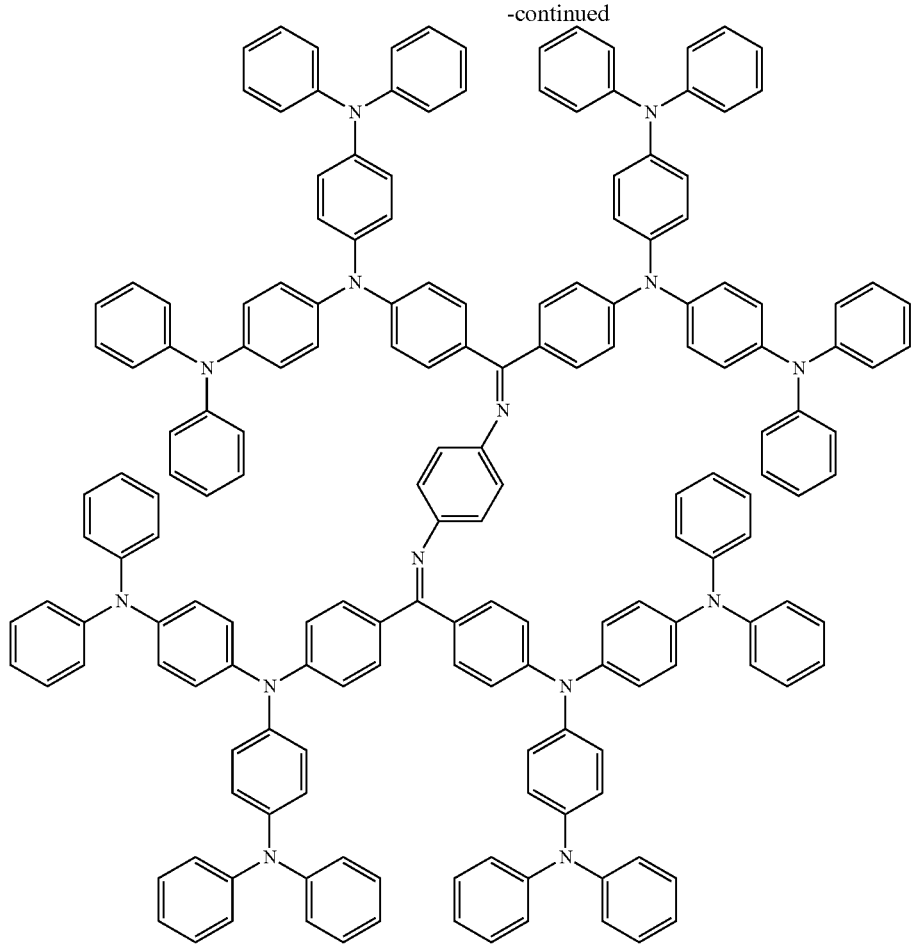
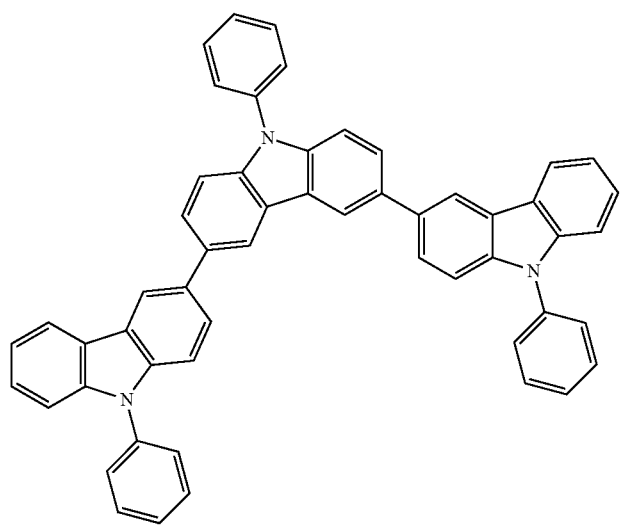
Preferred examples of a compound that may be used as the electron barrier material are shown below.

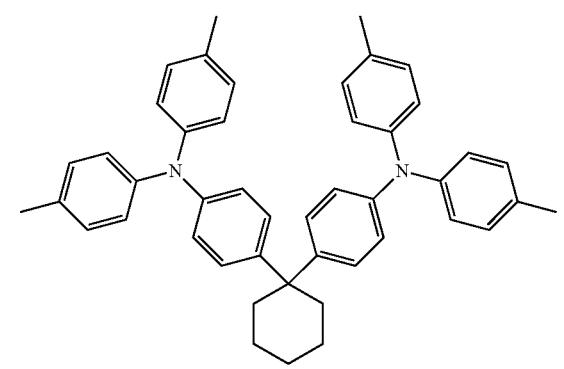
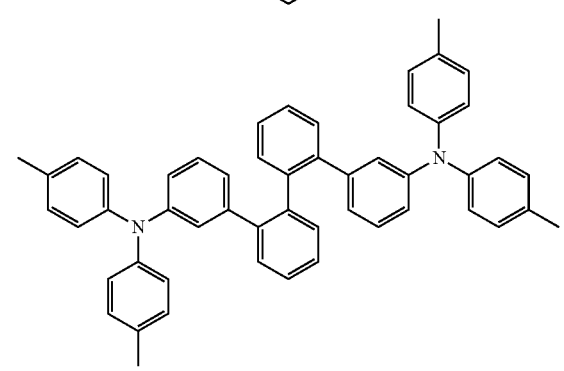
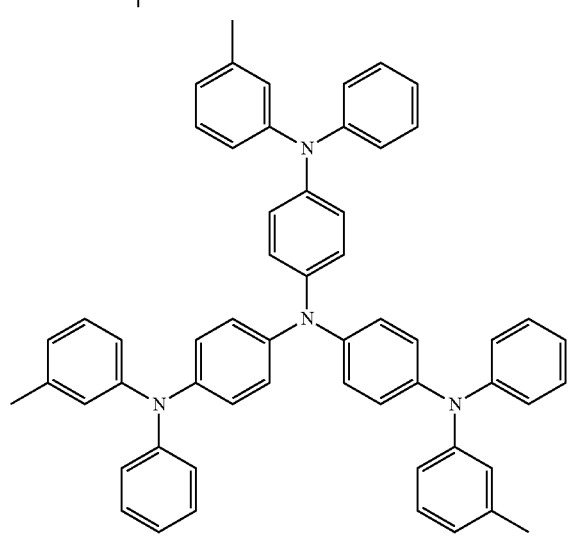
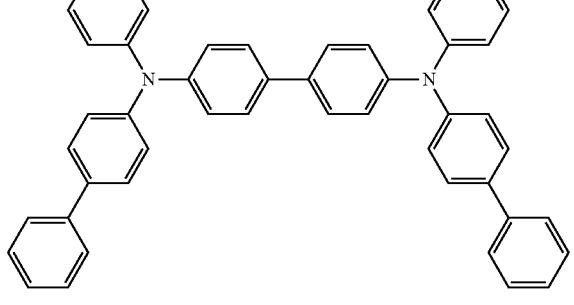
Preferred examples of a compound that may be used as the hole barrier material are shown below.
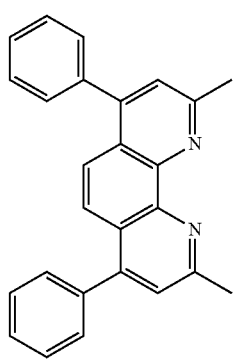
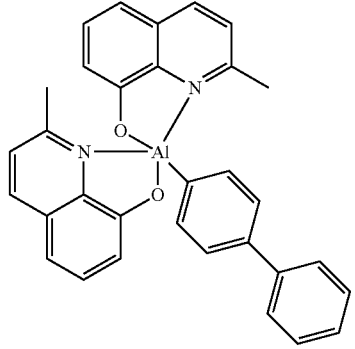
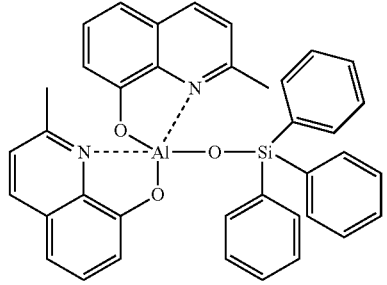

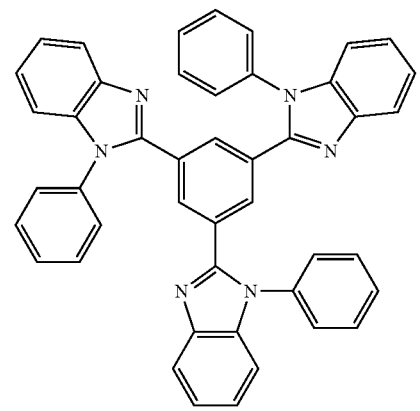
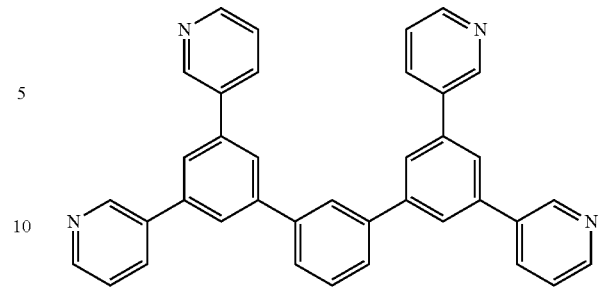
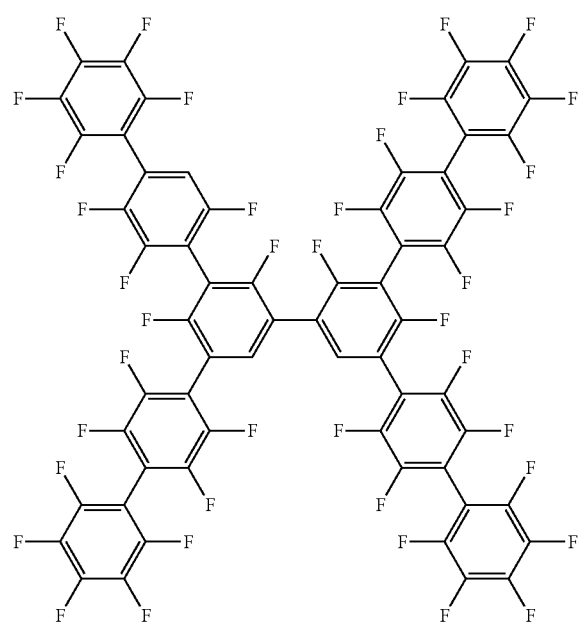
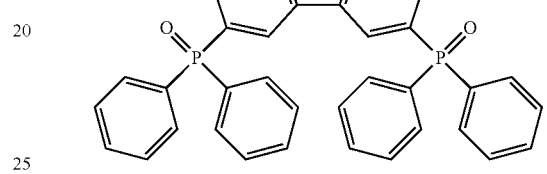
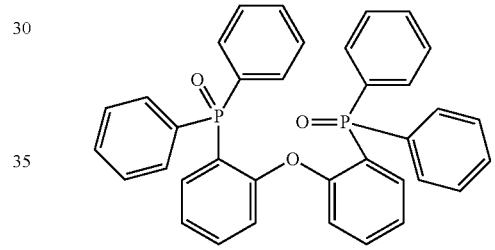
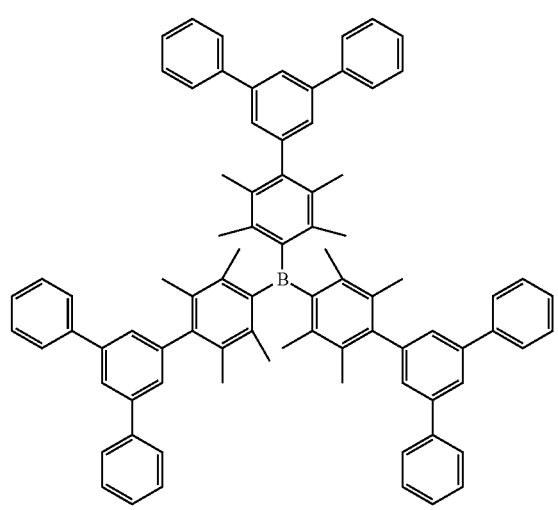
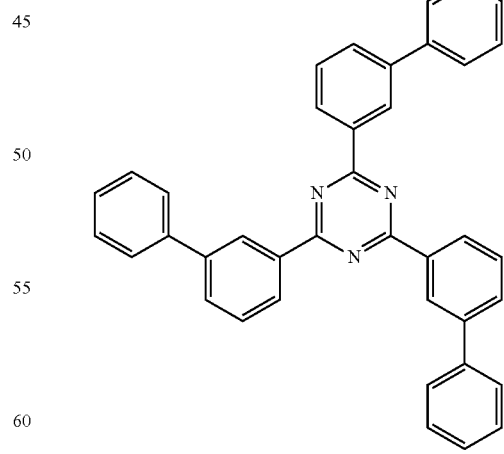
Preferred examples of a compound that may be used as the electron transporting material are shown below.

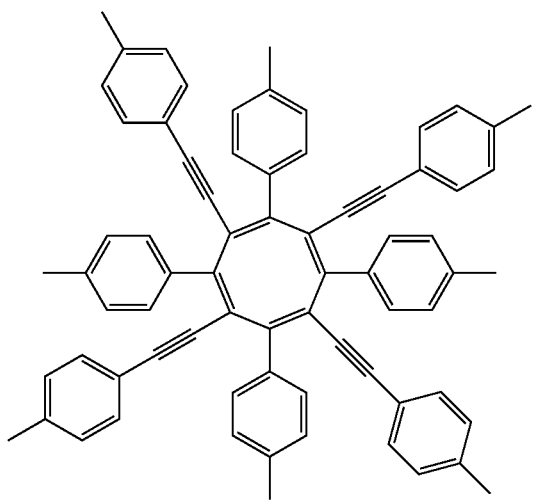
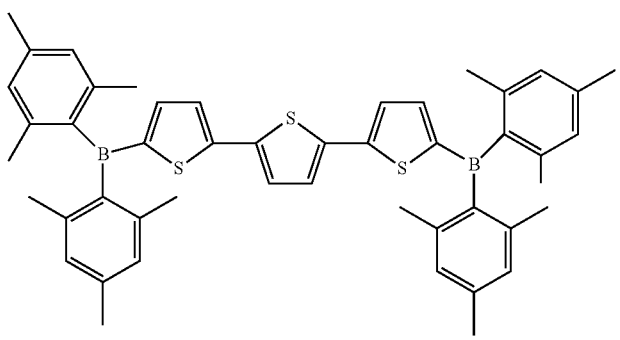
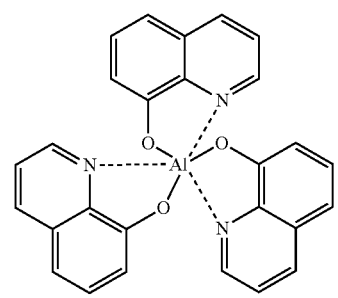
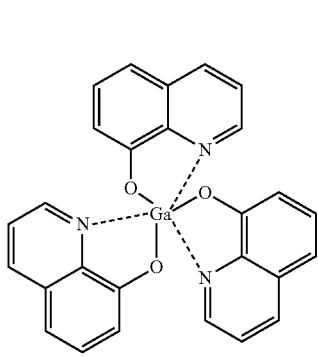
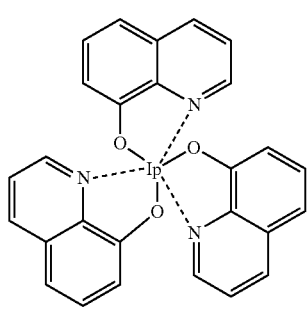
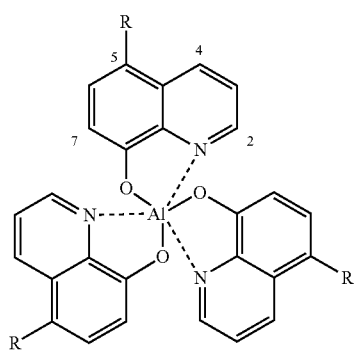
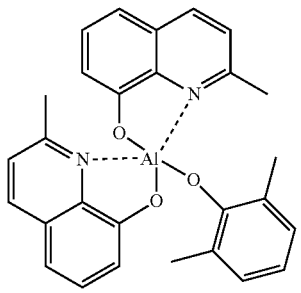
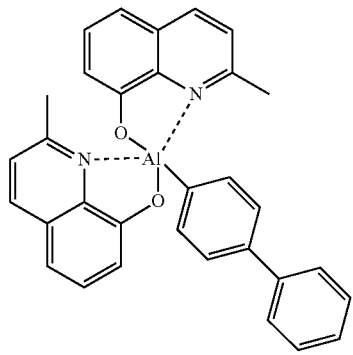

73 74
-continued
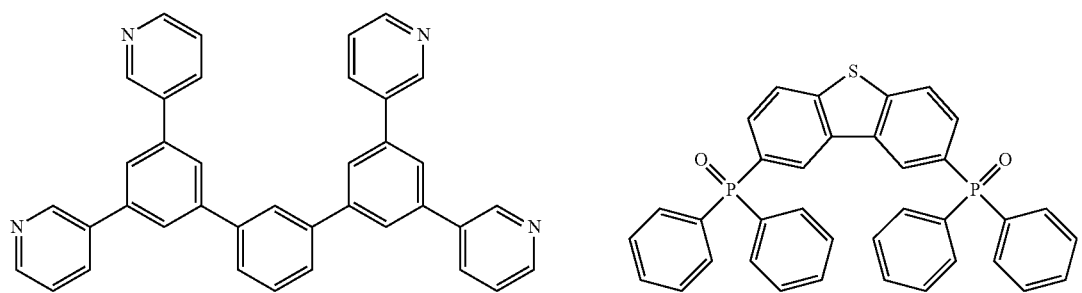
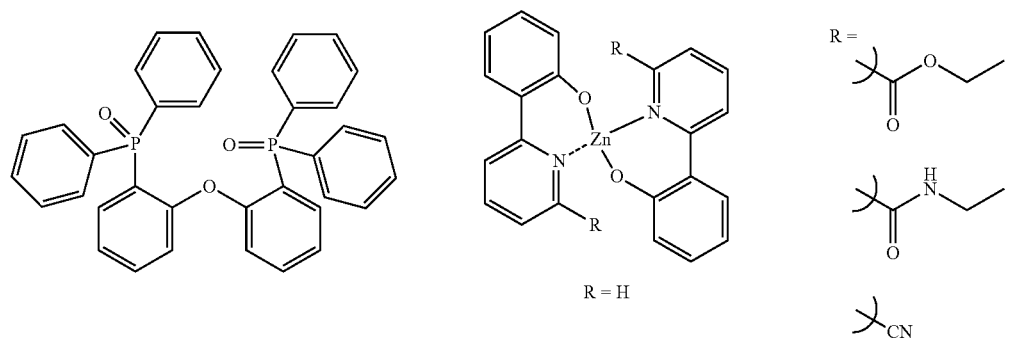
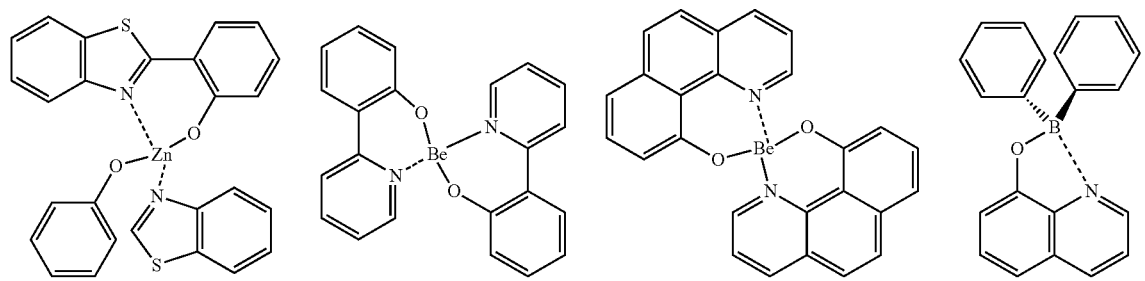
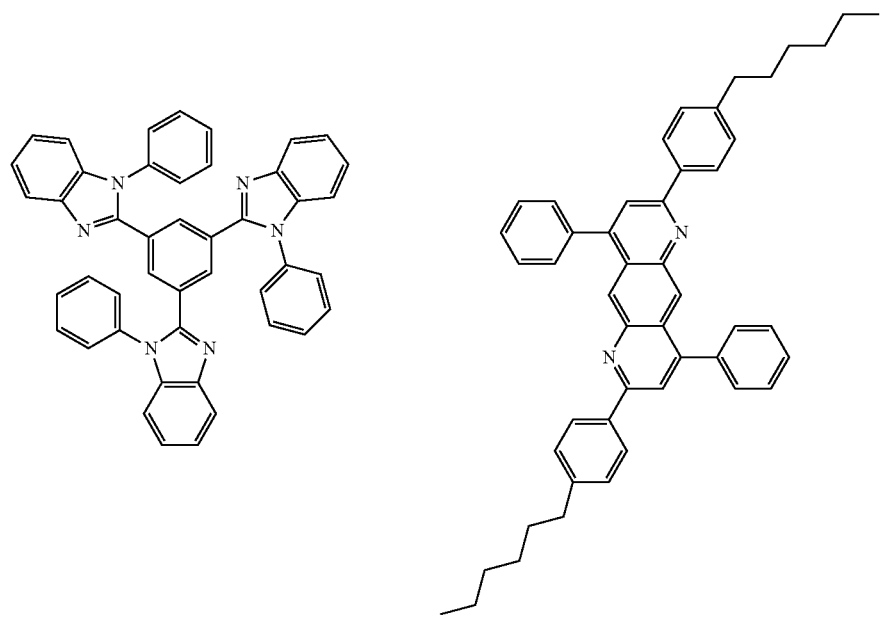

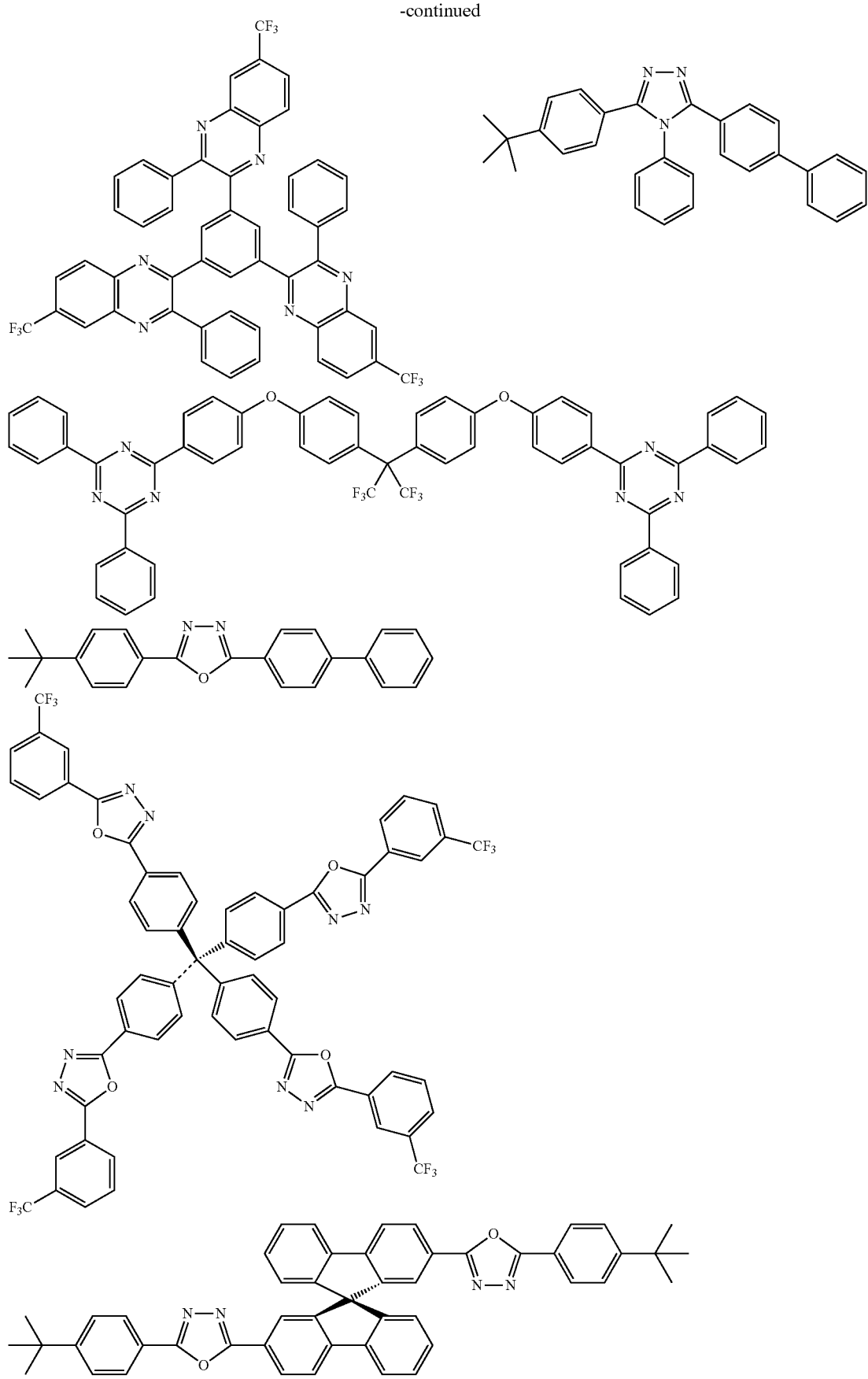

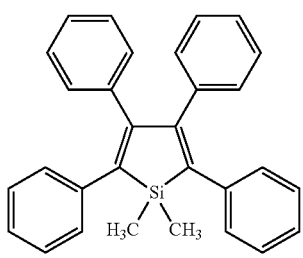
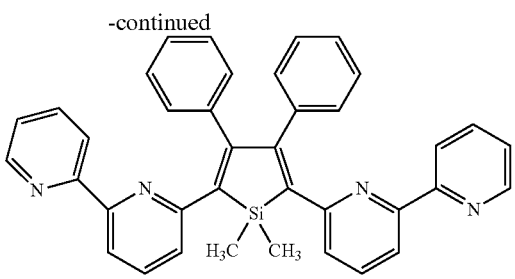
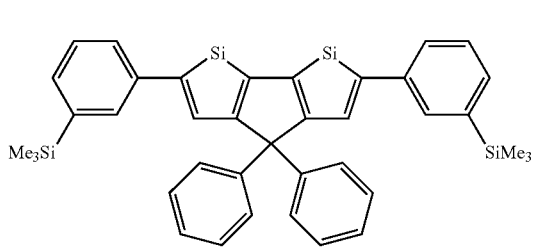
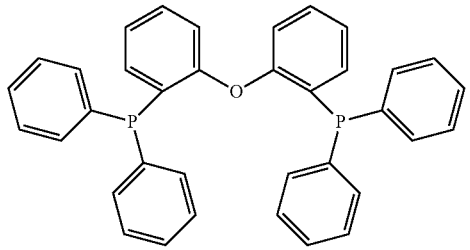
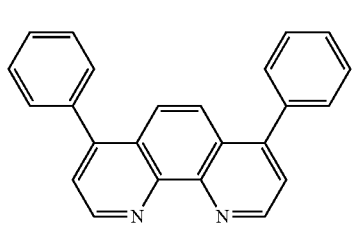
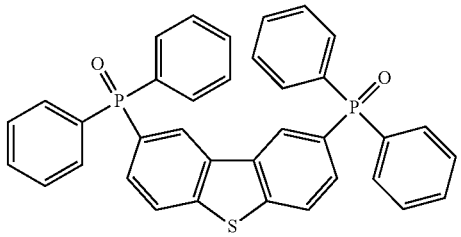
Preferred examples of a compound that may be used as the electron injection material are shown below.
Preferred examples of a compound as a material that may be added are shown below. For example, the compound may be added as a stabilizing material.
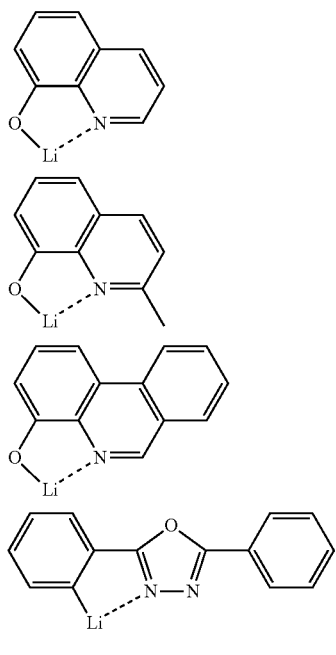
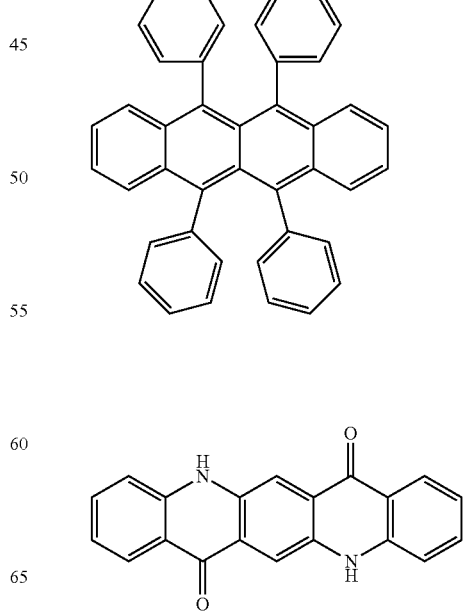

-continued

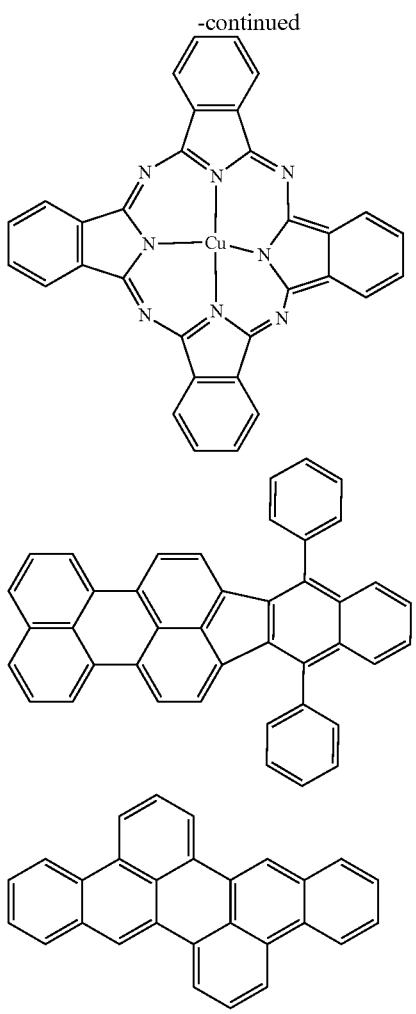

The organic electroluminescent device thus produced by the aforementioned method emits light on application of an electric field between the anode and the cathode of the device. In this case, when the light emission is caused by the excited singlet energy, light having a wavelength that corresponds to the energy level thereof may be confirmed as fluorescent light and delayed fluorescent light. When the light emission is caused by the excited triplet energy, light having a wavelength that corresponds to the energy level thereof may be confirmed as phosphorescent light. The normal fluorescent light has a shorter light emission lifetime than the delayed fluorescent light, and thus the light emission lifetime may be distinguished between the fluorescent light and the delayed fluorescent light.

The phosphorescent light may substantially not observed with a normal organic compound, such as the compound of the invention, at room temperature since the excited triplet energy is converted to heat or the like due to the instability thereof, and is immediately deactivated with a short lifetime. The excited triplet energy of the normal organic compound may be measured by observing light emission under an extremely low temperature condition.

The organic electroluminescent device of the invention may be applied to any of a single device, a structure with plural devices disposed in an array, and a structure having anodes and cathodes disposed in an X-Y matrix. According to the invention, an organic light-emitting device that is largely improved in light emission efficiency may be obtained by adding the compound represented by the general formula (1) in the light-emitting layer. The organic light-emitting device, such as the organic electroluminescent device, of the invention may be applied to a further wide range of purposes. For example, an organic electroluminescent display apparatus may be produced with the organic electroluminescent device of the invention, and for the details thereof, reference may be made to S. Tokito, C. Adachi and H. Murata, "Yuki EL Display" (Organic EL Display) (Ohmsha, Ltd.). In particular, the organic electroluminescent device of the invention may be applied to organic electroluminescent illumination and backlight which are highly demanded.

EXAMPLE

The features of the invention will be described more specifically with reference to synthesis examples and working examples below. The materials, processes, procedures and the like shown below may be appropriately modified unless they deviate from the substance of the invention. Accordingly, the scope of the invention is not construed as being limited to the specific examples shown below.

Synthesis of Compounds

Synthesis Example 1

Synthesis of Compound 1

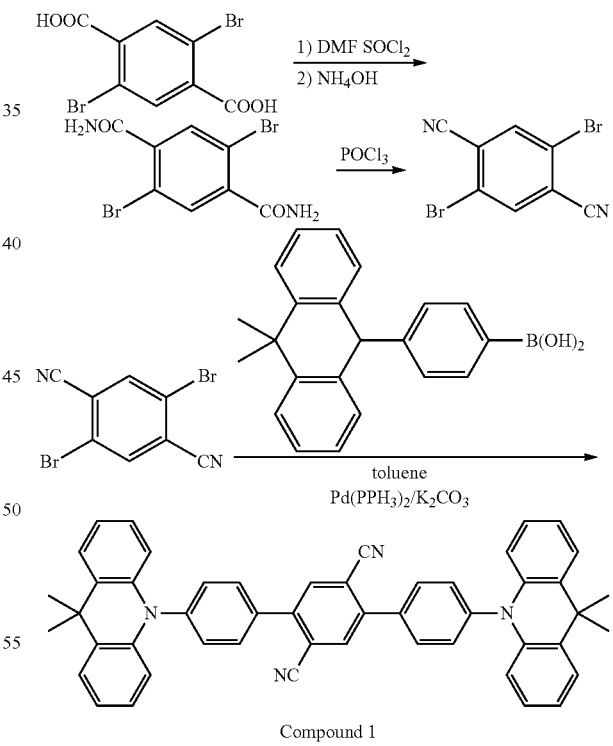

Compound 1

2,5-Dibromoterephthalic acid (14.7 g, 45.2 mmol), thionyl chloride (16.6 g, 14.0 mmol), a few drops of dimethylformamide (DMF) were placed in a two-neck flask under a nitrogen atmosphere, and refluxed under heating for 3 hours. Thereafter, toluene (50 mL) was added thereto, and thionyl chloride was removed through azeotropy therewith. The resulting deposit was dissolved in dioxane (20 mL), and the resulting solution was added dropwise to concentrated aqueous ammonia (60 mL), followed by stirring for 1 hour. The deposit was filtered to provide white powder (12.2 g, 94%). 2,5-Dibromobenzene-1,4-diamide (12.2 g, 37.9 mmol) and phosphoryl chloride (40.0 mL) were placed in a Schlenk flask under a nitrogen atmosphere, and stirred at 135° C. for 8 hours. Thereafter, the mixture was poured slowly to ice, and the deposit was filtered. The powder thus filtered was rinsed with water to provide 2,5-dibromobenzene-1,4-dinitrile as pale yellow powder (9.7 g, 90%).

2,5-Dibromobenzene-1,4-dinitrile (0.35 g, 1.2 mmol), 4,4,5,5-tetramethyl-2-(4-(9-acridinyl)phenyl)-1,3,2-dioxaborolane (1.1 g, 2.6 mmol), and dehydrated toluene (30 mL) were placed in a Schlenk flask under a nitrogen atmosphere, to which Pd(PPh$_3$)$_4$ (0.03 g, 0.03 mmol) and K$_2$CO$_3$ aq (2M, 15 mL) were then added, followed by stirring at 80° C. for 72 hours. After returning to room temperature, the deposit was filtered and rinsed with water, hexane, and methanol to provide the compound 1 as yellow powder (0.50 g, 83%).

$^1$H MNR (500 MHz, CDCl$_3$): 8.13 (s, 2H), 7.91 (d, J=8.0 Hz, 4H), 7.57 (d, J=8.0 Hz, 2H), 7.49 (d, J=7.7 Hz, 4H), 7.03 (t, J=7.3 Hz, 2H), 6.97 (t, J=7.5 Hz, 2H), 6.35 (d, J=8.2 Hz, 4H), 1.72 (s, 12H)

Synthesis Example 2

Synthesis of Compound 2

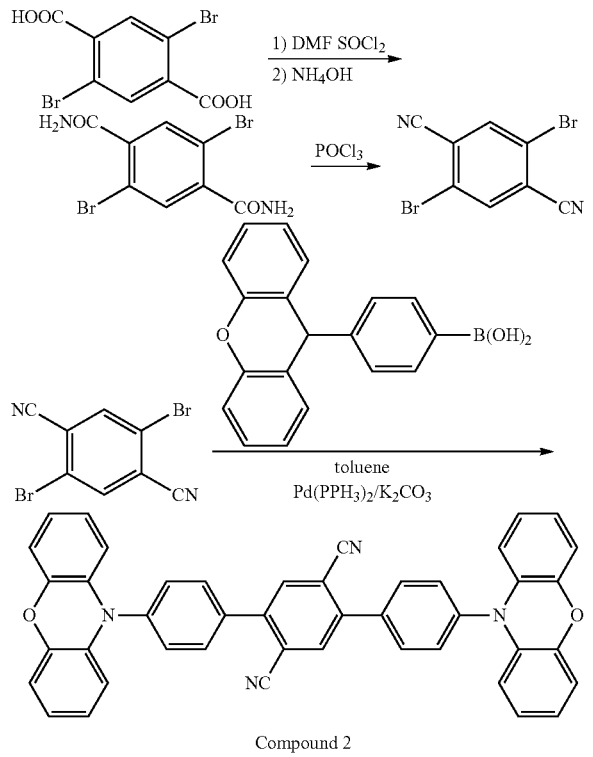

Compound 2

2,5-Dibromobenzene-1,4-dinitrile (0.32 g, 0.972 mmol) obtained in the same manner as in synthesis Example 1, 4,4,5,5-tetramethyl-2-(4-(10H-phenoxazin-10-yl)phenyl)-1,3,2-dioxaborolane (1.02 g, 2.6 mmol), and dehydrated toluene (30 mL) were placed in a Schlenk flask under a nitrogen atmosphere, to which Pd(PPh$_3$)$_4$ (0.03 g, 0.03 mmol) and K$_2$CO$_3$ aq (2M, 15 mL) were then added, followed by stirring at 80° C. for 72 hours. After returning to room temperature, the deposit was filtered and rinsed with water, hexane, and methanol to provide the compound 2 as white powder (0.76 g, 98%).

$^1$H MNR (500 MHz, CDCl$_3$): 8.07 (s, 2H), 7.87 (d, J=8.85 Hz, 4H), 7.58 (d, J=8.25 Hz, 4H), 6.75-6.64 (m, 12H), 7.87 (dd, J$_1$=19.6 Hz, J$_2$=1.25 Hz 4H)

Synthesis Example 3

Synthesis of Compound 3

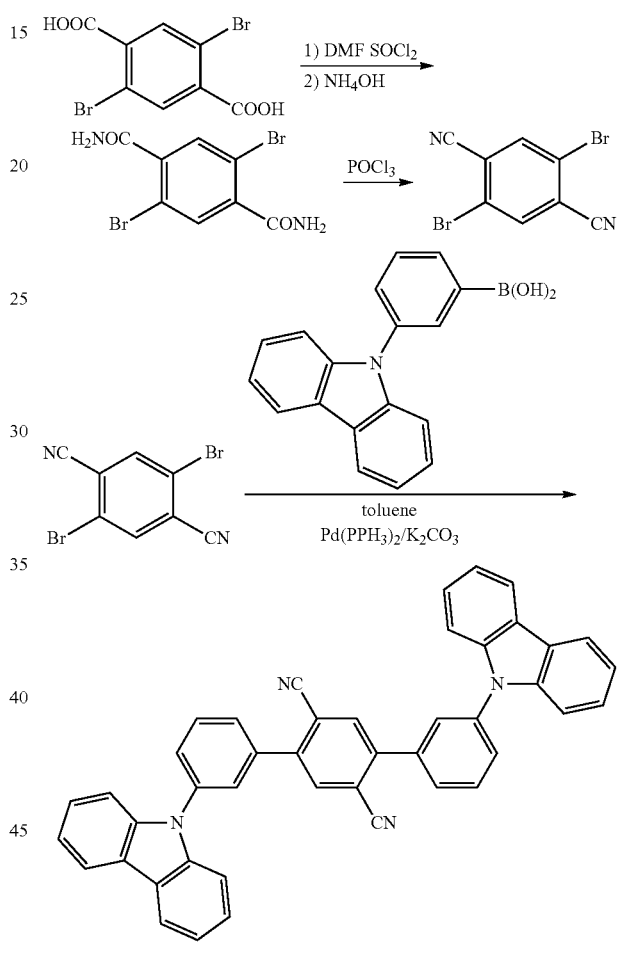

Compound 3

2,5-Dibromobenzene-1,4-dinitrile (0.278 g, 0.972 mmol) obtained in the same manner as in synthesis Example 1, 3-(9-carbazolyl)phenylboronic acid (0.640 g, 2.23 mmol), and dehydrated toluene (30 mL) were placed in a Schlenk flask under a nitrogen atmosphere, to which Pd(PPh$_3$)$_4$ (0.06 g, 0.05 mmol) and K$_2$CO$_3$ aq (2M, 15 mL) were then added, followed by stirring at 80° C. for 72 hours. After returning to room temperature, the deposit was filtered and rinsed with water, hexane, and methanol to provide the compound 3 as white powder (0.57 g, 93%).

$^1$H MNR (500 MHz, CDCl$_3$): δ 8.17 (d, J=7.5 Hz, 4H), 8.03 (s, 2H), 7.83-7.77 (m, 6H), 7.68 (d, J=7.3 Hz, 2H), 7.55 (d, J=8.1 Hz, 4H), 7.45 (t, J=7.2 Hz, 4H) 7.32 (t, J=7.35 Hz, 4H)

Synthesis Example 4

Synthesis of Compound 19

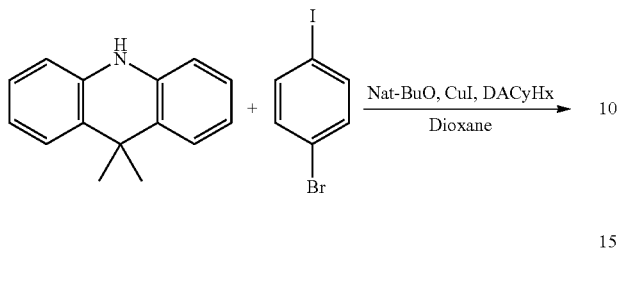

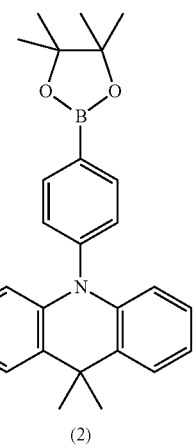

100 mL of 1,4-dioxane was placed in a flask having been substituted with nitrogen, to which 9,9-dimethyl-9,10-dihydroacridan (10 g, 47.8 mmol), 1-bromo-4-iodobenzene (14.9 g, 52.58 mmol), copper iodide (0.18 g, 0.96 mmol), sodium tert-butoxide (9.2 g, 95.6 mmol), and 1,2-diaminocyclohexane (0.55 g, 4.78 mmol) were then added. The reaction solution was heated and refluxed for 6 hours. Thereafter, the temperature was lowered, and impurities were removed with Celite. The resulting filtrate was purified by column chromatography to provide an intermediate (1) as a white solid matter (15.5 g, 89%).

$^1$H NMR (500 MHz, CDCl$_3$): 7.75 (d, J=8.5 Hz, 2H), 7.45 (dd, J=9.5 Hz, 2 Hz, 2H), 7.22 (d, J=8.5 Hz, 2H), 6.95 (m, 4H), 6.24 (dd, J=9.5 Hz, 1.5 Hz, 2H), 1.54 (s, 6H)

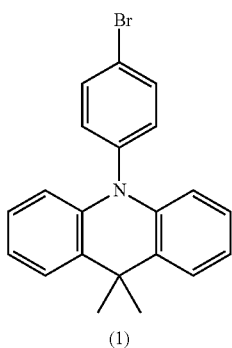

The intermediate (1) (10 g, 27.4 mmol) and 100 mL of tetrahydrofuran were placed in a flask having been substituted with nitrogen, and stirred at −78° C. 200 mL of tetrahydrofuran having n-butyl lithium (1.6 M, 19.9 mL, 31.8 mmol) having been added thereto was added dropwise thereto over 30 minutes. After completing the dropwise addition, 2-isopropoxy-4,4,5,5-tetramethyl-1,3,2-dioxaborolane (5.62 g, 30.14 mmol) was added dropwise thereto over 20 minutes, and the reaction solution was stirred at room temperature for 2 hours. Thereafter, 100 mL of water was added to the reaction solution, and after 30 minutes, chloroform was added, followed by extracting. The resulting organic layer was dried over magnesium sulfate, and a filtrate was obtained by suction filtration. Thereafter, recrystallization was performed from methanol to provide an intermediate (2) as a white solid matter (8.1 g, 73%).

$^1$H NMR (500 MHz, CDCl$_3$): 8.06 (d, J=8.0 Hz, 2H), 7.44 (dd, J=9.0 Hz, 1.5 Hz, 2H), 7.34 (d, J=8.0 Hz, 2H), 6.96-6.89 (m, 4H), 6.24 (dd, J=9.5 Hz, 1.5 Hz, 2H), 1.69 (s, 6H), 1.40 (s, 12H)

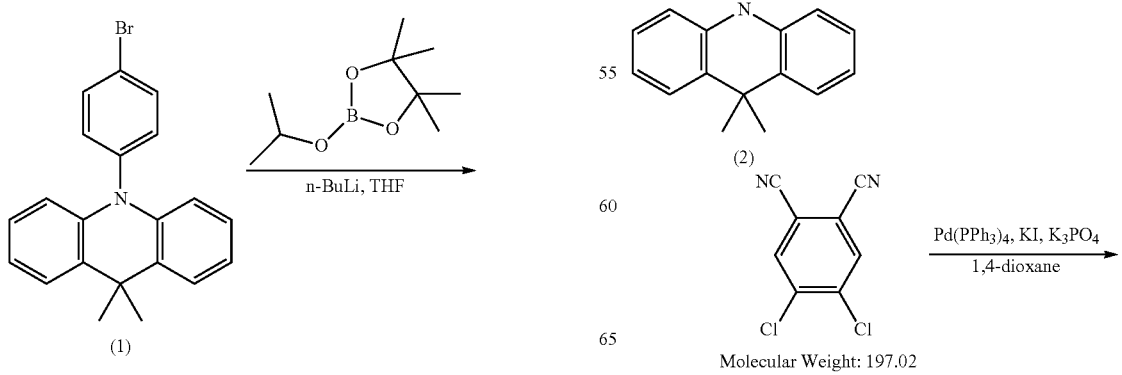

Molecular Weight: 197.02

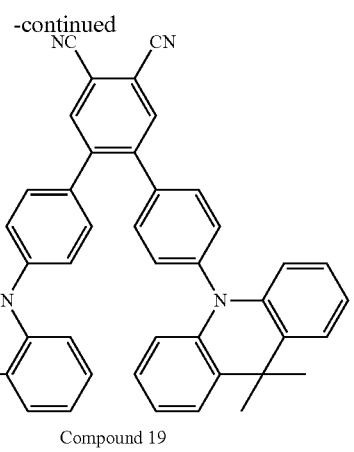

Compound 19

4,5-Dichlorophthalonitrile (1 g, 5 mmol), the intermediate (2) (4.17 g, 10 mmol), tetrakis(triphenylphosphine) palladium(0) (0.059 g, 0.05 mmol), potassium iodide (1.69 g, 10 mmol), and potassium phosphate (4.31 g, 20 mmol) were placed in a flask having been substituted with nitrogen, dissolved in 1,4-dioxane and refluxed for 48 hours. Thereafter, the temperature was lowered, and impurities were removed with Celite. The resulting filtrate was purified by column chromatography to provide the compound 19 as a yellow solid matter (1 g, 34%).

$^1$H NMR (500 MHz, CDCl$_3$): 7.99 (s, 1H), 7.94 (s, 1H), 7.69 (dd, J=8.5 Hz, 1.5 Hz, 4H), 7.49 (td, J=17.5 Hz, 1.5 Hz, 2H), 7.05-6.95 (m, 8H), 6.30 (dd, J=9.5 Hz, 1.5 Hz, 4H), 1.53 (s, 6H)

Synthesis Example 5

Synthesis of Compound 20

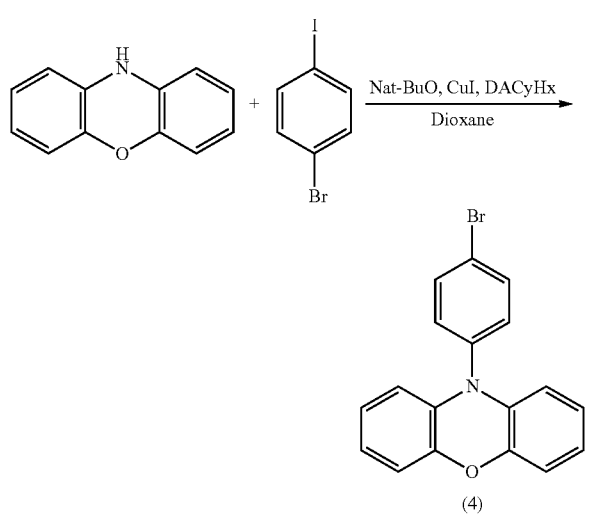

100 mL of 1,4-dioxane was placed in a flask having been substituted with nitrogen, to which 10H-phenoxazine (10 g, 54.5 mmol), 1-bromo-4-iodobenzene (17 g, 60 mmol), copper iodide (0.21 g, 1.09 mmol), sodium tert-butoxide (10.5 g, 109 mmol), and 1,2-diaminocyclohexane (0.62 g, 5.45 mmol) were then added. The reaction solution was heated and refluxed for 6 hours. Thereafter, the temperature was lowered, and impurities were removed with Celite. The resulting filtrate was purified by column chromatography to provide an intermediate (4) as a white solid matter (15 g, 81%).

$^1$H NMR (500 MHz, CDCl$_3$): 7.72 (d, J=9 Hz, 2H), 7.23 (d, J=8.5 Hz, 2H), 6.74-6.57 (m, 6H), 5.91 (dd, J=9 Hz, 1.5 Hz, 2H)

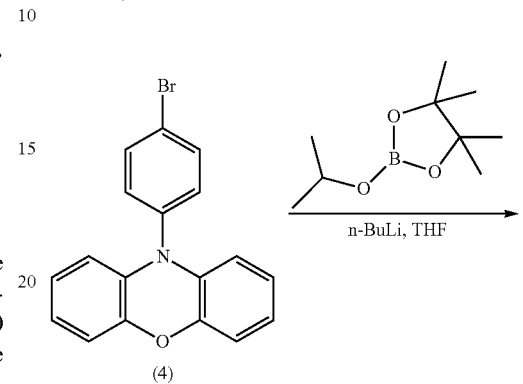

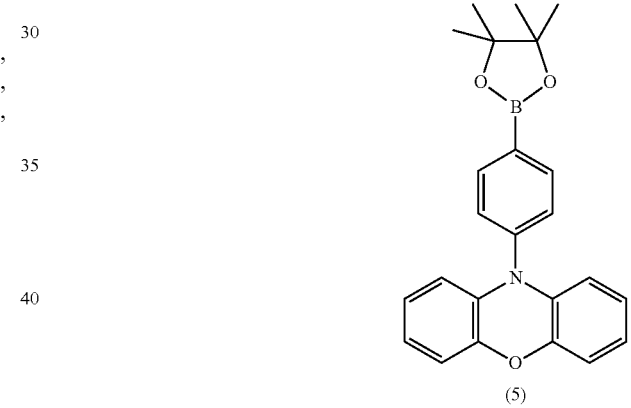

The intermediate (4) (10 g, 30.0 mmol) and 100 mL of tetrahydrofuran were placed in a flask having been substituted with nitrogen, and stirred at −78° C. 200 mL of tetrahydrofuran having n-butyl lithium (1.6 M, 19.9 mL, 31.8 mmol) having been added thereto was added dropwise thereto. Thereafter, 2-isopropoxy-4,4,5,5-tetramethyl-1,3,2-dioxaborolane (5.62 g, 30.14 mmol) was added dropwise thereto over 20 minutes, and the reaction solution was stirred at room temperature for 2 hours. Thereafter, 100 mL of water was added to the reaction solution, and after 30 minutes, chloroform was added, followed by extracting. The resulting organic layer was dried over magnesium sulfate, and a filtrate was obtained by suction filtration. Thereafter, recrystallization was performed from methanol to provide an intermediate (5) as a white solid matter (7.6 g, 67%).

$^1$H NMR (500 MHz, CDCl$_3$): 8.02 (d, J=8.5 Hz, 2H), 7.35 (d, J=8.5 Hz, 2H), 6.68 (dd, J=8.5 Hz, 1.5 Hz, 2H), 6.63 (td, J=8 Hz, 1.5 Hz, 4H), 6.56 (td, J=8 Hz, 1.5 Hz, 2H), 5.91 (dd, J=8 Hz, 1.5 Hz, 2H), 1.38 (s, 12H)

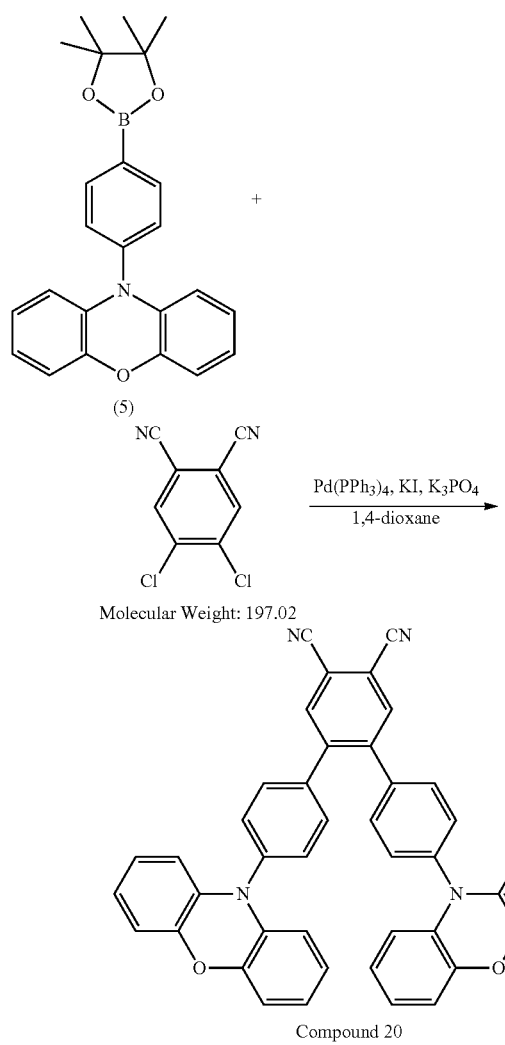

4,5-Dichlorophthalonitrile (1 g, 5 mmol), the intermediate (5) (3.91 g, 10 mmol), tetrakis(triphenylphosphine) palladium(0) (0.059 g, 0.05 mmol), potassium iodide (1.69 g, 10 mmol), and potassium phosphate (4.31 g, 20 mmol) were placed in a flask having been substituted with nitrogen, dissolved in 1,4-dioxane and refluxed for 48 hours. Thereafter, the temperature was lowered, and impurities were removed with Celite. The resulting filtrate was purified by column chromatography to provide the compound 20 as an orange solid matter (0.98 g, 30%).

$^1$H NMR (500 MHz, CDCl$_3$): 8.01 (s, 2H), 7.38 (d, J=8 Hz, 4H), 7.33 (d, J=8 Hz, 4H), 6.69 (d, J=7.5 Hz, 4H), 6.65-6.54 (m, 4H), 6.47 (t, J=7.5 Hz, 4H), 5.82 (d, J=7.5 Hz, 4H)

Synthesis Example 6

Synthesis of Compound 30

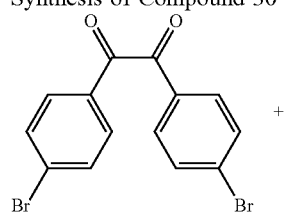

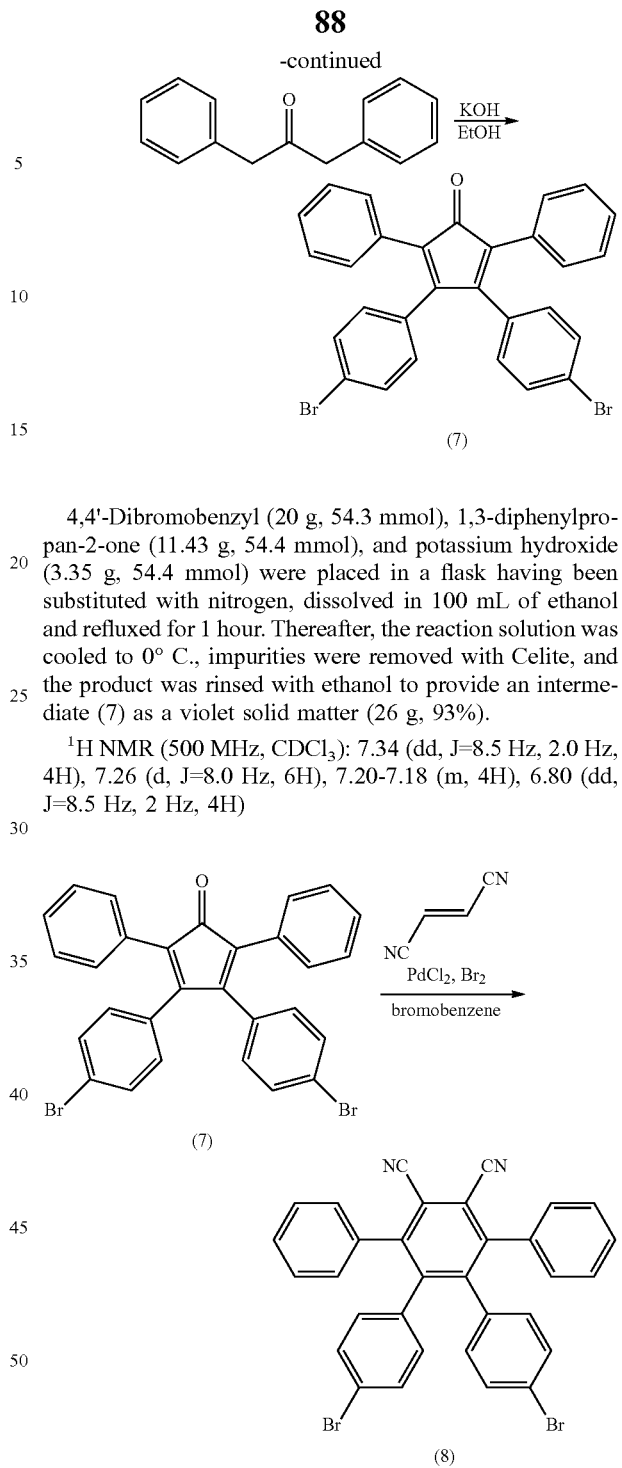

4,4'-Dibromobenzyl (20 g, 54.3 mmol), 1,3-diphenylpropan-2-one (11.43 g, 54.4 mmol), and potassium hydroxide (3.35 g, 54.4 mmol) were placed in a flask having been substituted with nitrogen, dissolved in 100 mL of ethanol and refluxed for 1 hour. Thereafter, the reaction solution was cooled to 0° C., impurities were removed with Celite, and the product was rinsed with ethanol to provide an intermediate (7) as a violet solid matter (26 g, 93%).

$^1$H NMR (500 MHz, CDCl$_3$): 7.34 (dd, J=8.5 Hz, 2.0 Hz, 4H), 7.26 (d, J=8.0 Hz, 6H), 7.20-7.18 (m, 4H), 6.80 (dd, J=8.5 Hz, 2 Hz, 4H)

The intermediate (7) (19 g, 35.0 mmol), phthalonitrile (2.73 g, 35.0 mmol), and palladium(II) chloride (0.06 g, 0.35 mmol) were placed in a flask having been substituted with nitrogen, dissolved in 150 mL of bromobenzene and refluxed for 2 hours. Thereafter, the reaction solution was cooled, to which bromine (6.15 g, 38.5 mmol) dissolved in 50 mL of bromobenzene was slowly added, followed by refluxing for 5 hours. Thereafter, the temperature was lowered, and impurities were removed with Celite. The resulting filtrate was purified by column chromatography to provide an intermediate (8) as a white solid matter (13.4 g, 64%).

$^1$H NMR (500 MHz, CDCl$_3$): 7.44 (d, J=8.5 Hz, 2H), 7.29 (dd, J=7.0 Hz, 1.0 Hz, 4H), 7.15 (d, J=8.5 Hz, 2H), 7.12-7.09 (m, 4H), 6.99 (d, J=8.5 Hz, 2H), 6.57 (dd, J=8.5 Hz, 2.0 Hz, 2H)

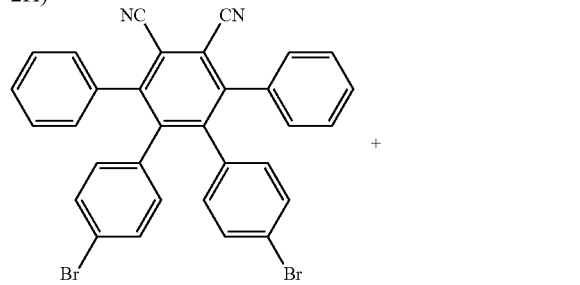

(8)

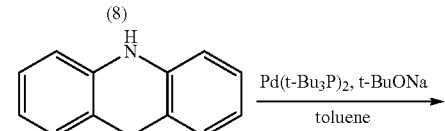

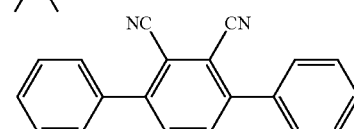

Compound 30

The intermediate (8) (1.5 g, 2.5 mmol), 9,9-dimethyl-9,10-dihydroacridan (1.06 g, 5.1 mmol), bis(tri-tert-butyl-phosphine) palladium(0) (0.013 g, 0.025 mmol), sodium tert-butoxide (1.0 g, 10 mmol), and 30 mL of toluene were placed in a flask having been substituted with nitrogen. After refluxing for 6 hours, the temperature was lowered, and impurities were removed with Celite. The resulting filtrate was purified by column chromatography to provide the compound 30 as a yellow solid matter (1.1 g, 51%).

$^1$H NMR (500 MHz, CDCl$_3$): 7.39-7.38 (m, 12H), 7.30 (dd, J=8 Hz, 2.0 Hz, 2H), 7.11 (dd, J=8.35 Hz, 1.5 Hz, 4H), 7.03 (dd, J=8.0 Hz, 1.5 Hz, 4H), 6.83 (td, J=16.0 Hz, 1.0 Hz 4H), 6.71 (td, J=17.0 Hz, 1.5 Hz, 4H), 5.85 (d, J=8.5 Hz, 1.0 Hz, 4H), 1.53 (s, 12H)

Synthesis Example 7

Synthesis of Compound 31

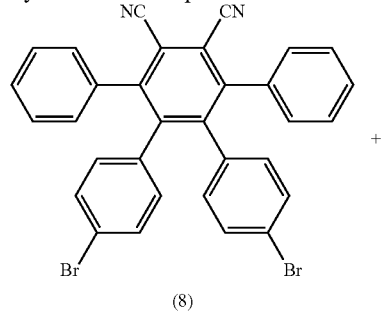

(8)

+

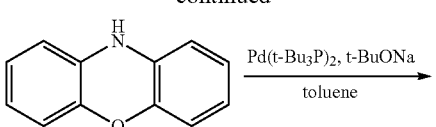

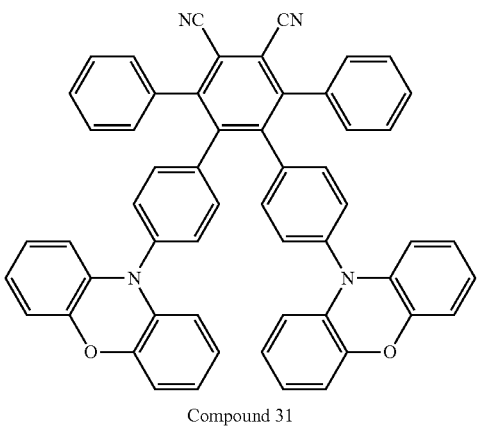

Compound 31

The intermediate (8) (1.5 g, 2.5 mmol) obtained in the same manner as in Synthesis Example 6, 10H-phenoxazine (0.93 g, 5.1 mmol), bis(tri-tert-butylphosphine) palladium (0) (0.013 g, 0.025 mmol), sodium tert-butoxide (1.0 g, 10 mmol), and 30 mL of toluene were placed in a flask having been substituted with nitrogen. After refluxing for 6 hours, the temperature was lowered, and impurities were removed with Celite. The resulting filtrate was purified by column chromatography to provide the compound 31 as an orange solid matter (0.9 g, 44%).

Synthesis Example 8

Synthesis of Compound 32

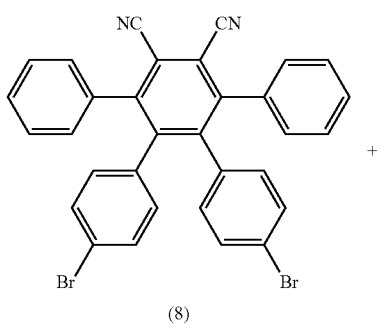

(8)

+

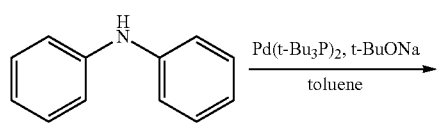

-continued

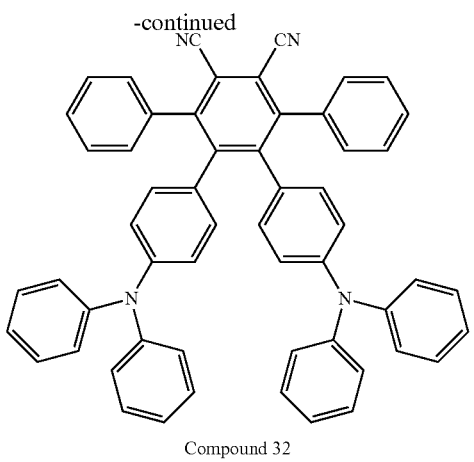

Compound 32

The intermediate (8) (1.5 g, 2.5 mmol) obtained in the same manner as in Synthesis Example 6, diphenylamine (0.86 g, 5.1 mmol), bis(tri-tert-butylphosphine) palladium (0) (0.013 g, 0.025 mmol), sodium tert-butoxide (1.0 g, 10 mmol), and 30 mL of toluene were placed in a flask having been substituted with nitrogen. After refluxing for 6 hours, the temperature was lowered, and impurities were removed with Celite. The resulting filtrate was purified by column chromatography to provide the compound 32 as a yellow solid matter (1.65 g, 85%).

$^1$H NMR (500 MHz, CDCl$_3$): 7.33 (dd, J=10.5 Hz, 2.0 Hz, 6H), 7.20-7.17 (m, 12H), 7.33 (td, J=15.0 Hz, 1.0 Hz, 4H), 6.90 (dd, J=7.5 Hz, 1.0 Hz, 8H), 6.69 (dd, J=8.5 Hz, 1.0 Hz, 4H), 6.57 (dd, J=8.5 Hz, 1.0 Hz, 4H)

Production and Evaluation of Devices

Organic photoluminescent devices and organic electroluminescent devices were produced and evaluated as follows.

The light emission characteristics were evaluated by using a source meter (2400 Series, produced by Keithley Instruments Inc.), a semiconductor parameter analyzer (E5273A, produced by Agilent Technologies, Inc.), an optical power meter (1930C, produced by Newport Corporation), an optical spectrometer (USB2000, produced by Ocean Optics, Inc.), a spectroradiometer (SR-3, produced by Topcon Corporation), and a streak camera (Model C4334, produced by Hamamatsu Photonics K.K.).

The difference ($\Delta E_{ST}$) between the singlet energy ($E_{S1}$) and the triplet energy ($E_{T1}$) of the materials was obtained in such a manner that the singlet energy ($E_{S1}$) and the triplet energy ($E_{T1}$) were calculated in the following manners, and the difference was obtained by the expression, $\Delta E_{ST}=E_{S1}-E_{T1}$.

(1) Singlet Energy $E_{S1}$

The compound to be measured and mCP were vapor-co-deposited to a thickness of 100 nm on a Si substrate to make a concentration of the compound to be measured of 6% by weight, which was designated as a specimen. The specimen was measured for a fluorescence spectrum at ordinary temperature (300 K). The light emission was accumulated from immediately after the incidence of excitation light to after 100 nsec from the incidence, thereby providing a fluorescence spectrum with the fluorescence intensity as the ordinate and the wavelength as the abscissa. In the fluorescence spectrum, the ordinate was the light emission, and the abscissa was the wavelength. A tangent line was drawn for the downfalling part of the light emission spectrum on the short wavelength side, and the wavelength λedge [nm] of the intersection point of the tangent line and the abscissa was obtained. The wavelength value was converted to an energy value according to the following conversion expression to provide the singlet energy $E_{S1}$.

$E_{S1}$ [eV]=1,239.85/λedge     Conversion Expression

The light emission spectrum was measured with a nitrogen laser (MNL200, produced by Lasertechnik Berlin GmbH) as an excitation light source and a streak camera (C4334, produced by Hamamatsu Photonics K.K.) as a detector.

(2) Triplet Energy $E_{T1}$

The same specimen as used for the singlet energy $E_{S1}$ was cooled to 5 K, the specimen for measuring phosphorescent light was irradiated with excitation light (337 nm), and the phosphorescence intensity was measured with a streak camera. The light emission was accumulated from after 1 msec from the incidence of excitation light to after 10 msec from the incidence, thereby providing a phosphorescence spectrum with the phosphorescence intensity as the ordinate and the wavelength as the abscissa. A tangent line was drawn for the upstanding part of the phosphorescence spectrum on the short wavelength side, and the wavelength λedge [nm] of the intersection point of the tangent line and the abscissa was obtained. The wavelength value was converted to an energy value according to the following conversion expression to provide the triplet energy $E_{T1}$.

$E_{T1}$ [eV]=1,239.85/λedge     Conversion Expression

The tangent line for the upstanding part of the phosphorescence spectrum on the short wavelength side was drawn in the following manner. Over the range in the phosphorescence spectrum curve of from the short wavelength end to the maximum peak value closest to the short wavelength end among the maximum peak values of the spectrum, a tangent line was assumed while moving within the range toward the long wavelength side. The gradient of the tangent line was increased while the curve was standing up (i.e., the value of the ordinate was increased). The tangent line that was drawn at the point where the gradient thereof became maximum was designated as the tangent line for the upstanding part of the phosphorescence spectrum on the short wavelength side.

A maximum peak having a peak intensity that was 10% or less of the maximum peak intensity of the spectrum was not included in the maximum peak values and thus was not designated as the maximum peak value closest to the short wavelength end, and the tangent line that was drawn at the point where the gradient became maximum that was closest to the maximum peak value closest to the short wavelength end was designated as the tangent line for the upstanding part of the phosphorescence spectrum on the short wavelength side.

$\Delta E_{ST}$ is preferably less than 0.20 eV, more preferably less than 0.11 eV, further preferably less than 0.05 eV, and still further preferably 0.01 eV.

Example 1

Production and Evaluation of Organic Photoluminescent Device Using Compound 1

A toluene solution of the compound 1 (concentration: $10^{-4}$ mol/L) was prepared in a glove box under an Ar atmosphere.

The compound 1 and PzCz were vapor-deposited from separate vapor deposition sources on a quartz substrate by a vacuum vapor deposition method under a condition of a vacuum degree of $10^{-4}$ Pa or less to provide a thin film having a thickness of 100 nm and a concentration of the compound 1 of 6.0% by weight, which was designated as an organic photoluminescent device.

Figure 2:
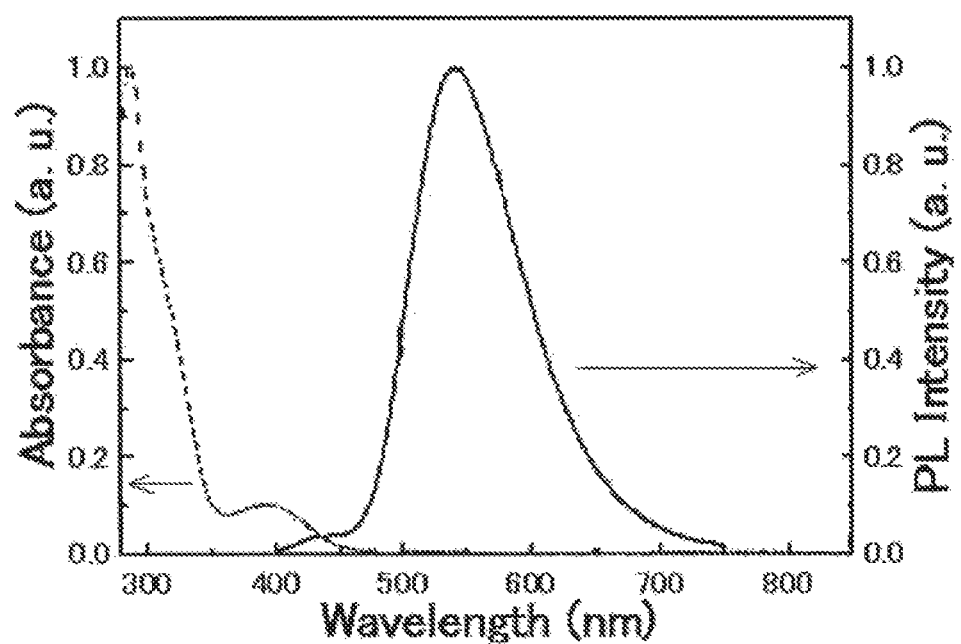
FIG. 2 shows the light emission spectra of the toluene solution of the compound 1 in Example 1.
Figure 3:
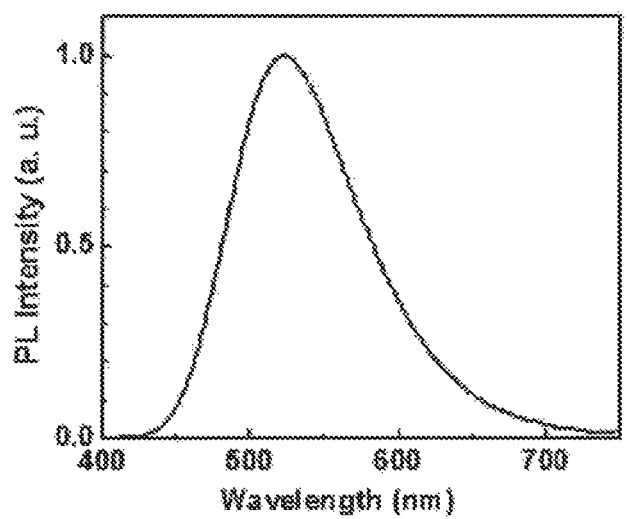
FIG. 3 shows the light emission spectrum of the thin film organic photoluminescent device of the compound 1 in Example 1.

FIG. 2 shows the result of measurement of the light emission spectra of the toluene solution of the compound 1 with excitation light of 300 nm, and FIG. 3 shows the result of measurement of the light emission spectrum of the organic photoluminescent device having a thin film of the compound 1 and PzCz with excitation light of 290 nm.

The photoluminescence quantum efficiency was 100% for the toluene solution bubbled with nitrogen, and 84% for the organic photoluminescent device having a thin film of the compound 1 and PzCz. The energy difference $\Delta E_{ST}$ between the singlet excitation state and the triplet excitation state obtained from the fluorescent spectrum and the phosphorescent spectrum was 0.002 eV.

Figure 4:
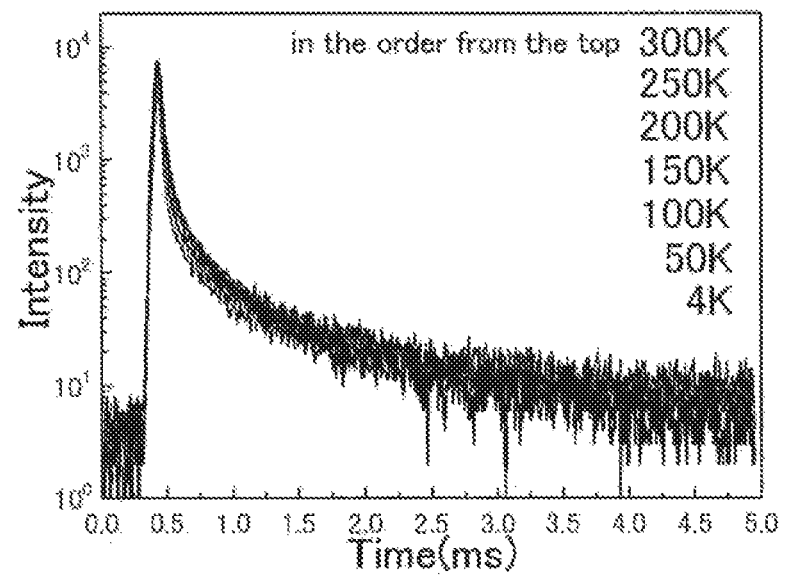
FIG. 4 shows the transient decay curves of the thin film organic photoluminescent device of the compound 1 in Example 1.

FIG. 4 shows the transient decay curves of the thin film organic photoluminescent device having a thin film of the compound 1 and PzCz at 4 K, 50 K, 100 K, 150 K, 200 K, 250 K, and 300 K. The transient decay curve shows the measurement result of the light emission lifetime obtained by measuring the process where the light emission intensity is deactivated on irradiating the compound with excitation light. In ordinary one-component light emission (fluorescent light or phosphorescent light), the light emission intensity is decays monoexponentially. This means that the light emission intensity decays linearly on a graph with the semilogarithm as the ordinate. In a transient decay curve of the compound 1 shown in FIG. 4, while a linear component (fluorescent light) was observed in the initial stage of observation, a component that deviated from the linearity appeared after several microseconds. The later component is light emission of the delayed component, and the signal thereof added to the initial component appears as a long tail curve on the longer time side. Thus, the measurement of the light emission lifetime revealed that the compound 1 was a light-emitting material that contained a delayed component in addition to a fluorescent component. The light emission lifetime τ1 of the prompt fluorescent component at 300 K was 25 ns, and the light emission lifetime τ2 of the delayed fluorescent component was 117 µs. It was confirmed from FIG. 4 that the compound 1 was a thermal activation type delayed fluorescent material (TADF).

Example 2

Production and Evaluation of Organic Photoluminescent Device Using Compound 2

A toluene solution of the compound 2 and an organic photoluminescent device having a thin film thereof were provided in the same manner as in Example 1 except that the compound 2 was used instead of the compound 1. In the formation of the thin film, however, CBP was used instead of PzCz, and the concentration of the compound 2 was changed to 3% by weight.

Figure 5:
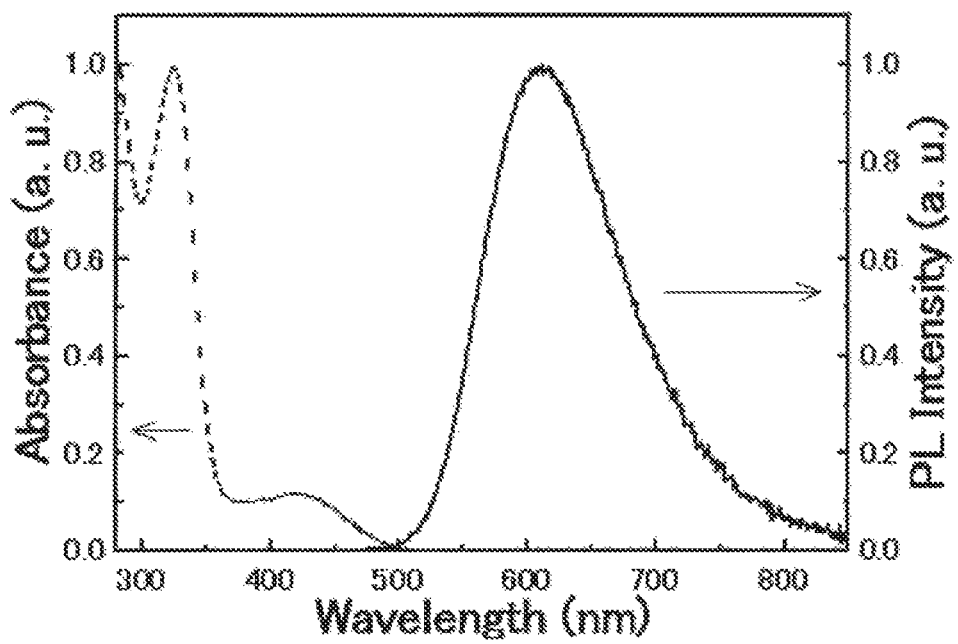
FIG. 5 shows the light emission spectra of the toluene solution of the compound 2 in Example 2.
Figure 6:
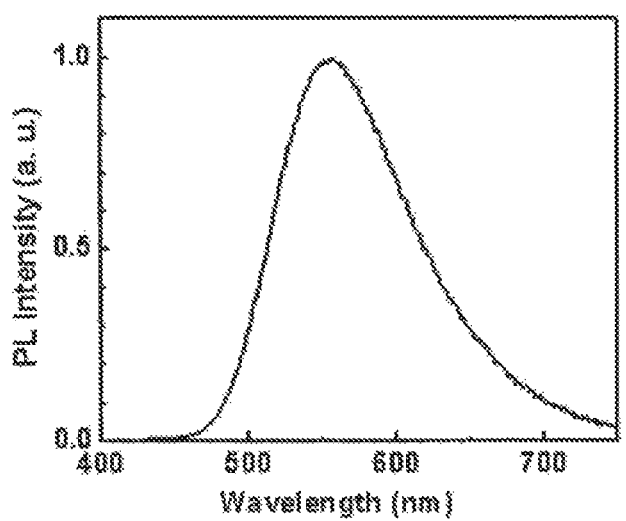
FIG. 6 shows the light emission spectrum of the thin film organic photoluminescent device of the compound 2 in Example 2.

FIG. 5 shows the result of measurement of the light emission spectra of the toluene solution of the compound 2 with excitation light of 300 nm, and FIG. 6 shows the result of measurement of the light emission spectrum of the organic photoluminescent device having a thin film of the compound 2 and CBP with excitation light of 290 nm.

Figure 7:
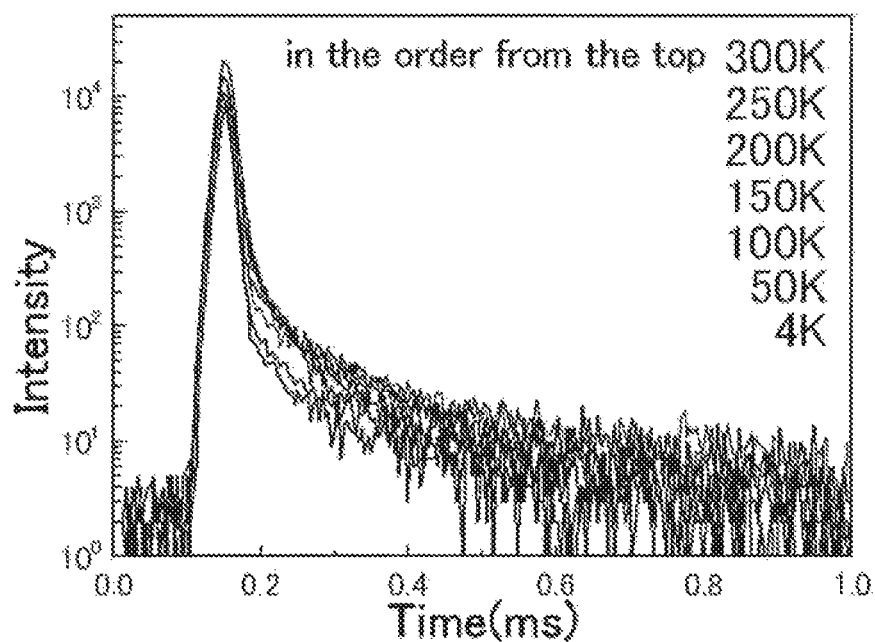
FIG. 7 shows the transient decay curves of the thin film organic photoluminescent device of the compound 2 in Example 2.

The photoluminescence quantum efficiency was 30% for the toluene solution bubbled with nitrogen, and 68% for the organic photoluminescent device having a thin film of the compound 2 and CBP. The energy difference $\Delta E_{ST}$ between the singlet excitation state and the triplet excitation state obtained from the fluorescent spectrum and the phosphorescent spectrum was 0.101 eV. FIG. 7 shows the transient decay curves of the thin film organic photoluminescent device having a thin film of the compound 2 and CBP at 4 K, 50 K, 100 K, 150 K, 200 K, 250 K, and 300 K. The light emission lifetime τ1 of the prompt fluorescent component at 300 K was 22 ns, and the light emission lifetime t2 of the delayed fluorescent component was 763 ns. It was confirmed from FIG. 7 that the compound 2 was a thermal activation type delayed fluorescent material (TADF).

Example 3

Production and Evaluation of Organic Photoluminescent Device Using Compound 3

A toluene solution of the compound 3 and an organic photoluminescent device having a thin film thereof were provided in the same manner as in Example 1 except that the compound 3 was used instead of the compound 1. In the formation of the thin film, however, DPEPO was used instead of PzCz, and the concentration of the compound 3 was changed to 3% by weight.

Figure 8:
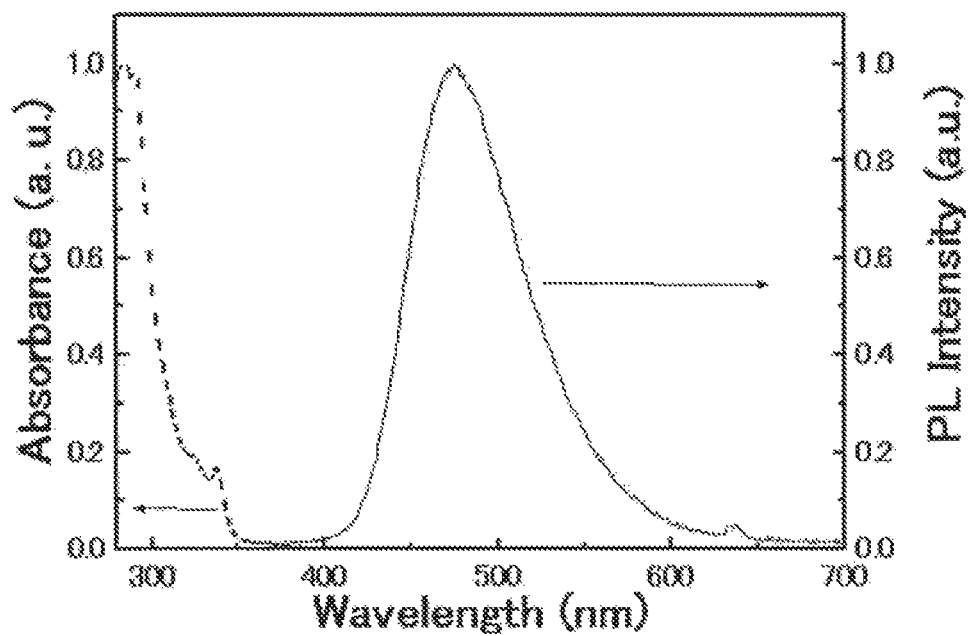
FIG. 8 shows the light emission spectra of the toluene solution of the compound 3 in Example 3.

FIG. 8 shows the result of measurement of the light emission spectra of the toluene solution of the compound 3 with excitation light of 475 nm.

The photoluminescence quantum efficiency was 10% for the toluene solution with no bubbling, 38% for the toluene solution bubbled with nitrogen, and 38% for the organic photoluminescent device having a thin film of the compound 3 and DPEPO. The energy difference $\Delta E_{ST}$ between the singlet excitation state and the triplet excitation state obtained from the fluorescent spectrum and the phosphorescent spectrum was 0.032 eV.

Figure 9:
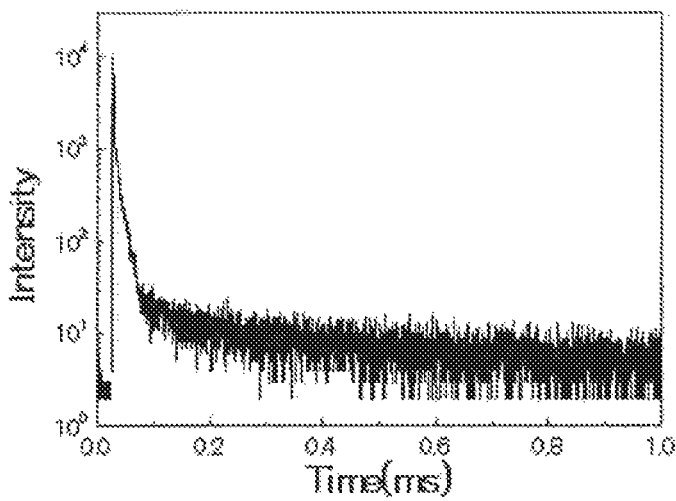
FIG. 9 shows the transient decay curve of the thin film organic photoluminescent device of the compound 3 in Example 3.

FIG. 9 shows the transient decay curve of the thin film organic photoluminescent device having a thin film of the compound 3 and DPEPO. The light emission lifetime τ1 of the prompt fluorescent component was 27 ns, and the light emission lifetime τ2 of the delayed fluorescent component was 196 s.

Example 4

Production and Evaluation of Organic Photoluminescent Device Using Compound 19

A toluene solution of the compound 19 and an organic photoluminescent device having a thin film thereof were provided in the same manner as in Example 1 except that the compound 19 was used instead of the compound 1. In the formation of the thin film, however, mCBP was used instead of PzCz.

Separately, a thin film formed only of the compound 19 was formed to a thickness of 100 nm on a quartz substrate by a vacuum vapor deposition method under a condition of a vacuum degree of $10^{-4}$ Pa or less to provide an organic photoluminescent device.

Figure 10:
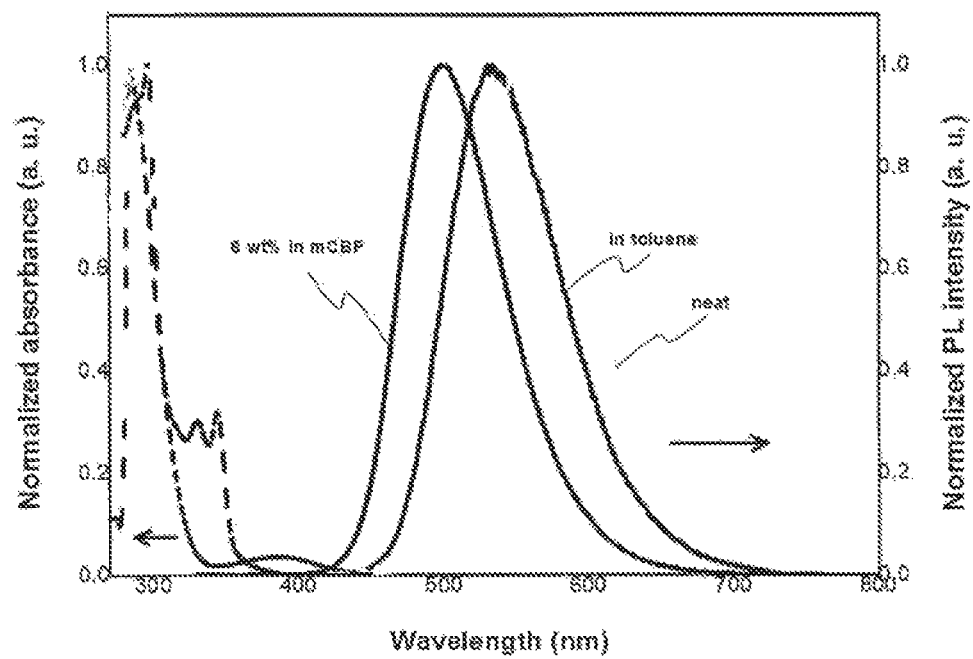
FIG. 10 shows the light emission spectra of the toluene solution of the compound 19, the thin film organic photoluminescent device of the compound 19, and the thin film organic photoluminescent device of the compound 19 and mCBP, in Example 4.

FIG. 10 shows the result of measurement of the light emission spectra of the toluene solution of the compound 19, the organic photoluminescent device having a thin film of the compound 19, and the organic photoluminescent device having a thin film of the compound 19 and mCBP, with excitation light of 350 nm.

The photoluminescence quantum efficiency with excitation light of 380 nm was 13.8% for the toluene solution with no bubbling, 58.9% for the toluene solution bubbled with nitrogen, 31.3% for the organic photoluminescent device having a thin film of the compound 19 disposed in the air atmosphere, and 31.6% therefor disposed in a nitrogen atmosphere. The photoluminescence quantum efficiency with excitation light of 335 nm was 77.7% for the organic photoluminescent device having a thin film of the compound 19 and mCBP disposed in the air atmosphere, and 86.0% therefor disposed in a nitrogen atmosphere.

Figure 11:
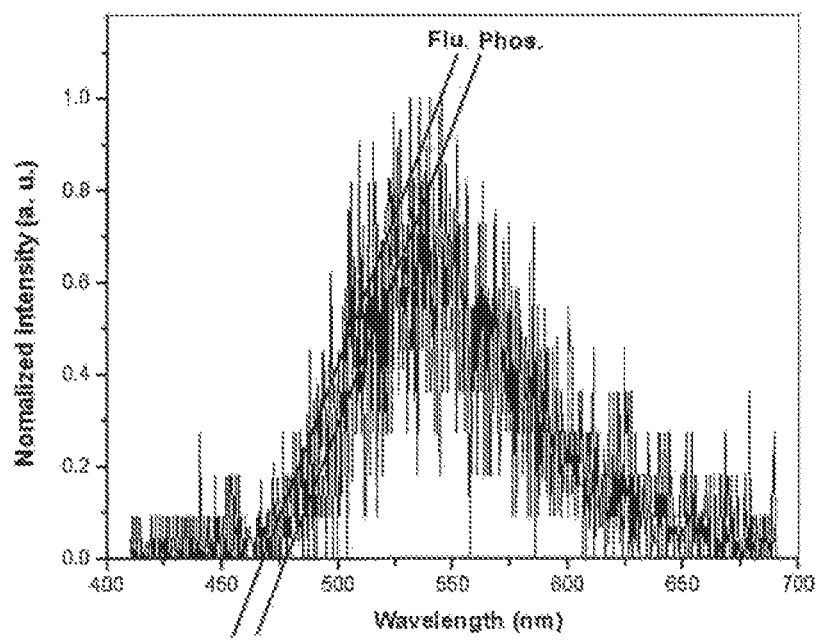
FIG. 11 shows the fluorescent spectrum and the phosphorescent spectrum of the thin film organic photoluminescent device of the compound 19 in Example 4.

FIG. 11 shows the fluorescent spectrum and the phosphorescent spectrum of the organic photoluminescent device having a thin film of the compound 19 with excitation light of 337 nm. The singlet energy $E_{S1}$ was 2.65 eV, the triplet energy $E_{T1}$ was 2.60 eV, and the difference $\Delta E_{ST}$ between the singlet energy $E_{S1}$ and the triplet energy $\Delta E_{T1}$ was 0.05 eV.

Figure 12:
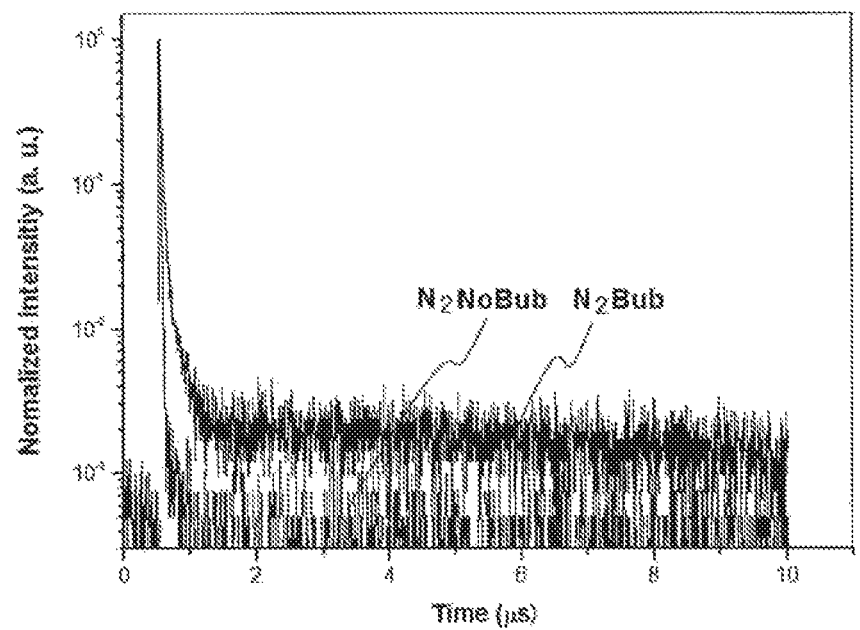
FIG. 12 shows the transient decay curve of the toluene solution of the compound 19 in Example 4.

FIG. 12 shows the transient decay curve of the toluene solution with excitation light of 340 nm. The light emission lifetime τ1 of the prompt fluorescent component was 54.5 ns, and the light emission lifetime τ2 of the delayed fluorescent component was 22.9 µs.

Figure 13:
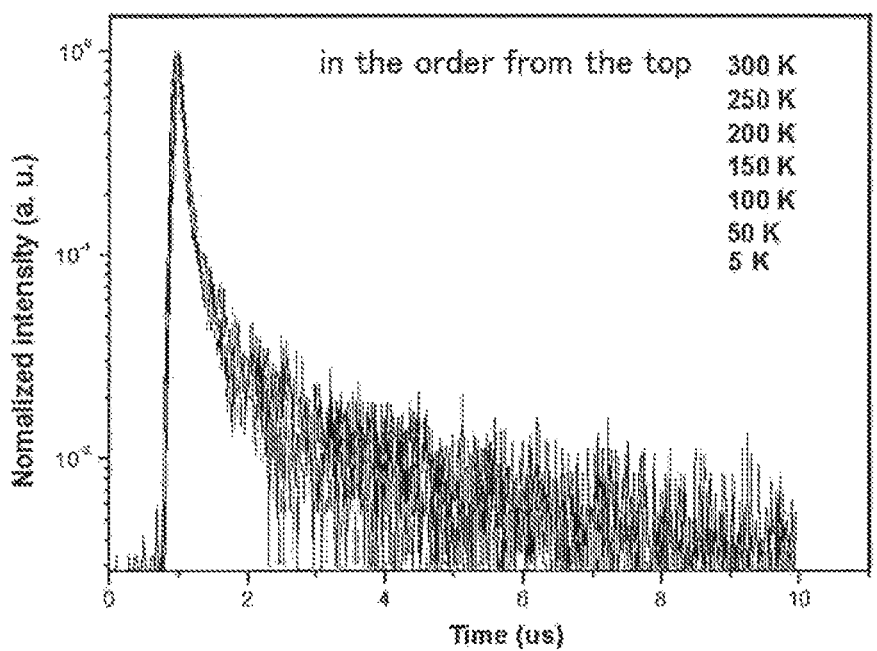
FIG. 13 shows the transient decay curves of the thin film organic photoluminescent device of the compound 19 in Example 4.
Figure 14:
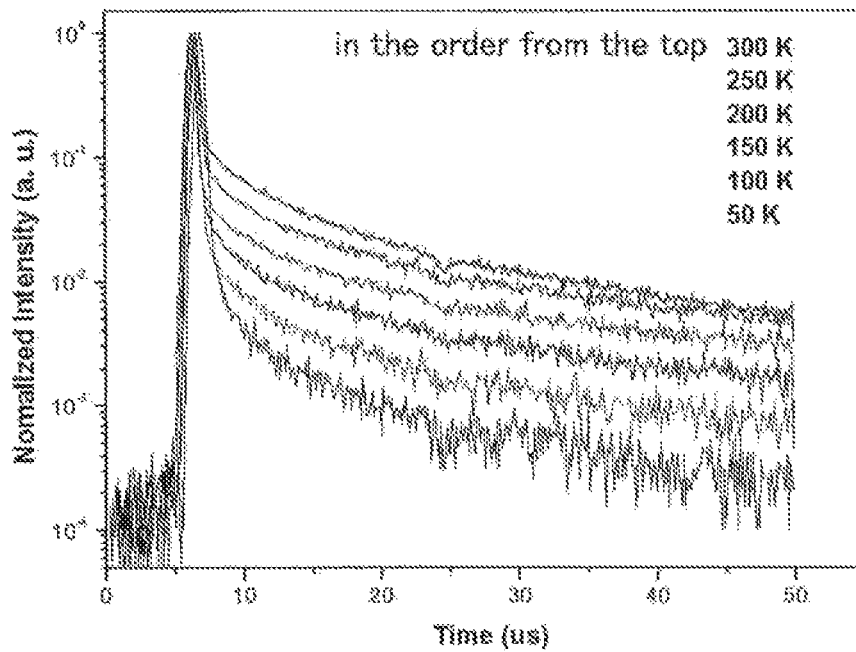
FIG. 14 shows the transient decay curves of the thin film organic photoluminescent device of the compound 19 and mCBP in Example 4.

FIG. 13 shows the transient decay curves of the organic photoluminescent device having a thin film of the compound 19 with excitation light of 337 nm, and FIG. 14 shows the transient decay curves of the organic photoluminescent device having a thin film of the compound 19 and mCBP with excitation light of 337 nm. The transient decay curves were measured under the conditions of 5K, 50 K, 100 K, 150 K, 200 K, 250 K, and 300 K, respectively. The light emission lifetime τ2 of the delayed fluorescent component at 300 K obtained from FIG. 14 was 37.9 ms.

It was confirmed from FIGS. 12 to 14 that the toluene solution of the compound 19 and the organic photoluminescent devices thereof emitted delayed fluorescent light, and in particular, it was confirmed from FIG. 14 that the compound 19 was a thermal activation type delayed fluorescent material (TADF).

Example 5

Production and Evaluation of Organic Photoluminescent Device Using Compound 20

A toluene solution of the compound 20, an organic photoluminescent device having a thin film of the compound 20, and an organic photoluminescent device having a thin film of the compound 20 and mCBP were provided in the same manner as in Example 4 except that the compound 20 was used instead of the compound 19.

Figure 15:
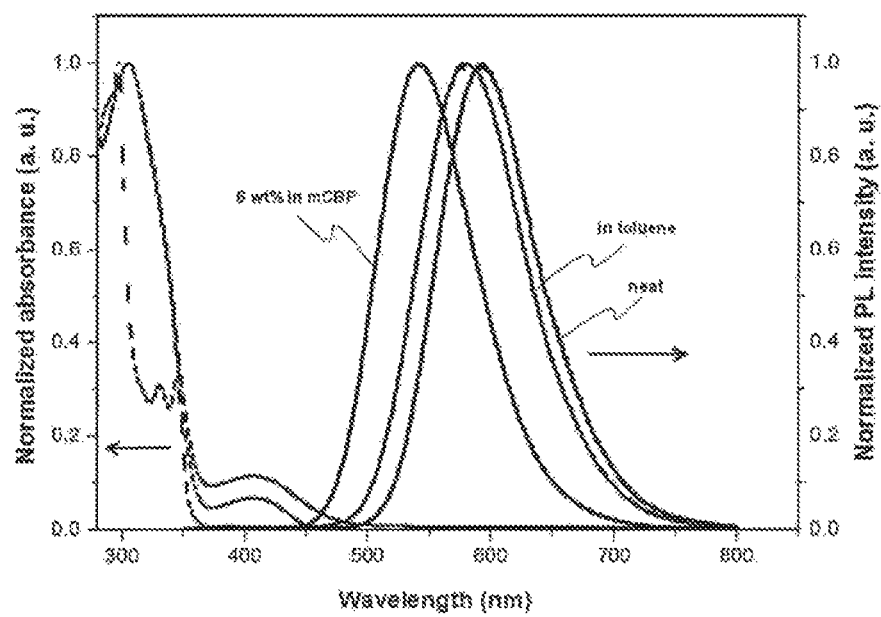
FIG. 15 shows the light emission spectra of the toluene solution of the compound 20, the thin film organic photoluminescent device of the compound 20, and the thin film organic photoluminescent device of the compound 20 and mCBP, in Example 5.

FIG. 15 shows the result of measurement of the light emission spectra of the toluene solution of the compound 20, the organic photoluminescent device having a thin film of the compound 20, and the organic photoluminescent device having a thin film of the compound 20 and mCBP, with excitation light of 350 nm.

The photoluminescence quantum efficiency with excitation light of 355 nm was 16.1% for the toluene solution with no bubbling, and 42.4% for the toluene solution bubbled with nitrogen. The photoluminescence quantum efficiency with excitation light of 375 nm was 18.8% for the organic photoluminescent device having a thin film of the compound 20 disposed in the air atmosphere, 20.8% therefor disposed in a nitrogen atmosphere, 64.5% for the organic photoluminescent device having a thin film of the compound 20 and mCBP disposed in the air atmosphere, and 77.2% therefor disposed in a nitrogen atmosphere.

Figure 16:
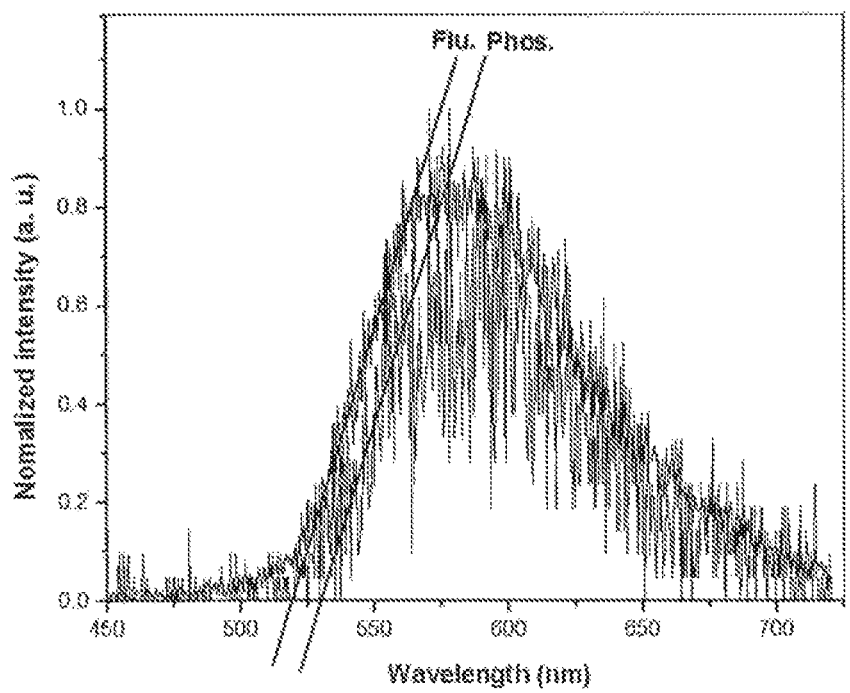
FIG. 16 shows the fluorescent spectrum and the phosphorescent spectrum of the thin film organic photoluminescent device of the compound 20 in Example 5.

FIG. 16 shows the fluorescent spectrum and the phosphorescent spectrum of the organic photoluminescent device having a thin film of the compound 20 with excitation light of 337 nm. The singlet energy $E_{S1}$ was 2.38 eV, the triplet energy $E_{T1}$ was 2.34 eV, and the difference $\Delta E_{ST}$ between the singlet energy $E_{S1}$ and the triplet energy $E_{T1}$ was 0.04 eV.

Figure 17:
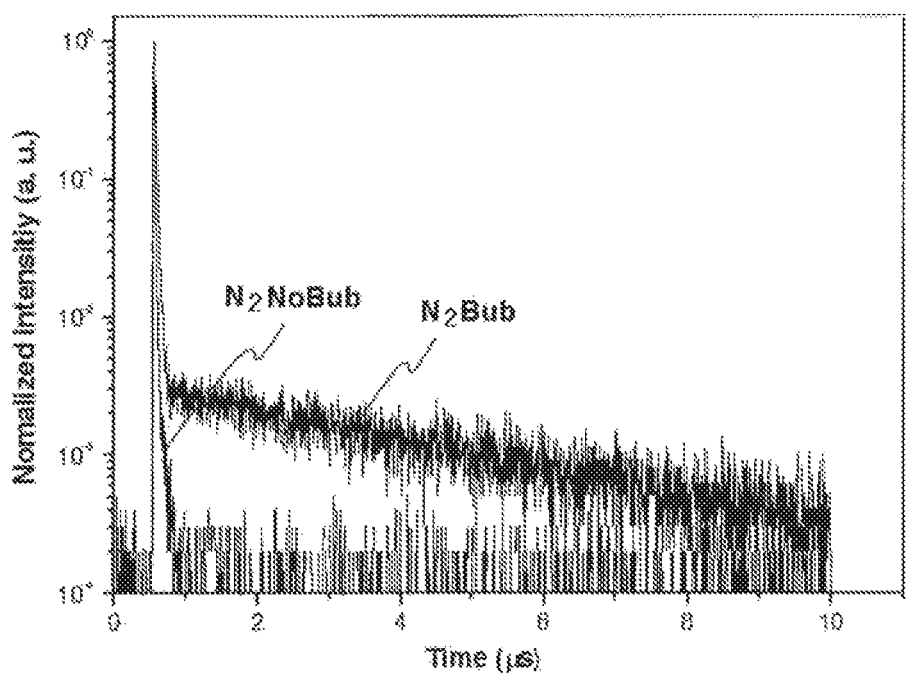
FIG. 17 shows the transient decay curves of the toluene solution of the compound 20 in Example 5.

FIG. 17 shows the transient decay curve of the toluene solution with excitation light of 340 nm. The light emission lifetime τ1 of the prompt fluorescent component was 46.4 ns, and the light emission lifetime τ2 of the delayed fluorescent component was 3.36 s.

Figure 18:
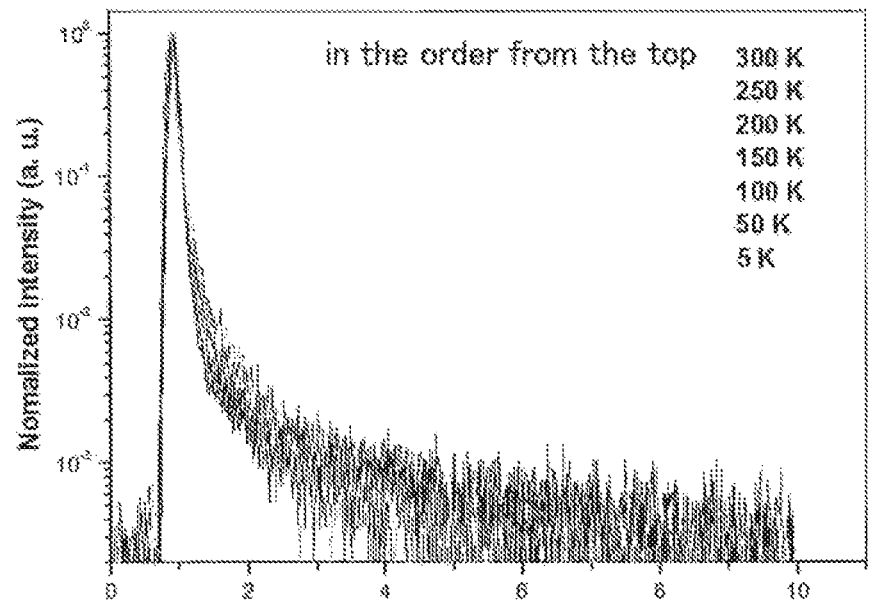
FIG. 18 shows the transient decay curves of the thin film organic photoluminescent device of the compound 20 in Example 5.
Figure 19:
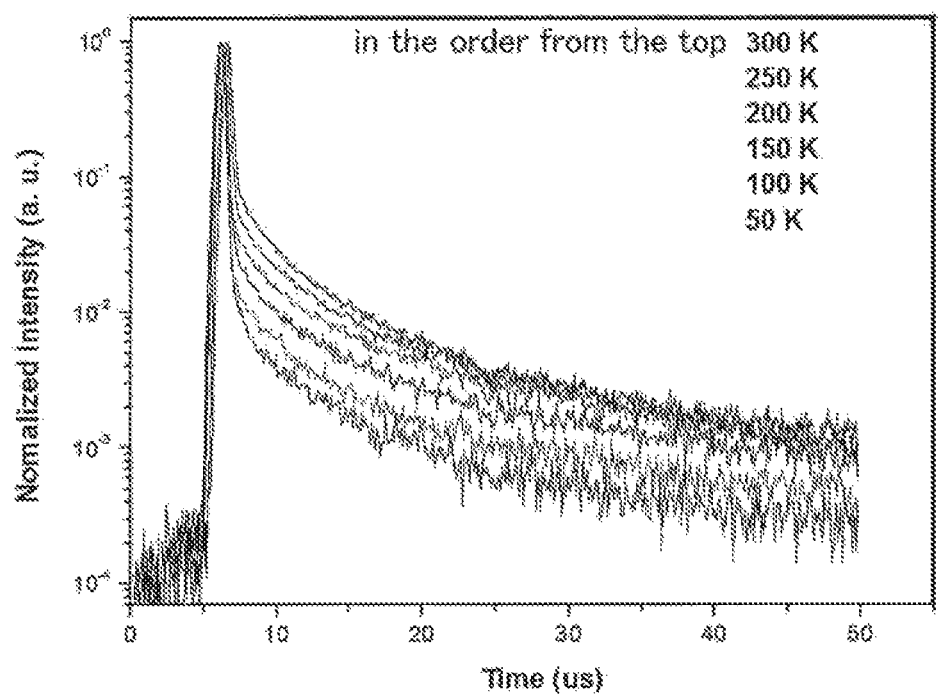
FIG. 19 shows the transient decay curves of the thin film organic photoluminescent device of the compound 20 and mCBP in Example 5.

FIG. 18 shows the transient decay curves of the organic photoluminescent device having a thin film of the compound 20 with excitation light of 337 nm, and FIG. 19 shows the transient decay curves of the organic photoluminescent device having a thin film of the compound 20 and mCBP with excitation light of 337 nm. The transient decay curves were measured under the conditions of 5K, 50 K, 100 K, 150 K, 200 K, 250 K, and 300 K, respectively. The light emission lifetime τ2 of the delayed fluorescent component at 300 K obtained from FIG. 19 was 202 µs.

It was confirmed from FIGS. 17 to 19 that the toluene solution of the compound 20 and the organic photoluminescent devices thereof emitted delayed fluorescent light, and in particular, it was confirmed from FIG. 19 that the compound 20 was a thermal activation type delayed fluorescent material (TADF)

Example 6

Production and Evaluation of Organic Photoluminescent Device Using Compound 30

A toluene solution of the compound 30, an organic photoluminescent device having a thin film of the compound 30, and an organic photoluminescent device having a thin film of the compound 30 and mCBP were provided in the same manner as in Example 4 except that the compound 30 was used instead of the compound 19.

Figure 20:
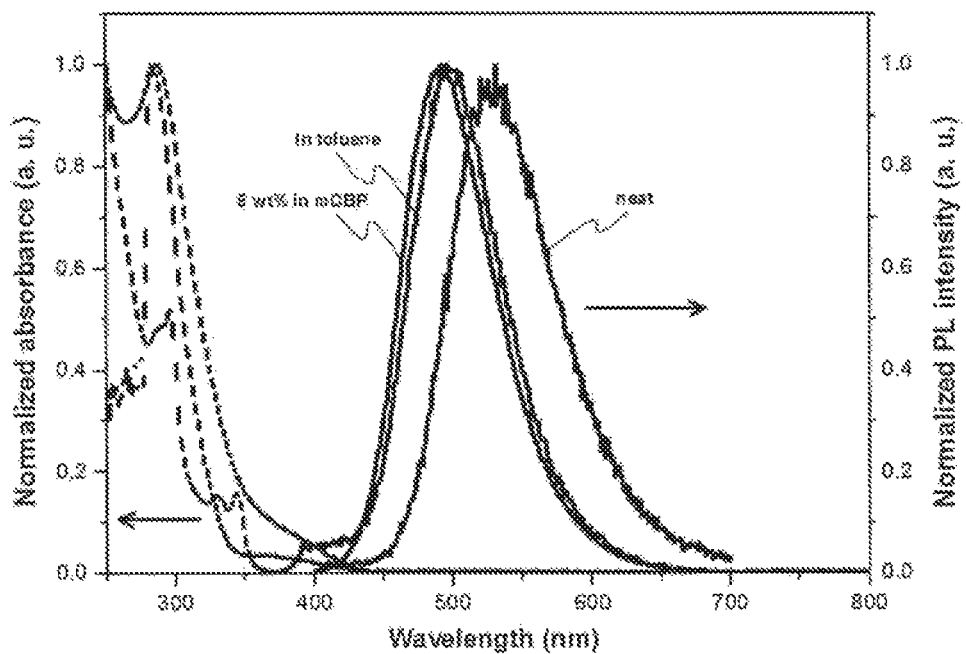
FIG. 20 shows the light emission spectra of the toluene solution of the compound 30, the thin film organic photoluminescent device of the compound 30, and the thin film organic photoluminescent device of the compound 30 and mCBP, in Example 6.

FIG. 20 shows the result of measurement of the light emission spectra of the toluene solution of the compound 30, the organic photoluminescent device having a thin film of the compound 30, and the organic photoluminescent device having a thin film of the compound 30 and mCBP, with excitation light of 350 nm.

The photoluminescence quantum efficiency with excitation light of 330 nm was 13.1% for the toluene solution with no bubbling, 28.4% for the toluene solution bubbled with nitrogen, 21.5% for the organic photoluminescent device having a thin film of the compound 30 disposed in the air atmosphere, 24.1% therefor disposed in a nitrogen atmosphere, 59.1% for the organic photoluminescent device having a thin film of the compound 30 and mCBP disposed in the air atmosphere, and 62.8% therefor disposed in a nitrogen atmosphere.

Figure 21:
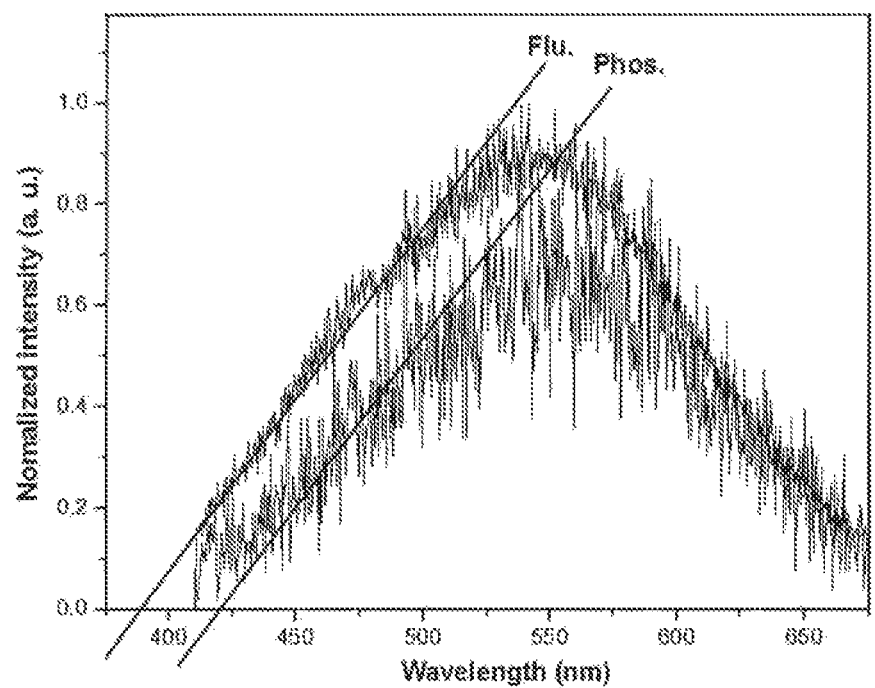
FIG. 21 shows the fluorescent spectrum and the phosphorescent spectrum of the thin film organic photoluminescent device of the compound 30 in Example 6.
Figure 22:
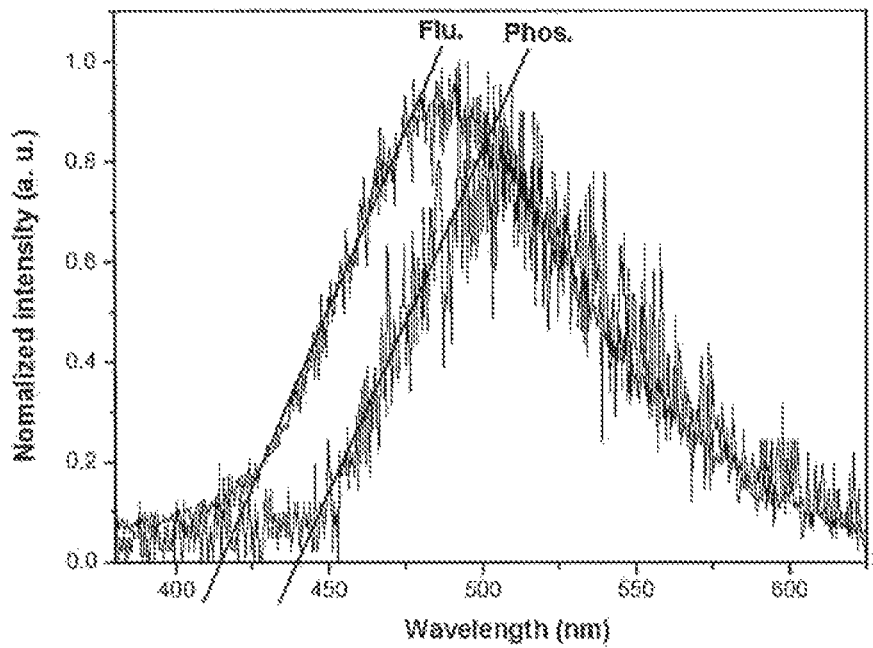
FIG. 22 shows the fluorescent spectrum and the phosphorescent spectrum of the thin film organic photoluminescent device of the compound 30 and mCBP in Example 6.

FIG. 21 shows the fluorescent spectrum and the phosphorescent spectrum of the organic photoluminescent device having a thin film of the compound 30 with excitation light of 337 nm. The singlet energy $E_{S1}$ was 3.10 eV, the triplet energy $E_{T1}$ was 2.95 eV, and the difference $\Delta E_{ST}$ between the singlet energy $E_{S1}$ and the triplet energy $E_{T1}$ was 0.15 eV. FIG. 22 shows the fluorescent spectrum and the phosphorescent spectrum of the organic photoluminescent device having a thin film of the compound 30 and mCBP with excitation light of 337 nm. The singlet energy $E_{S1}$ was 2.99 eV, the triplet energy $E_{T1}$ was 2.82 eV, and the difference $\Delta E_{ST}$ between the singlet energy $E_{S1}$ and the triplet energy $E_{T1}$ was 0.17 eV.

Figure 23:
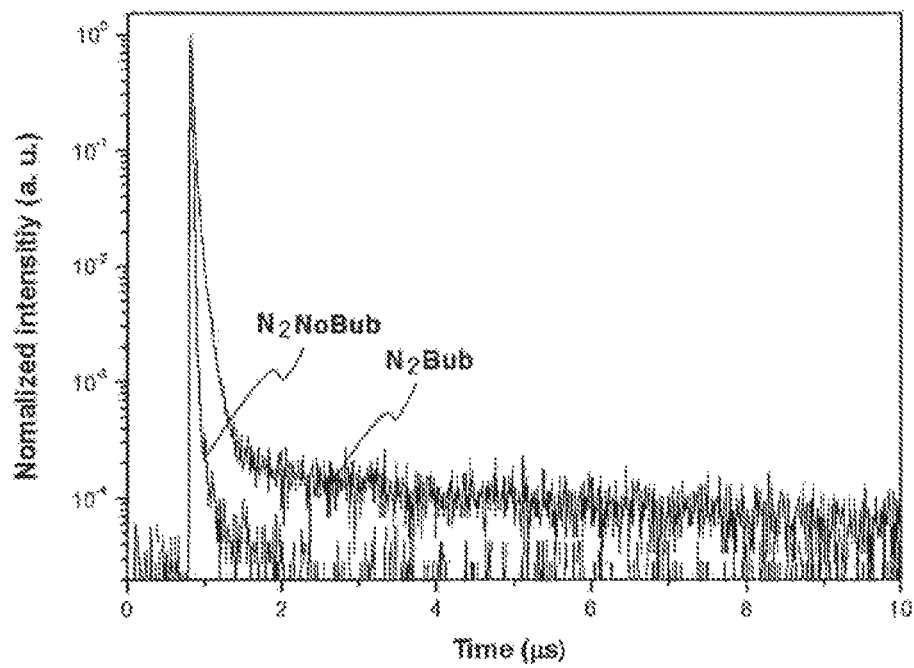
FIG. 23 shows the transient decay curves of the toluene solution of the compound 30 in Example 6.

FIG. 23 shows the transient decay curve of the toluene solution with excitation light of 340 nm. The light emission lifetime τ1 of the prompt fluorescent component was 26.4 ns, and the light emission lifetime τ2 of the delayed fluorescent component was 1.57 µs.

Figure 24:
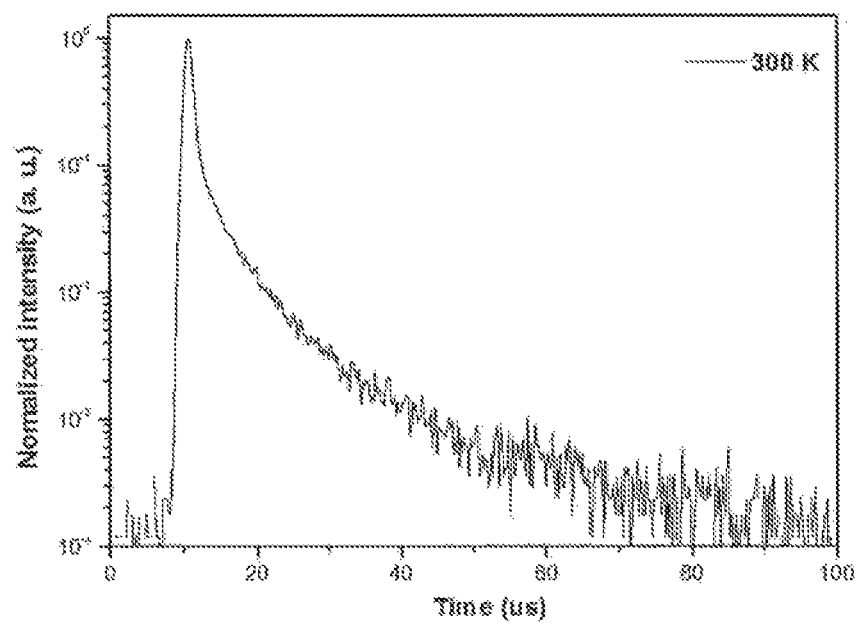
FIG. 24 shows the transient decay curve of the thin film organic photoluminescent device of the compound 30 in Example 6.
Figure 25:
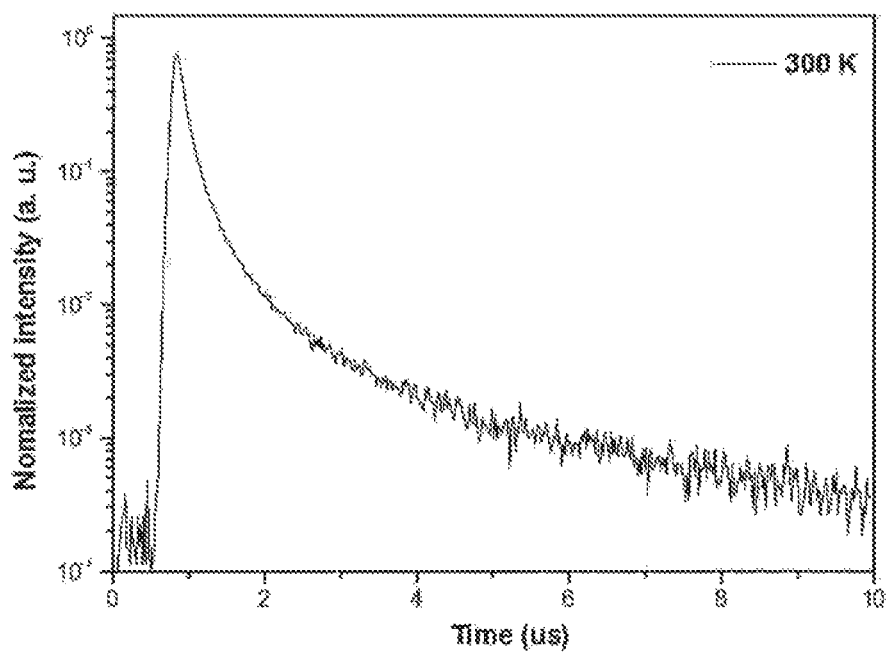
FIG. 25 shows the transient decay curve of the thin film organic photoluminescent device of the compound 30 and mCBP in Example 6.

FIG. 24 shows the transient decay curve of the organic photoluminescent device having a thin film of the compound 30 with excitation light of 337 nm, and FIG. 25 shows the transient decay curve of the organic photoluminescent device having a thin film of the compound 30 and mCBP with excitation light of 337 nm. The transient decay curves were measured at 300 K. The light emission lifetime τ2 of the delayed fluorescent component at 300 K obtained from FIG. 25 was 20.8 s.

It was confirmed from FIGS. 23 to 25 that the toluene solution of the compound 30 and the organic photoluminescent devices thereof emitted delayed fluorescent light.

Example 7

Production and Evaluation of Organic Photoluminescent Device Using Compound 31

A toluene solution of the compound 31, an organic photoluminescent device having a thin film of the compound 31, and an organic photoluminescent device having a thin film of the compound 31 and mCBP were provided in the same manner as in Example 4 except that the compound 31 was used instead of the compound 19.

Figure 26:
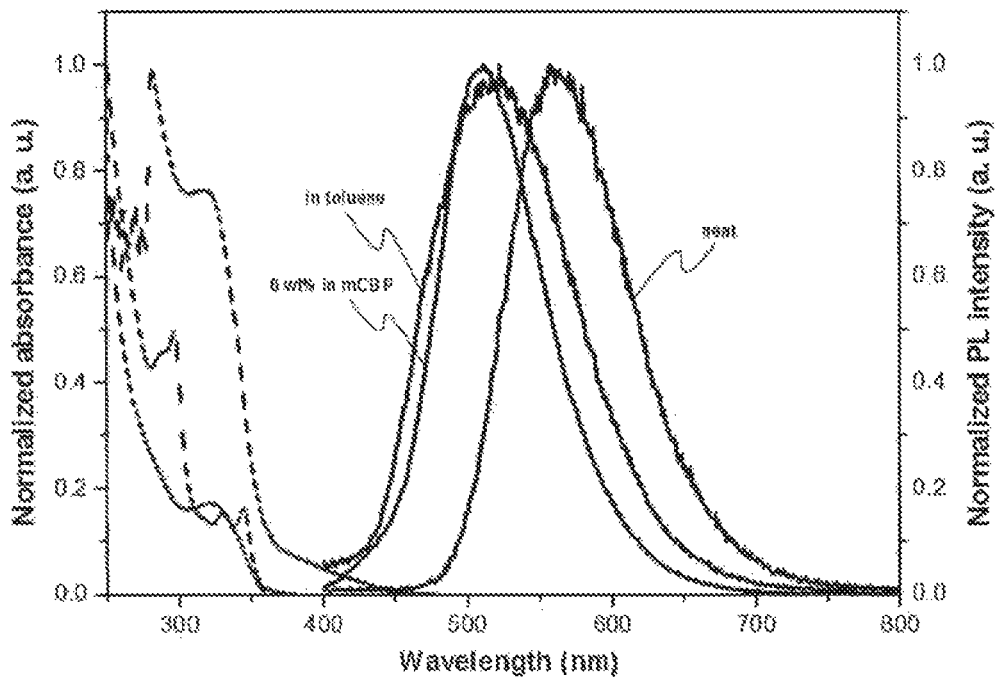
FIG. 26 shows the light emission spectra of the toluene solution of the compound 31, the thin film organic photoluminescent device of the compound 31, and the thin film organic photoluminescent device of the compound 31 and mCBP, in Example 7.

FIG. 26 shows the result of measurement of the light emission spectra of the toluene solution of the compound 31, the organic photoluminescent device having a thin film of the compound 31, and the organic photoluminescent device having a thin film of the compound 31 and mCBP, with excitation light of 350 nm.

The photoluminescence quantum efficiency with excitation light of 355 nm was 13.4% for the toluene solution with no bubbling, 42.5% for the toluene solution bubbled with nitrogen, 13.2% for the organic photoluminescent device having a thin film of the compound 31 disposed in the air atmosphere, 13.5% therefor disposed in a nitrogen atmosphere, 65.9% for the organic photoluminescent device having a thin film of the compound 31 and mCBP disposed in the air atmosphere, and 68.9% therefor disposed in a nitrogen atmosphere.

Figure 27:
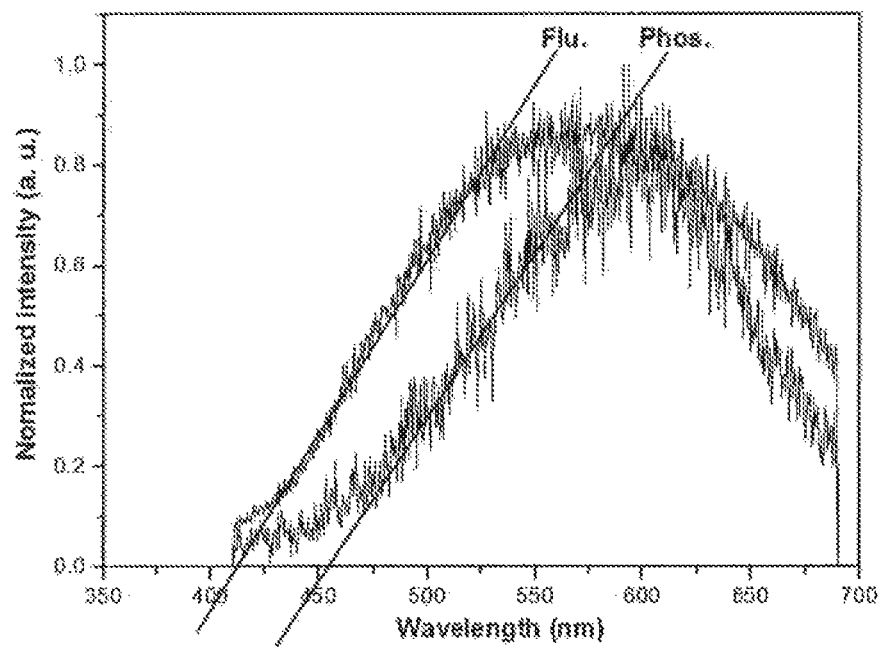
FIG. 27 shows the fluorescent spectrum and the phosphorescent spectrum of the thin film organic photoluminescent device of the compound 31 in Example 7.
Figure 28:
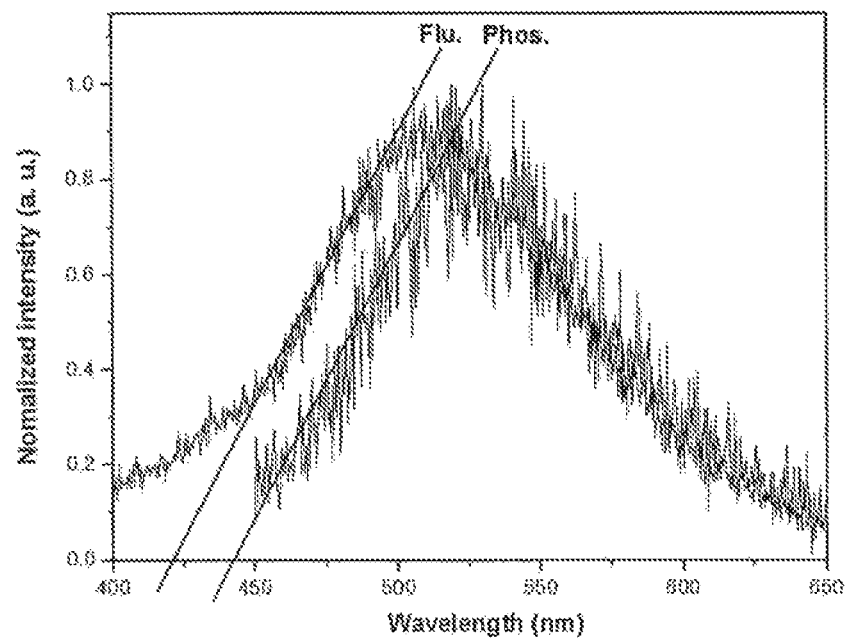
FIG. 28 shows the fluorescent spectrum and the phosphorescent spectrum of the thin film organic photoluminescent device of the compound 31 and mCBP in Example 7.

FIG. 27 shows the fluorescent spectrum and the phosphorescent spectrum of the organic photoluminescent device having a thin film of the compound 31 with excitation light of 337 nm. The singlet energy $E_{S1}$ was 3.00 eV, the triplet energy $E_{T1}$ was 2.73 eV, and the difference $\Delta E_{ST}$ between the singlet energy $E_{S1}$ and the triplet energy $E_{T1}$ was 0.27 eV. FIG. 28 shows the fluorescent spectrum and the phosphorescent spectrum of the organic photoluminescent device having a thin film of the compound 31 and mCBP with excitation light of 337 nm. The singlet energy $E_{S1}$ was 2.95 eV, the triplet energy $E_{T1}$ was 2.80 eV, and the difference $\Delta E_{ST}$ between the singlet energy $E_{S1}$ and the triplet energy $E_{T1}$ was 0.15 eV.

Figure 29:
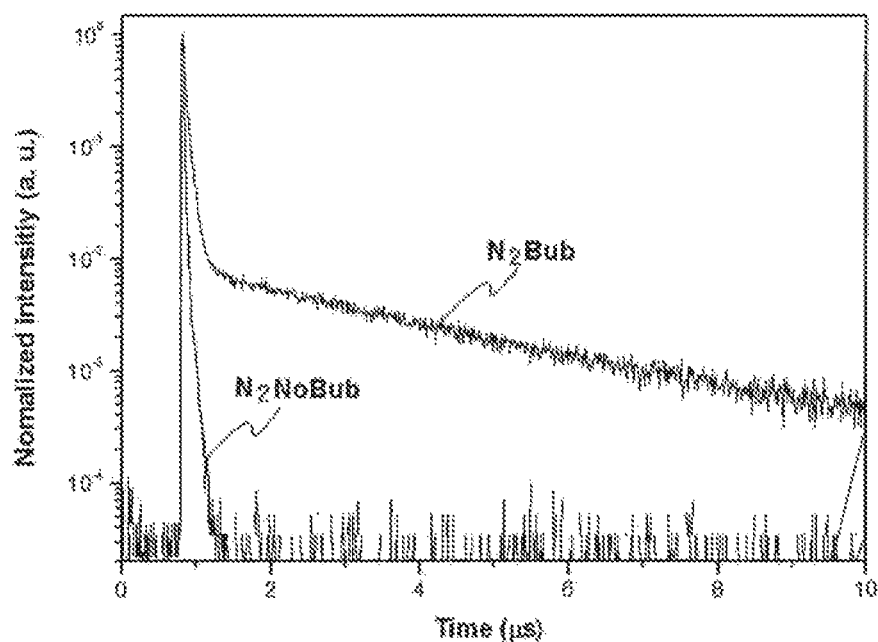
FIG. 29 shows the transient decay curves of the toluene solution of the compound 31 in Example 7.

FIG. 29 shows the transient decay curve of the toluene solution with excitation light of 340 nm. The light emission lifetime τ1 of the prompt fluorescent component was 28.9 ns, and the light emission lifetime τ2 of the delayed fluorescent component was 2.84 μs.

Figure 30:
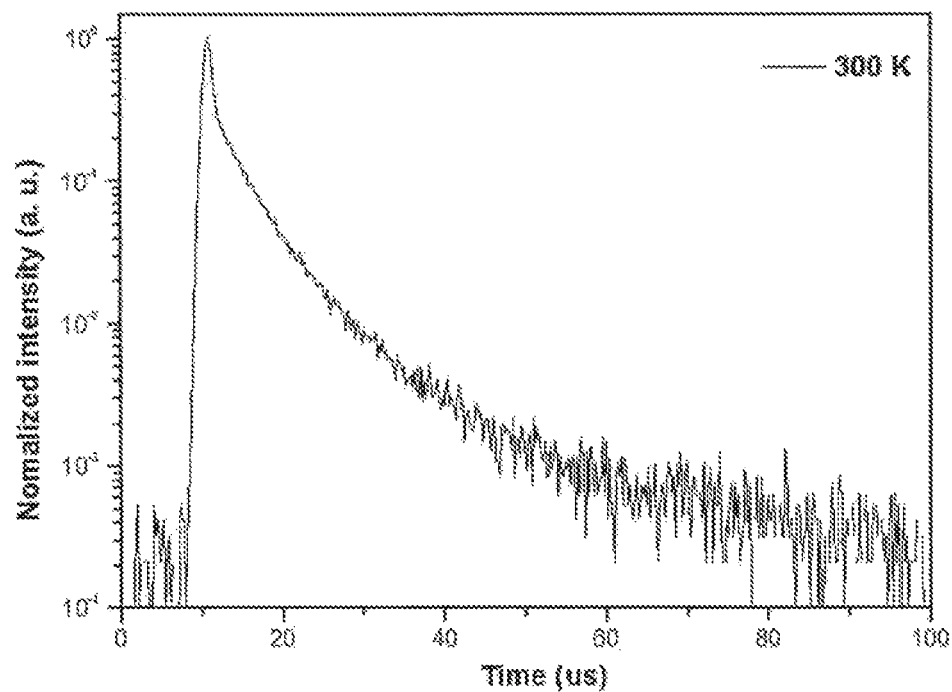
FIG. 30 shows the transient decay curve of the thin film organic photoluminescent device of the compound 31 in Example 7.
Figure 31:
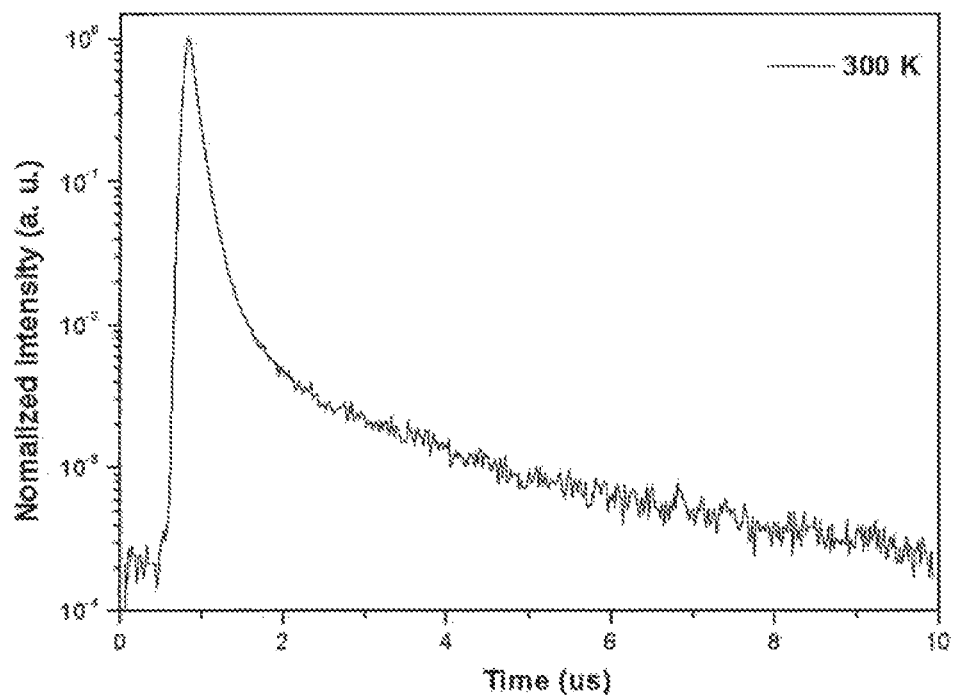
FIG. 31 shows the transient decay curve of the thin film organic photoluminescent device of the compound 31 and mCBP in Example 7.

FIG. 30 shows the transient decay curve of the organic photoluminescent device having a thin film of the compound 31 with excitation light of 337 nm, and FIG. 31 shows the transient decay curve of the organic photoluminescent device having a thin film of the compound 31 and mCBP with excitation light of 337 nm. The transient decay curves were measured at 300 K. The light emission lifetime τ2 of the delayed fluorescent component at 300 K obtained from FIG. 31 was 18.3 μs.

It was confirmed from FIGS. 29 to 31 that the toluene solution of the compound 31 and the organic photoluminescent devices thereof emitted delayed fluorescent light.

Example 8

Production and Evaluation of Organic Photoluminescent Device Using Compound 32

A toluene solution of the compound 32, an organic photoluminescent device having a thin film of the compound 32, and an organic photoluminescent device having a thin film of the compound 32 and PPF were provided in the same manner as in Example 4 except that the compound 32 was used instead of the compound 19, and PPF was used instead of mCBP.

Figure 32:
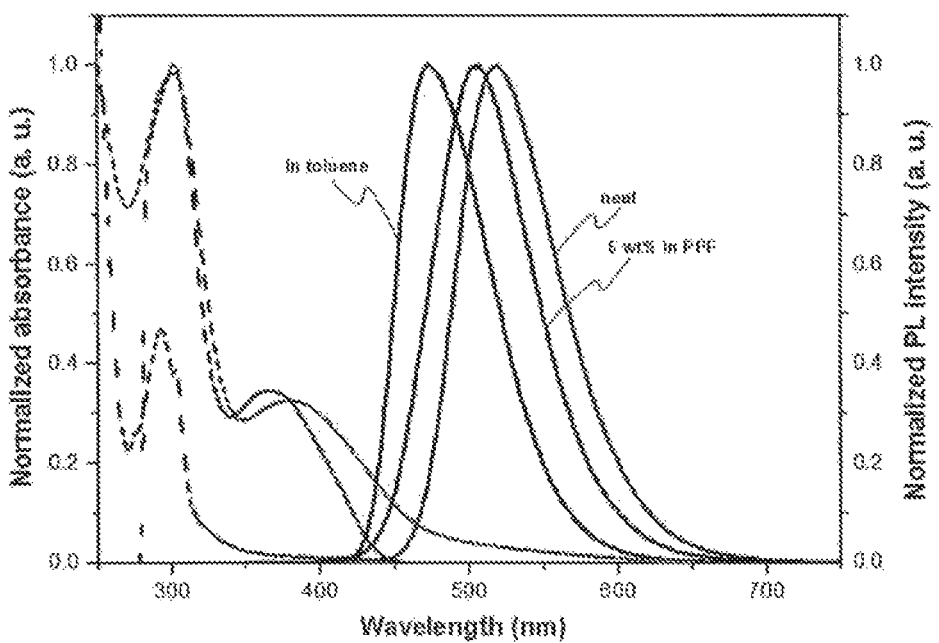
FIG. 32 shows the light emission spectra of the toluene solution of the compound 32, the thin film organic photoluminescent device of the compound 32, and the thin film organic photoluminescent device of the compound 32 and PPF, in Example 8.

FIG. 32 shows the result of measurement of the light emission spectra of the toluene solution of the compound 32, the organic photoluminescent device having a thin film of the compound 32, and the organic photoluminescent device having a thin film of the compound 32 and PPF, with excitation light of 350 nm.

The photoluminescence quantum efficiency with excitation light of 335 nm was 73.4% for the toluene solution with no bubbling, 96.5% for the toluene solution bubbled with nitrogen, 68.1% for the organic photoluminescent device having a thin film of the compound 32 disposed in the air atmosphere, and 71.7% therefor disposed in a nitrogen atmosphere. The photoluminescence quantum efficiency with excitation light of 310 nm was 87.3% for the organic photoluminescent device having a thin film of the compound 32 and PPF disposed in the air atmosphere, and 95.6% therefor disposed in a nitrogen atmosphere.

Figure 33:
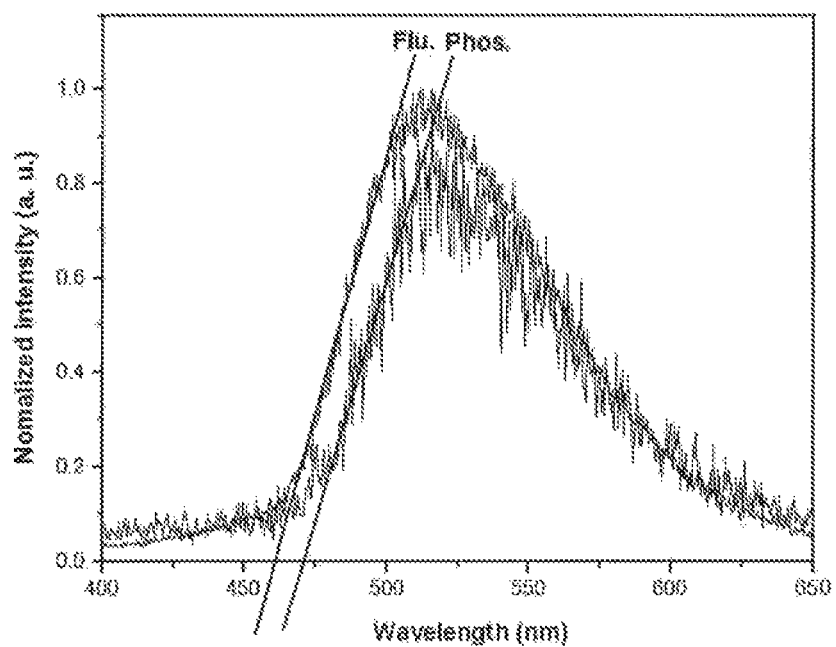
FIG. 33 shows the fluorescent spectrum and the phosphorescent spectrum of the thin film organic photoluminescent device of the compound 32 in Example 8.

FIG. 33 shows the fluorescent spectrum and the phosphorescent spectrum of the organic photoluminescent device having a thin film of the compound 32 with excitation light of 337 nm. The singlet energy $E_{S1}$ was 2.70 eV, the triplet energy $E_{T1}$ was 2.63 eV, and the difference $\Delta E_{ST}$ between the singlet energy $E_{s1}$ and the triplet energy $E_{T1}$ was 0.07 eV.

Figure 34:
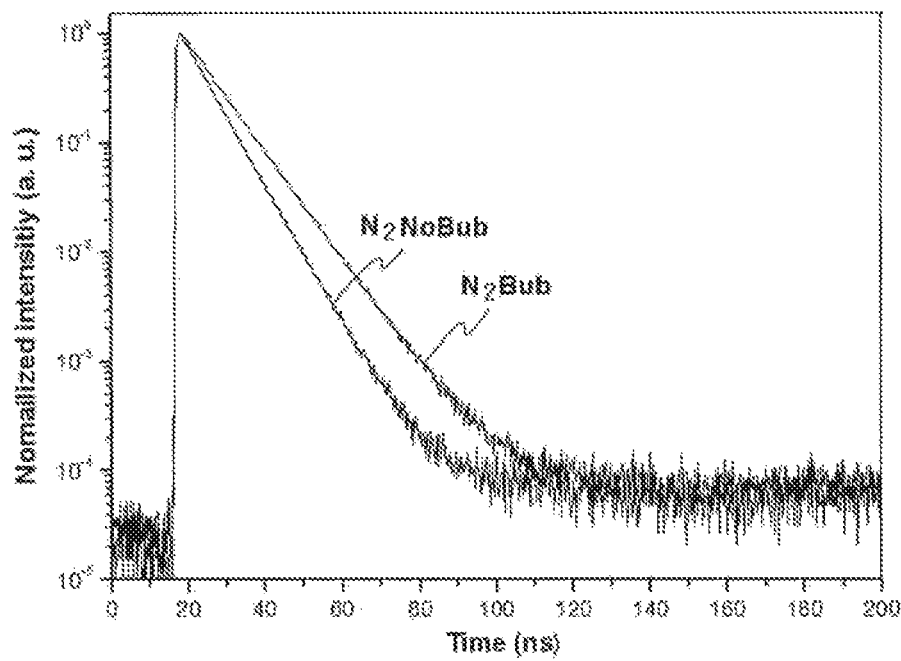
FIG. 34 shows the transient decay curves of the toluene solution of the compound 32 in Example 8.

FIG. 34 shows the transient decay curve of the toluene solution with excitation light of 340 nm. The light emission lifetime τ1 of the prompt fluorescent component was 8.69 ns, and the light emission lifetime τ2 of the delayed fluorescent component was 93.09 ns.

Figure 35:
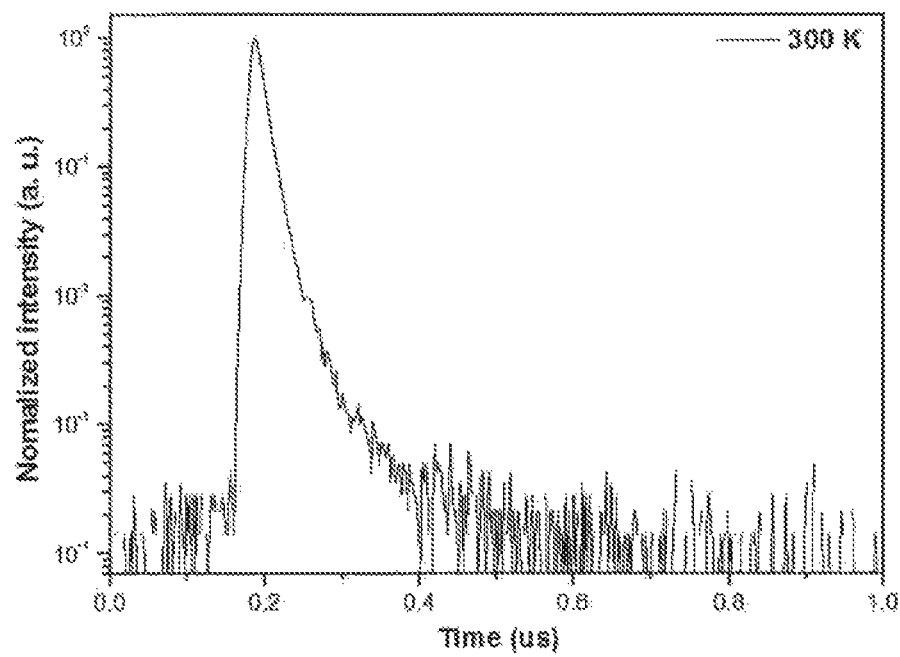
FIG. 35 shows the transient decay curve of the thin film organic photoluminescent device of the compound 32 in Example 8.
Figure 36:
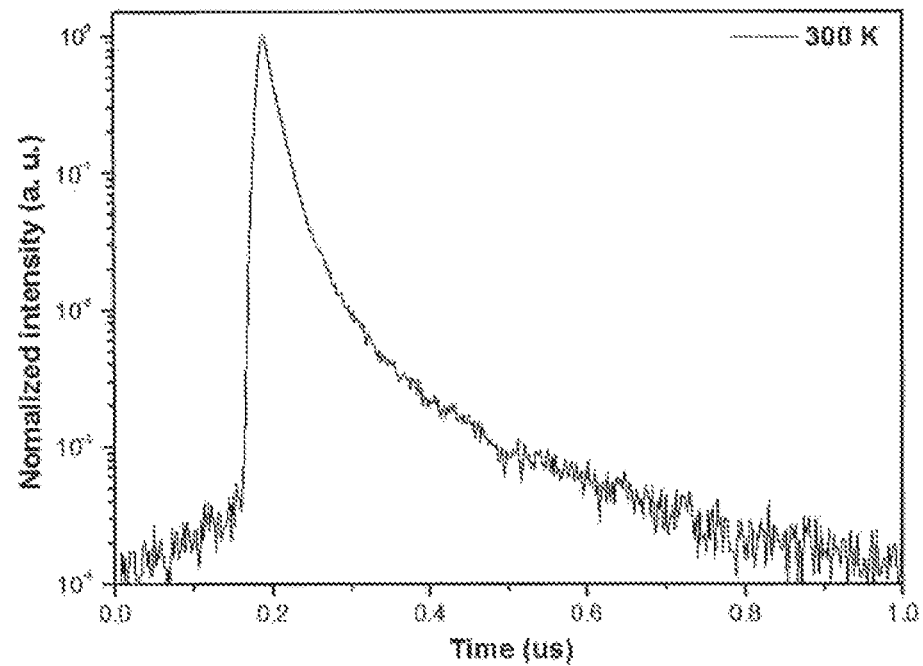
FIG. 36 shows the transient decay curve of the thin film organic photoluminescent device of the compound 32 and PPF in Example 8.

FIG. 35 shows the transient decay curve of the organic photoluminescent device having a thin film of the compound 32 with excitation light of 337 nm, and FIG. 36 shows the transient decay curve of the organic photoluminescent device having a thin film of the compound 32 and PPF with excitation light of 337 nm. The transient decay curves were measured at 300 K. The light emission lifetime τ1 of the prompt fluorescent component at 300 K obtained from FIG. 36 was 9.39 nm, and the light emission lifetime τ2 of the delayed fluorescent component at 300 K obtained therefrom was 150 ns.

It was confirmed from FIGS. 34 to 36 that the toluene solution of the compound 32 and the organic photoluminescent devices thereof emitted delayed fluorescent light.

Example 9

Production and Evaluation of Organic Electroluminescent Device Using Compound 1

Thin films were laminated on a glass substrate having formed thereon an anode formed of indium tin oxide (ITO) having a thickness of 100 nm, by a vacuum vapor deposition method at a vacuum degree of $5.0 \times 10^{-4}$ Pa. Firstly, α-NPD was formed to a thickness of 35 nm on ITO, and then mCP was formed to a thickness of 10 nm thereon. Subsequently, the compound 1 and PzCz were co-deposited thereon from separate vapor deposition sources to form a layer having a thickness of 15 nm, which was designated as a light-emitting layer. At this time, the concentration of the compound 1 was 3.0% by weight. PPT was then formed to a thickness of 40 nm, further lithium fluoride (LiF) was vacuum vapor-deposited to a thickness of 0.8 nm, and then aluminum (Al) was vapor-deposited to a thickness of 80 nm to form a cathode, thereby completing an organic electroluminescent device.

Figure 37:
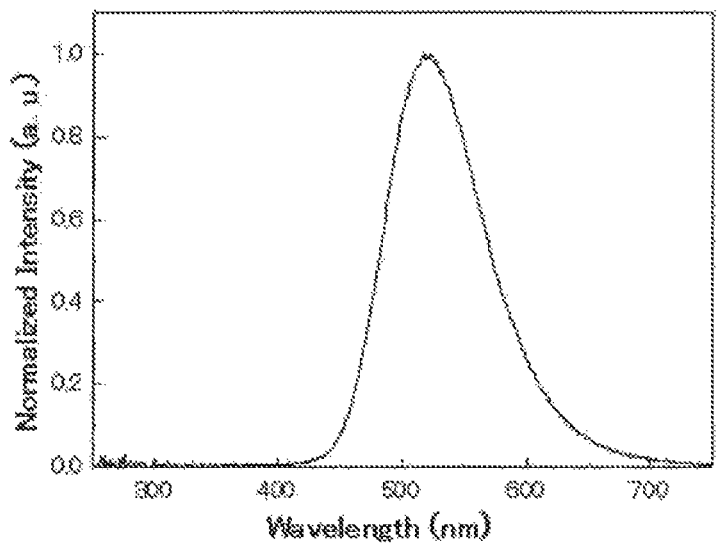
FIG. 37 shows the light emission spectrum of the organic electroluminescent device of the compound 1 in Example 9.
Figure 38:
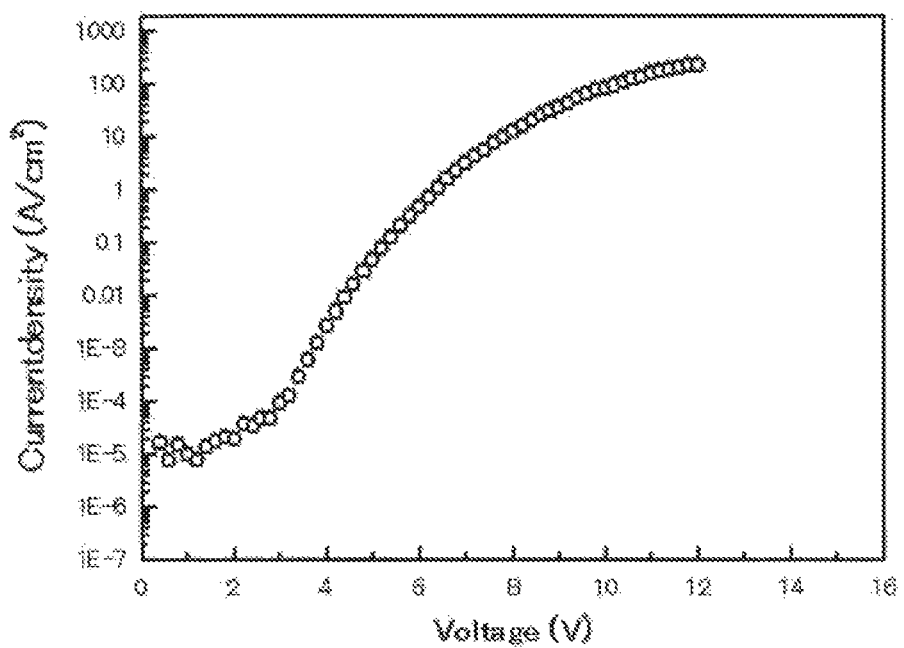
FIG. 38 is a graph showing the voltage-current density characteristics of the organic electroluminescent device of the compound 1 in Example 9.
Figure 39:
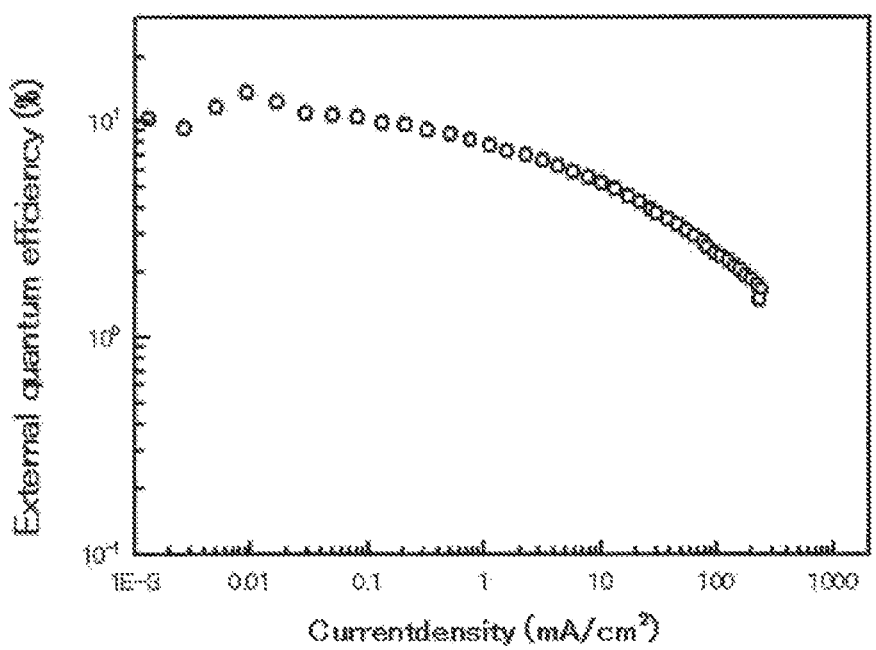
FIG. 39 is a graph showing the current density-external quantum efficiency characteristics of the organic electroluminescent device of the compound 1 in Example 9.

FIG. 37 shows the light emission spectrum of the organic electroluminescent device thus produced, FIG. 38 shows the voltage-current density characteristics thereof, and FIG. 39 shows current density-external quantum efficiency characteristics thereof. The organic electroluminescent device using the compound 1 achieved a high external quantum efficiency of 13.4%. If an ideally balanced organic electroluminescent device is produced by using a fluorescent material having a light emission quantum efficiency of 100%, the external quantum efficiency of the fluorescent light emission may be from 5 to 7.5% assuming that the light extraction efficiency is from 20 to 30%. It has been ordinarily considered that this value is the theoretical limit value of an external quantum efficiency of an organic electroluminescent device using a fluorescent material. Accordingly, the organic electroluminescent device of the invention using the compound 1 is considerably excellent in such a point that a high external quantum efficiency that exceeds the theoretical limit value is achieved.

Example 10

Production and Evaluation of Additional Organic Electroluminescent Device Using Compound 1

Thin films were laminated on a glass substrate having formed thereon an anode formed of indium tin oxide (ITO) having a thickness of 100 nm, by a vacuum vapor deposition method at a vacuum degree of $5.0 \times 10^{-4}$ Pa. Firstly, α-NPD was formed to a thickness of 25 nm on ITO, and then Tris-PCz was formed to a thickness of 10 nm thereon. Subsequently, the compound 1 and mCBP were co-deposited thereon from separate vapor deposition sources to form a layer having a thickness of 15 nm, which was designated as a light-emitting layer. At this time, the concentration of the compound 1 was 6.0% by weight. PPT was then formed to a thickness of 10 nm, and then TPBi was formed to a thickness of 40 nm. Lithium fluoride (LiF) was further vacuum vapor-deposited to a thickness of 0.8 nm, and then aluminum (Al) was vapor-deposited to a thickness of 80 nm to form a cathode, thereby completing an organic electroluminescent device.

Figure 40:
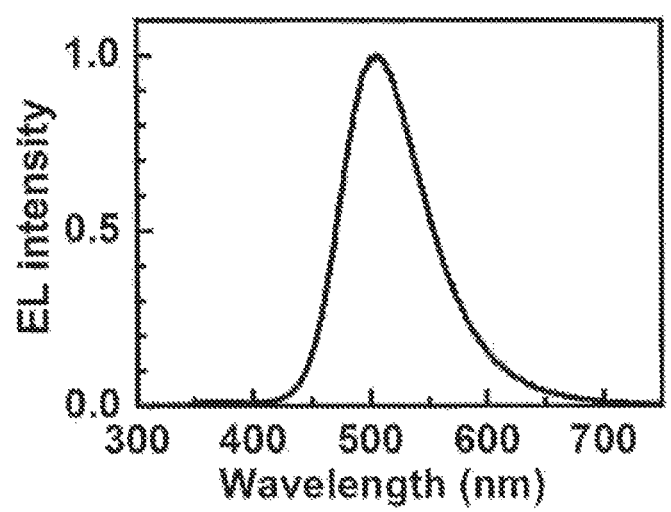
FIG. 40 shows the light emission spectrum of the additional organic electroluminescent device of the compound 1 in Example 10.
Figure 41:
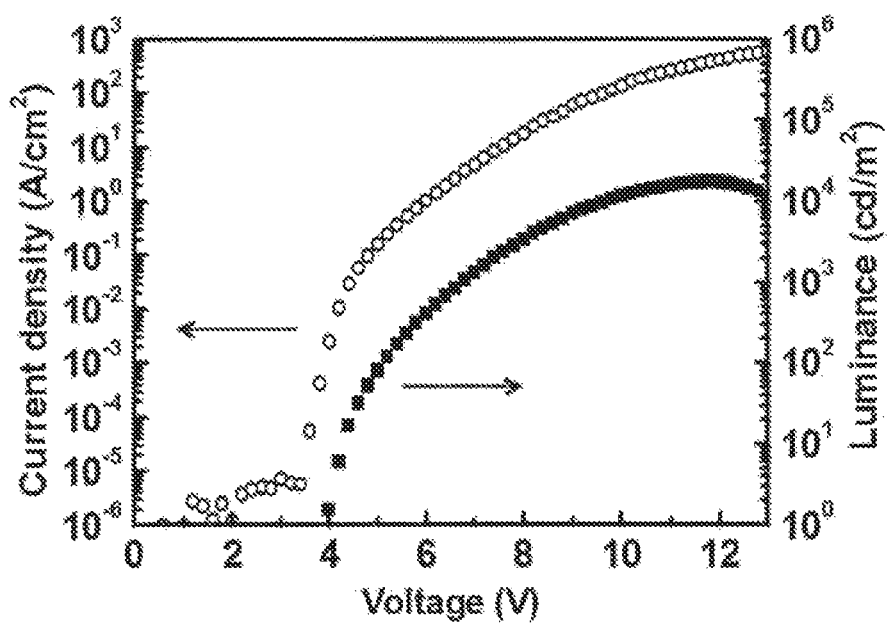
FIG. 41 is a graph showing the voltage-current density-luminance characteristics of the additional organic electroluminescent device of the compound 1 in Example 10.
Figure 42:
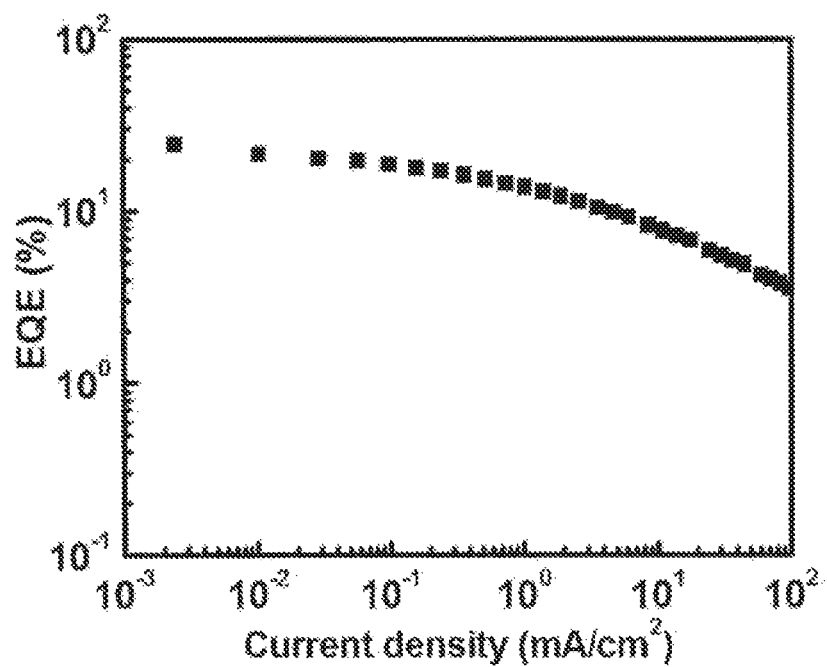
FIG. 42 is a graph showing the current density-external quantum efficiency characteristics of the additional organic electroluminescent device of the compound 1 in Example 10.

FIG. 40 shows the light emission spectrum of the organic electroluminescent device thus produced, FIG. 41 shows the voltage-current density-luminance characteristics thereof, FIG. 42 shows current density-external quantum efficiency characteristics thereof, and the device characteristics thus measured are shown in Table 1. The organic electroluminescent device using the compound 1 as a light-emitting material achieved a high external quantum efficiency of 21.3%.

Example 11

Production and Evaluation of Organic Electroluminescent Device Using Compound 2

Thin films were laminated on a glass substrate having formed thereon an anode formed of indium tin oxide (ITO) having a thickness of 100 nm, by a vacuum vapor deposition method at a vacuum degree of $5.0 \times 10^{-4}$ Pa. Firstly, α-NPD was formed to a thickness of 35 nm on ITO. Subsequently, the compound 2 and CBP were co-deposited thereon from separate vapor deposition sources to form a layer having a thickness of 15 nm, which was designated as a light-emitting layer. At this time, the concentration of the compound 2 was 6.0% by weight. PPT was then formed to a thickness of 10 nm, TPBi was formed to a thickness of 40 nm, further lithium fluoride (LiF) was vacuum vapor-deposited to a thickness of 0.8 nm, and then aluminum (Al) was vapor-deposited to a thickness of 80 nm to form a cathode, thereby completing an organic electroluminescent device.

Figure 43:
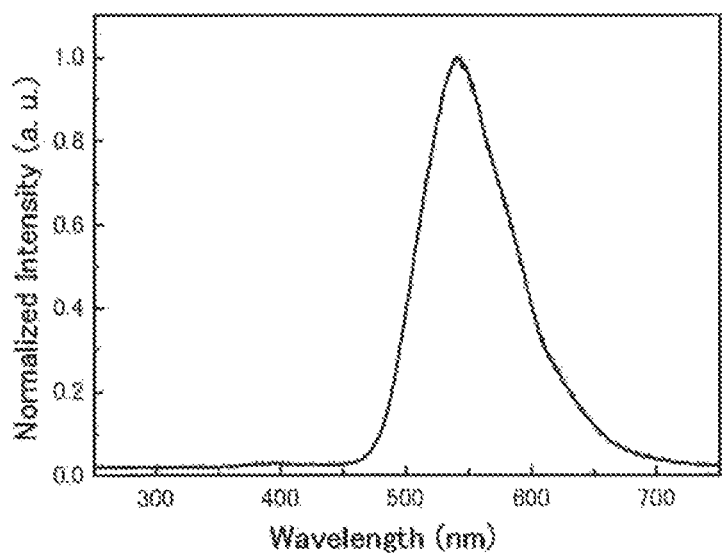
FIG. 43 shows the light emission spectrum of the organic electroluminescent device of the compound 2 in Example 11.
Figure 44:
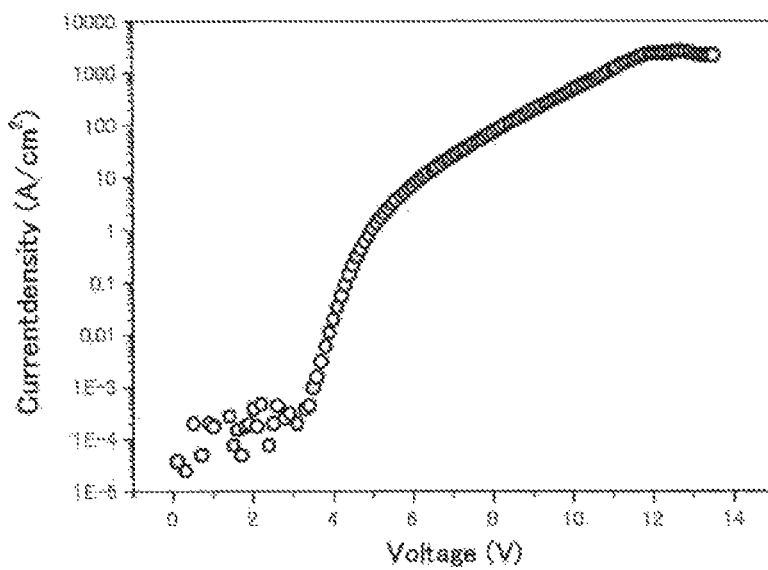
FIG. 44 is a graph showing the voltage-current density characteristics of the organic electroluminescent device of the compound 2 in Example 11.
Figure 45:
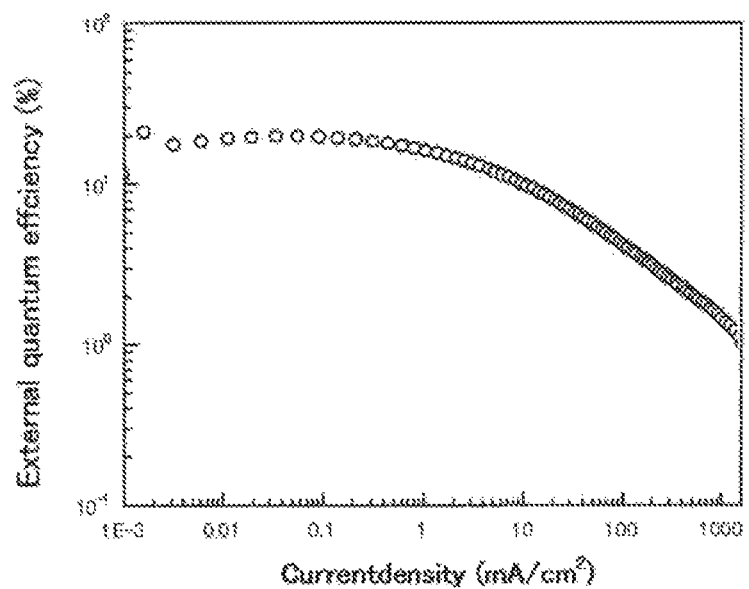
FIG. 45 is a graph showing the current density-external quantum efficiency characteristics of the organic electroluminescent device of the compound 2 in Example 11.

FIG. 43 shows the light emission spectrum of the organic electroluminescent device thus produced, FIG. 44 shows the voltage-current density characteristics thereof, and FIG. 45 shows current density-external quantum efficiency characteristics thereof. The organic electroluminescent device using the compound 2 as a light-emitting material achieved a high external quantum efficiency of 19.9%.

Example 12

Production and Evaluation of Additional Organic Electroluminescent Device Using Compound 2

Thin films were laminated on a glass substrate having formed thereon an anode formed of indium tin oxide (ITO) having a thickness of 100 nm, by a vacuum vapor deposition method at a vacuum degree of $5.0 \times 10^{-4}$ Pa. Firstly, α-NPD was formed to a thickness of 35 nm on ITO. Subsequently, the compound 2 and CBP were co-deposited thereon from separate vapor deposition sources to form a layer having a thickness of 15 nm, which was designated as a light-emitting layer. At this time, the concentration of the compound 2 was 6.0% by weight. PPT was then formed to a thickness of 10 nm, and then TPBi was formed to a thickness of 40 nm. Lithium fluoride (LiF) was further vacuum vapor-deposited to a thickness of 0.8 nm, and then aluminum (Al) was vapor-deposited to a thickness of 80 nm to form a cathode, thereby completing an organic electroluminescent device.

Figure 46:
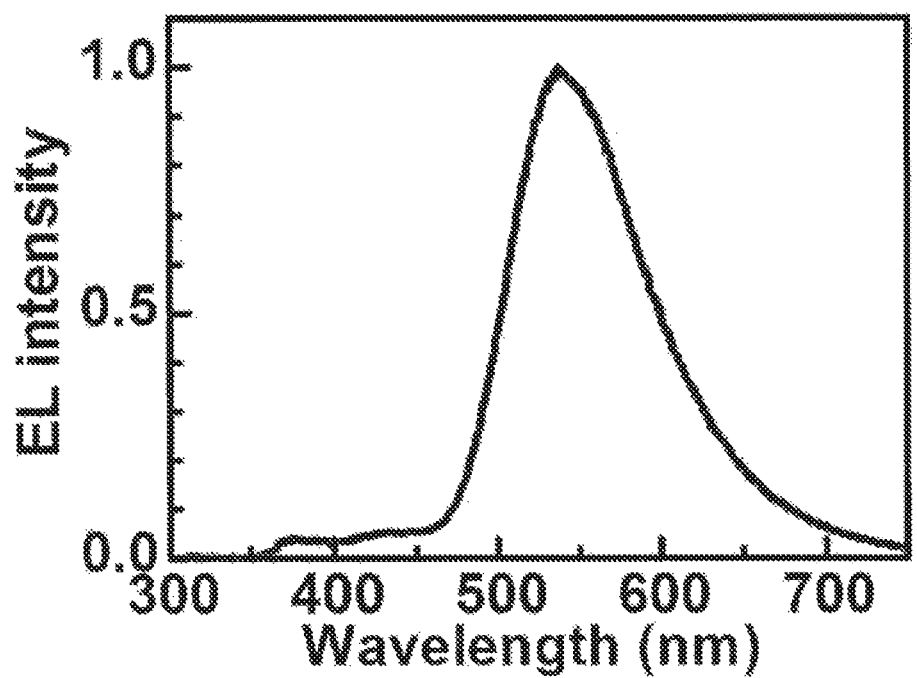
FIG. 46 shows the light emission spectrum of the additional organic electroluminescent device of the compound 2 in Example 12.
Figure 47:
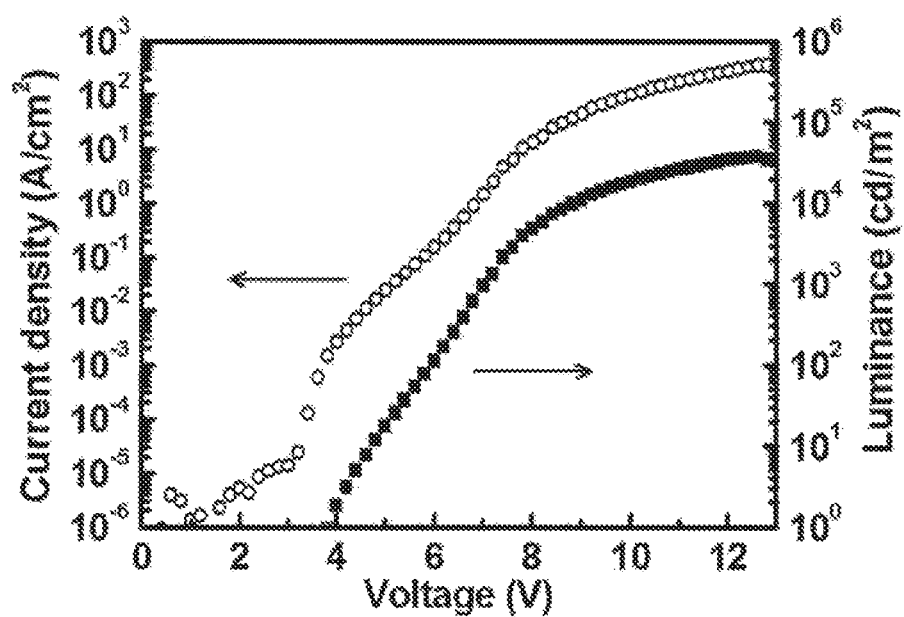
FIG. 47 is a graph showing the voltage-current density-luminance characteristics of the additional organic electroluminescent device of the compound 2 in Example 12.
Figure 48:
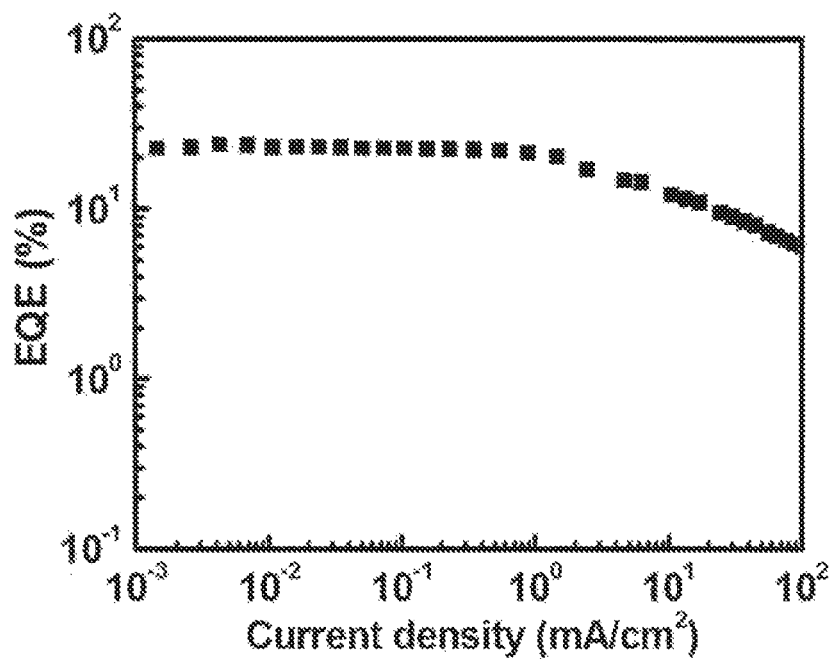
FIG. 48 is a graph showing the current density-external quantum efficiency characteristics of the additional organic electroluminescent device of the compound 2 in Example 12.

FIG. 46 shows the light emission spectrum of the organic electroluminescent device thus produced, FIG. 47 shows the voltage-current density-luminance characteristics thereof, FIG. 48 shows current density-external quantum efficiency characteristics thereof, and the device characteristics thus measured are shown in Table 1. The organic electroluminescent device using the compound 2 as a light-emitting material achieved a high external quantum efficiency of 23.1%.

Example 13

Production and Evaluation of Organic Electroluminescent Device Using Compound 19

Thin films were laminated on a glass substrate having formed thereon an anode formed of indium tin oxide (ITO) having a thickness of 110 nm, by a vacuum vapor deposition method at a vacuum degree of $5.0 \times 10^{-4}$ Pa. Firstly, α-NPD was formed to a thickness of 40 nm on ITO, and then mCP was formed to a thickness of 10 nm thereon. Subsequently, the compound 19 and mCBP were co-deposited thereon from separate vapor deposition sources to form a layer having a thickness of 20 nm, which was designated as a light-emitting layer. At this time, the concentration of the compound 19 was 6.0% by weight. PPF was then formed to a thickness of 10 nm, and then TPBi was formed to a thickness of 30 nm thereon. Lithium fluoride (LiF) was further vacuum vapor-deposited to a thickness of 0.8 nm, and then aluminum (Al) was vapor-deposited to a thickness of 80 nm to form a cathode, thereby completing an organic electroluminescent device.

Figure 49:
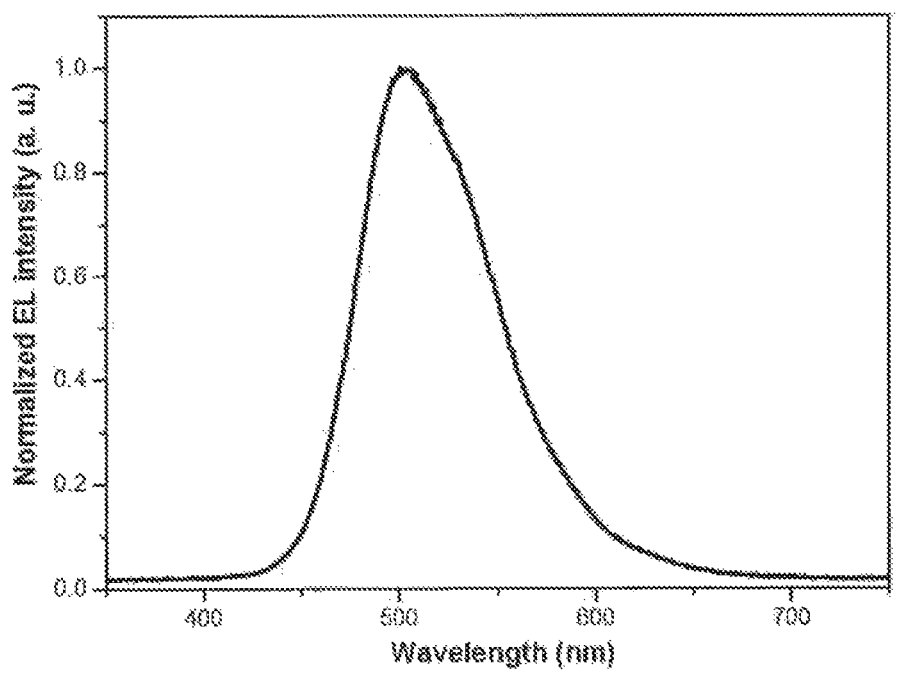
FIG. 49 shows the light emission spectrum of the organic electroluminescent device of the compound 19 in Example 13.
Figure 50:
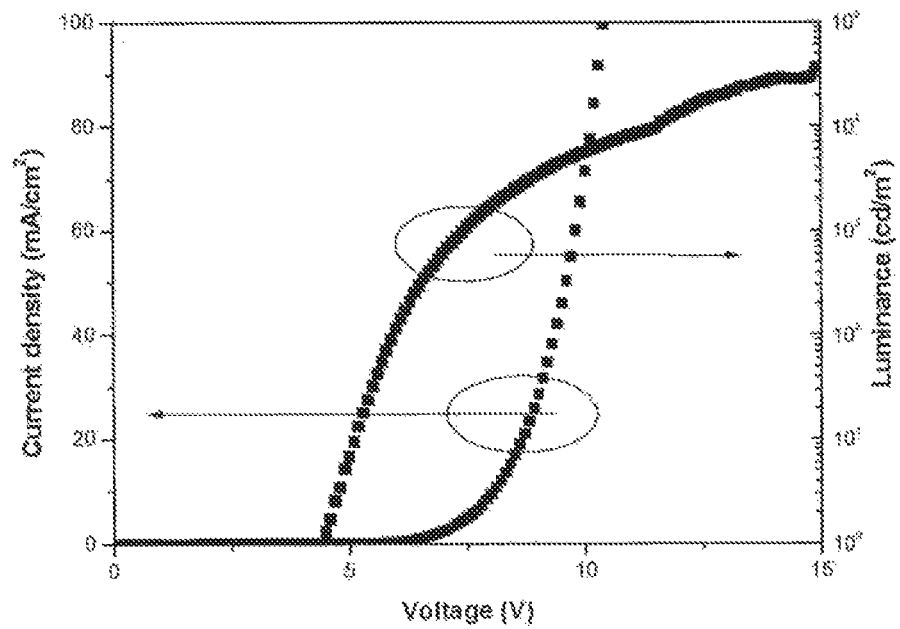
FIG. 50 is a graph showing the voltage-current density-luminance characteristics of the organic electroluminescent device of the compound 19 in Example 13.
Figure 51:
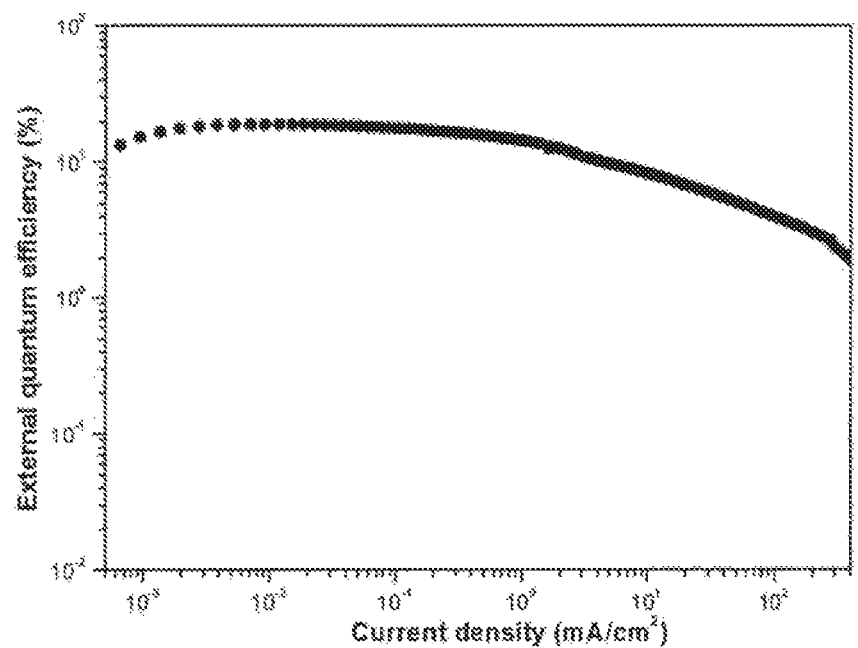
FIG. 51 is a graph showing the current density-external quantum efficiency characteristics of the organic electroluminescent device of the compound 19 in Example 13.

FIG. 49 shows the light emission spectrum at 10 mA/cm² of the organic electroluminescent device thus produced, FIG. 50 shows the voltage-current density-luminance characteristics thereof, and FIG. 51 shows current density-external quantum efficiency characteristics thereof. The organic electroluminescent device using the compound 19 as a light-emitting material achieved a high external quantum efficiency of 18.09%.

Example 14

Production and Evaluation of Organic Electroluminescent Device Using Compound 20

An organic electroluminescent device was produced in the same manner as in Example 13 except that the compound 20 was used instead of the compound 19 in the formation of the light-emitting layer.

Figure 52:
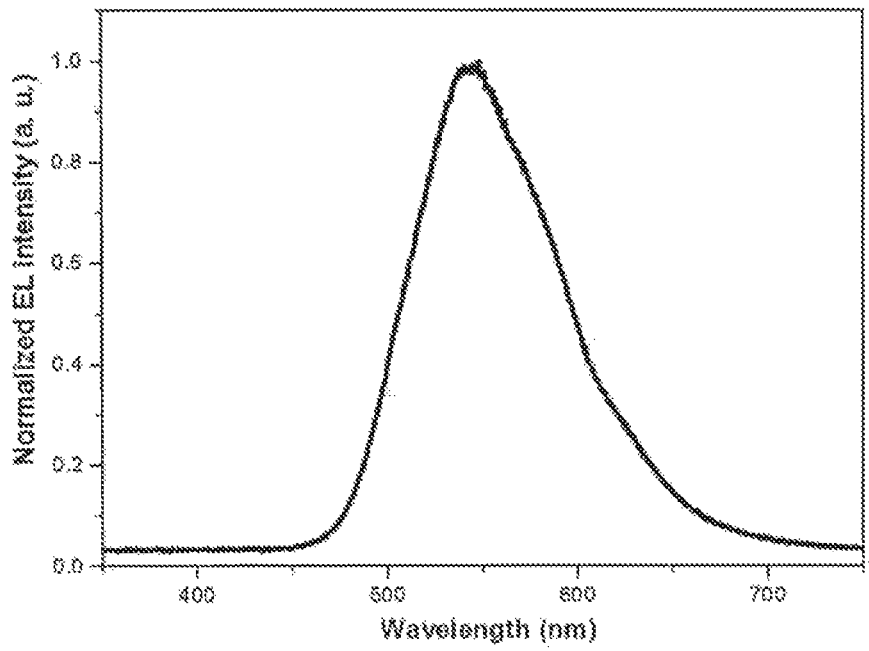
FIG. 52 shows the light emission spectrum of the organic electroluminescent device of the compound 20 in Example 14.
Figure 53:
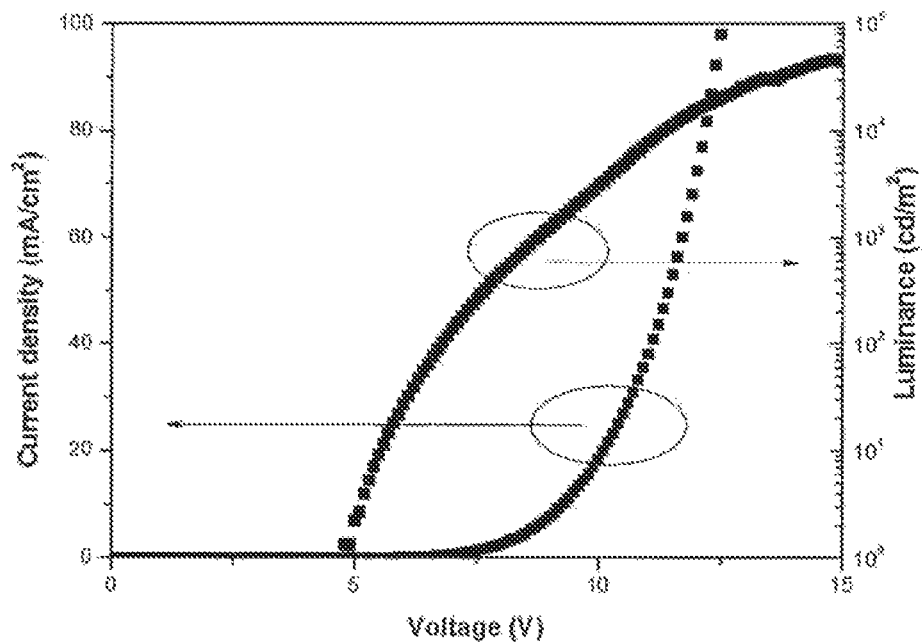
FIG. 53 is a graph showing the voltage-current density-luminance characteristics of the organic electroluminescent device of the compound 20 in Example 14.
Figure 54:
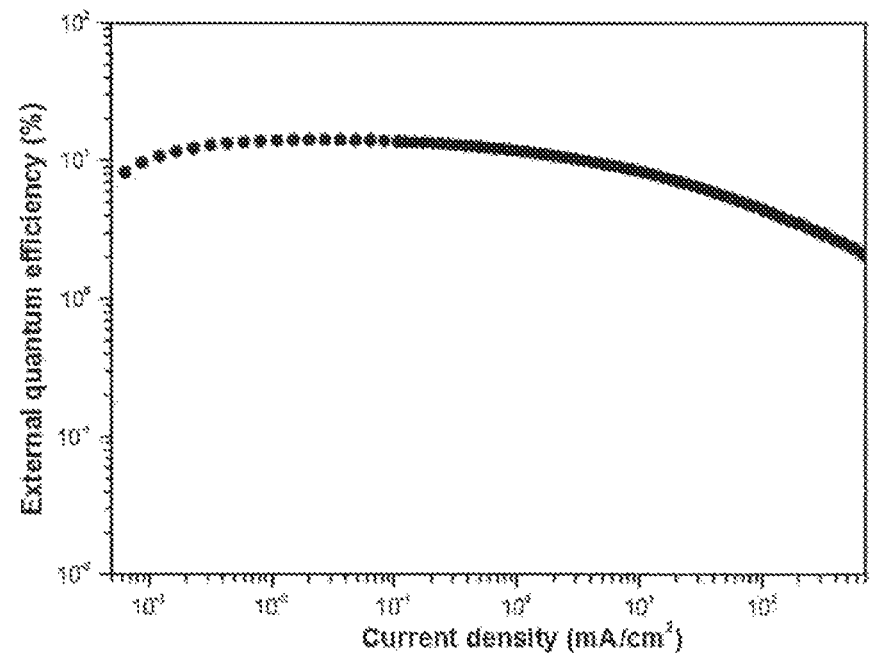
FIG. 54 is a graph showing the current density-external quantum efficiency characteristics of the organic electroluminescent device of the compound 20 in Example 14.

FIG. 52 shows the light emission spectrum at 10 mA/cm$^2$ of the organic electroluminescent device thus produced, FIG. 53 shows the voltage-current density-luminance characteristics thereof, and FIG. 54 shows current density-external quantum efficiency characteristics thereof. The organic electroluminescent device using the compound 20 as a light-emitting material achieved a high external quantum efficiency of 14.25%.

Example 15

Production and Evaluation of Organic Electroluminescent Device Using Compound 21

Thin films were laminated on a glass substrate having formed thereon an anode formed of indium tin oxide (ITO) having a thickness of 100 nm, by a vacuum vapor deposition method at a vacuum degree of 5.0×10$^{-4}$ Pa. Firstly, TAPC was formed to a thickness of 40 nm on ITO, and then mCBP was formed to a thickness of 15 nm thereon. Subsequently, the compound 21, mCBP, and BmPyPhB were co-deposited thereon from separate vapor deposition sources to form a layer having a thickness of 30 nm, which was designated as a light-emitting layer. At this time, the concentration of the compound 21 was 6.0% by weight. BmPyPhB was then formed to a thickness of 50 nm. Lithium fluoride (LiF) was further vacuum vapor-deposited to a thickness of 0.8 nm, and then aluminum (Al) was vapor-deposited to a thickness of 80 nm to form a cathode, thereby completing an organic electroluminescent device.

Figure 55:
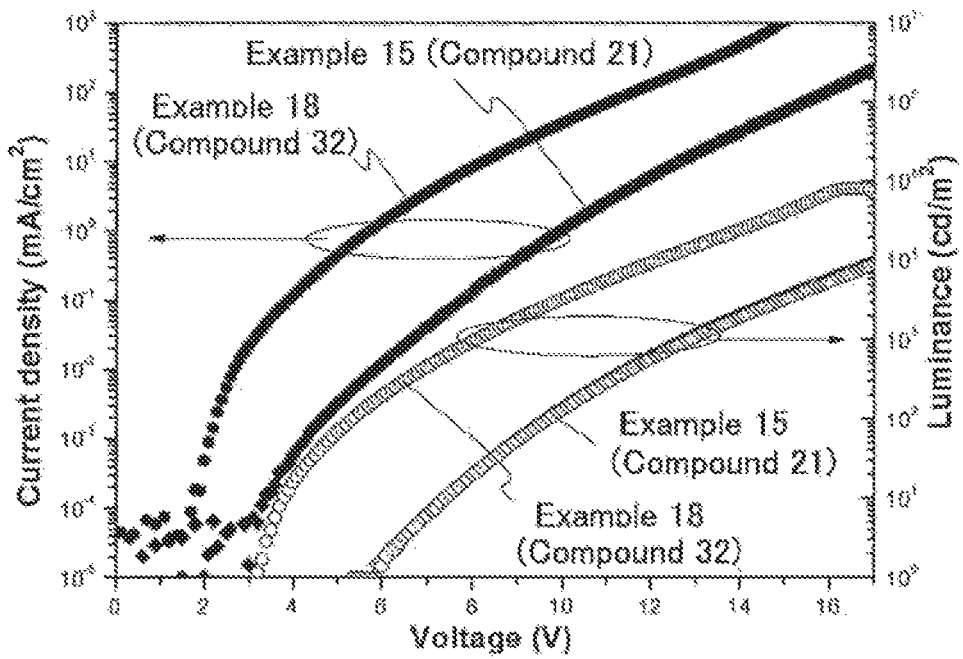
FIG. 55 is a graph showing the voltage-current density-luminance characteristics of the organic electroluminescent devices of the compound 21 in Example 15 and the compound 32 in Example 18.
Figure 56:
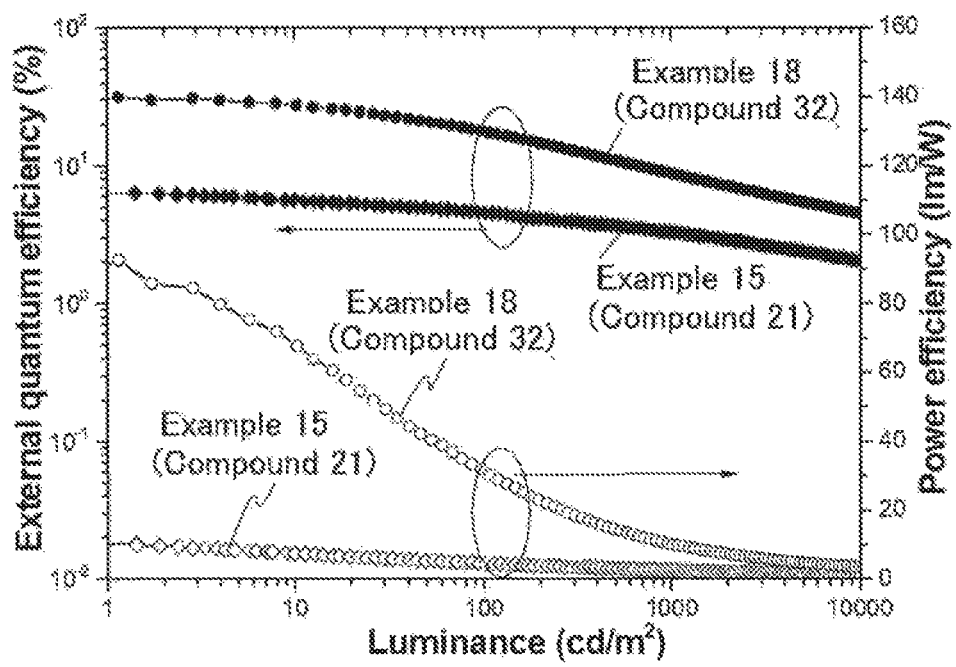
FIG. 56 is a graph showing the luminance-external quantum efficiency-electric power efficiency characteristics of the organic electroluminescent devices of the compound 21 in Example 15 and the compound 32 in Example 18.

FIG. 55 shows the voltage-current density-luminance characteristics thereof, FIG. 56 shows luminance-external quantum efficiency-electric power efficiency characteristics thereof, and the device characteristics thus measured are shown in Table 2. The organic electroluminescent device using the compound 21 as a light-emitting material achieved an external quantum efficiency of 6.3%.

Example 16

Production and Evaluation of Organic Electroluminescent Device Using Compound 30

An organic electroluminescent device was produced in the same manner as in Example 13 except that the compound 30 was used instead of the compound 19 in the formation of the light-emitting layer.

Figure 57:
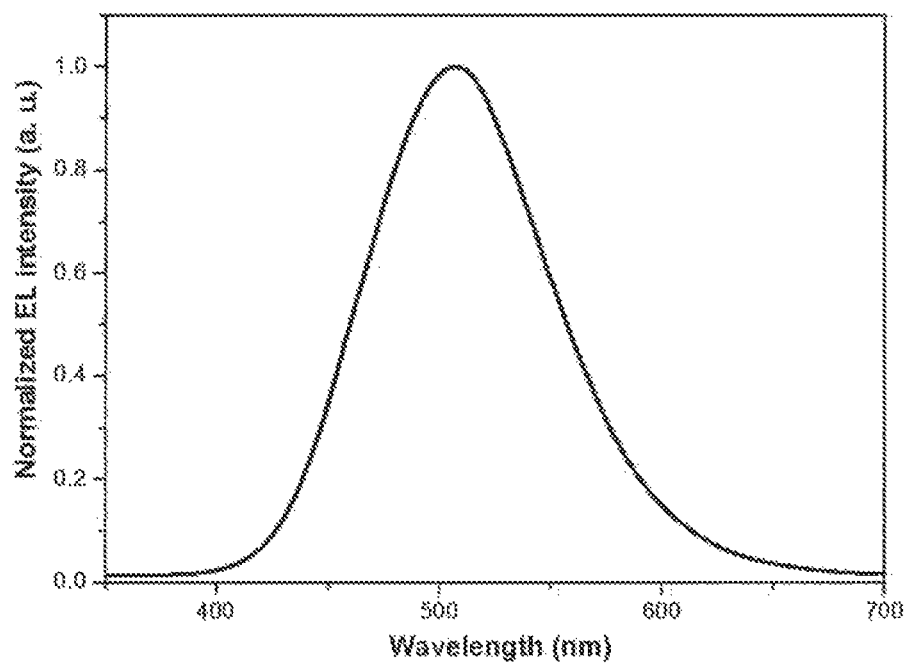
FIG. 57 shows the light emission spectrum of the organic electroluminescent device of the compound 30 in Example 16.
Figure 58:
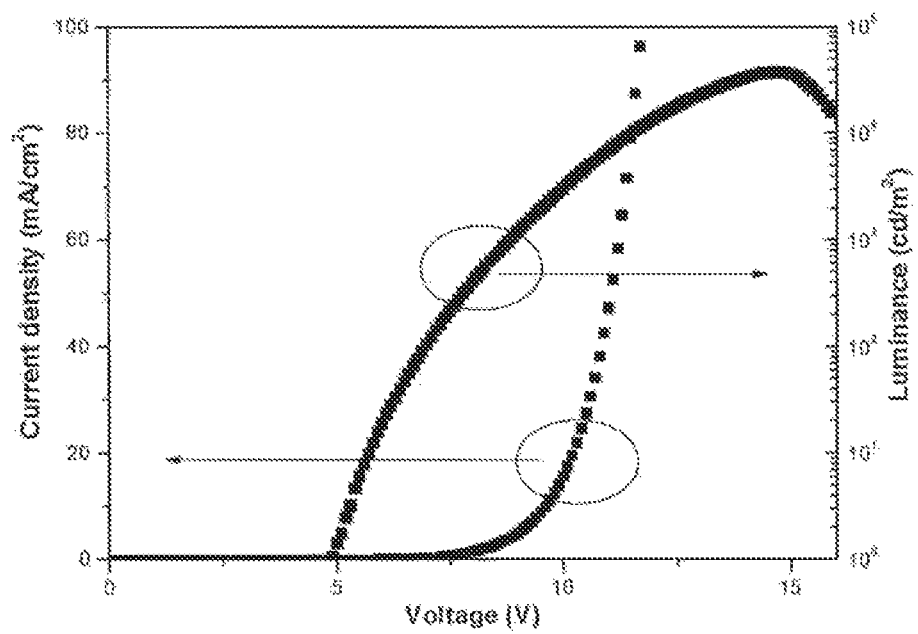
FIG. 58 is a graph showing the voltage-current density-luminance characteristics of the organic electroluminescent device of the compound 30 in Example 16.
Figure 59:
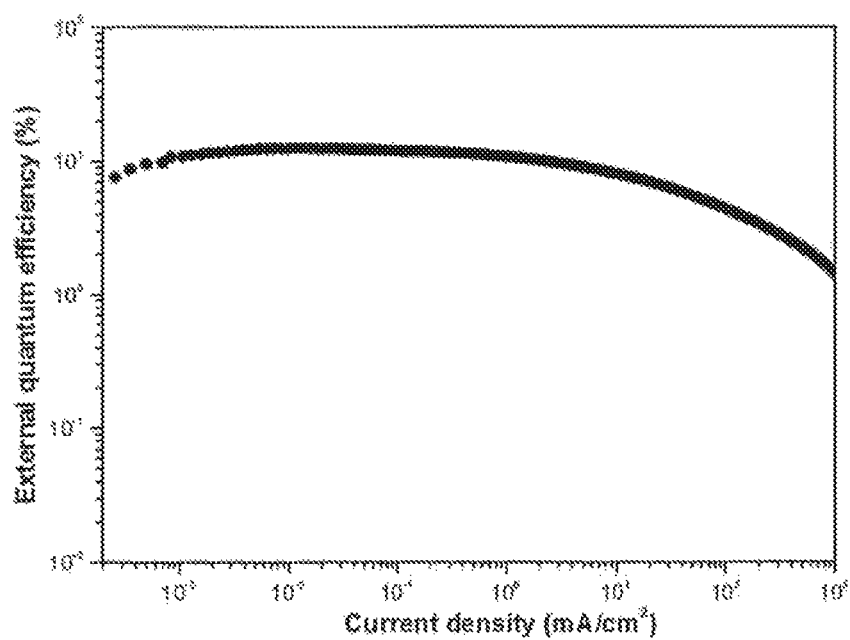
FIG. 59 is a graph showing the current density-external quantum efficiency characteristics of the organic electroluminescent device of the compound 30 in Example 16.

FIG. 57 shows the light emission spectrum at 10 mA/cm$^2$ of the organic electroluminescent device thus produced, FIG. 58 shows the voltage-current density-luminance characteristics thereof, and FIG. 59 shows current density-external quantum efficiency characteristics thereof. The organic electroluminescent device using the compound 30 as a light-emitting material achieved a high external quantum efficiency of 12.51%.

Example 17

Production and Evaluation of Organic Electroluminescent Device Using Compound 31

An organic electroluminescent device was produced in the same manner as in Example 13 except that the compound 31 was used instead of the compound 19 in the formation of the light-emitting layer.

Figure 60:
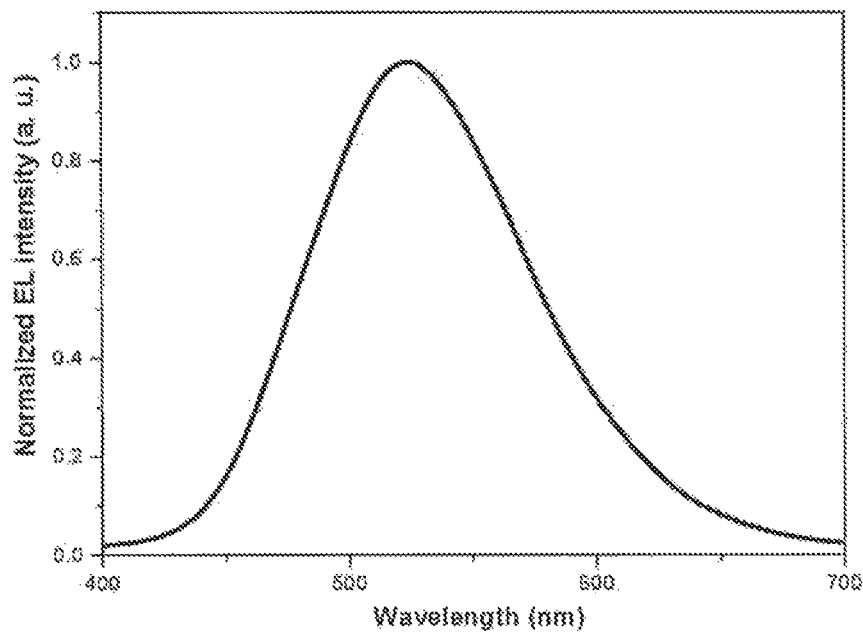
FIG. 60 shows the light emission spectrum of the organic electroluminescent device of the compound 31 in Example 17.
Figure 61:
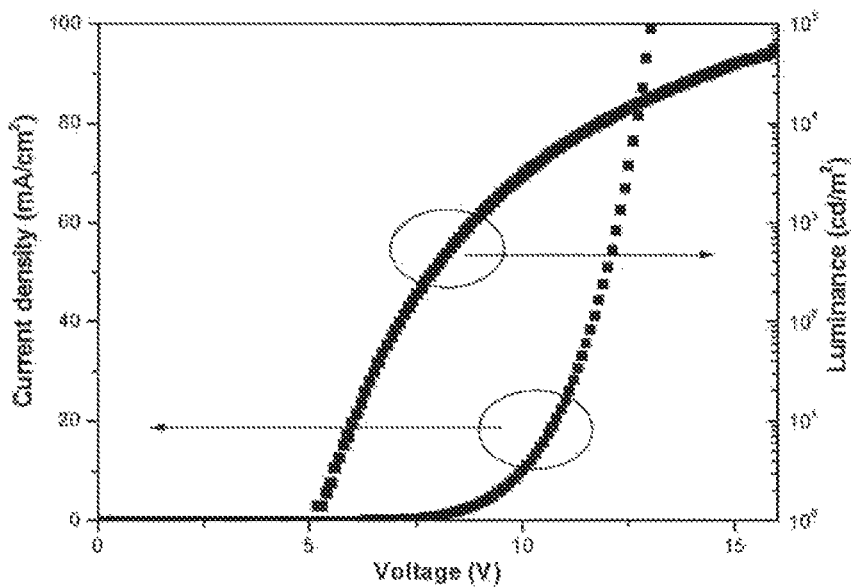
FIG. 61 is a graph showing the voltage-current density-luminance characteristics of the organic electroluminescent device of the compound 31 in Example 17.
Figure 62:
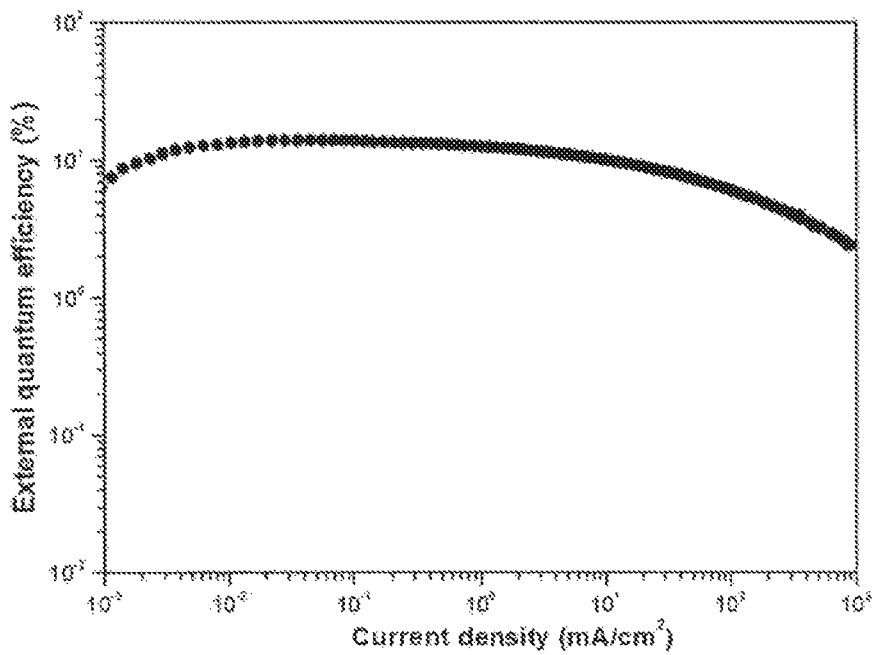
FIG. 62 is a graph showing the current density-external quantum efficiency characteristics of the organic electroluminescent device of the compound 31 in Example 17.

FIG. 60 shows the light emission spectrum at 10 mA/cm$^2$ of the organic electroluminescent device thus produced, FIG. 61 shows the voltage-current density-luminance characteristics thereof, and FIG. 62 shows current density-external quantum efficiency characteristics thereof. The organic electroluminescent device using the compound 31 as a light-emitting material achieved a high external quantum efficiency of 14.04%.

Example 18

Production and Evaluation of Organic Electroluminescent Device Using Compound 32

An organic electroluminescent device was produced in the same manner as in Example 15 except that the light-emitting layer was formed by using the compound 32 instead of the compound 21.

FIG. 55 shows the voltage-current density-luminance characteristics thereof, FIG. 56 shows luminance-external quantum efficiency-electric power efficiency characteristics thereof, and the device characteristics thus measured are shown in Table 2. The organic electroluminescent device using the compound 32 as a light-emitting material achieved a high external quantum efficiency of 30.6%. The measurement of the transient decay curve for the compound 32 revealed that the compound was a thermal activation type delayed fluorescent material.

Example 19

Production and Evaluation of Organic Electroluminescent Device Using Compound 32

An organic electroluminescent device was produced in the same manner as in Example 13 except that the compound 32 was used instead of the compound 19, and PPF was used instead of mCBP, in the formation of the light-emitting layer.

Figure 63:
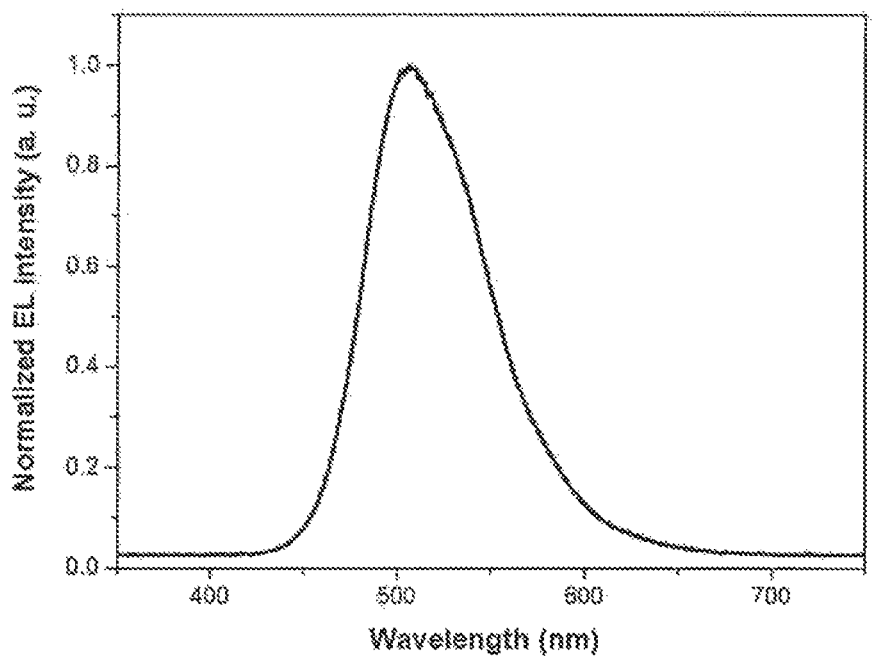
FIG. 63 shows the light emission spectrum of the organic electroluminescent device of the compound 32 in Example 19.
Figure 64:
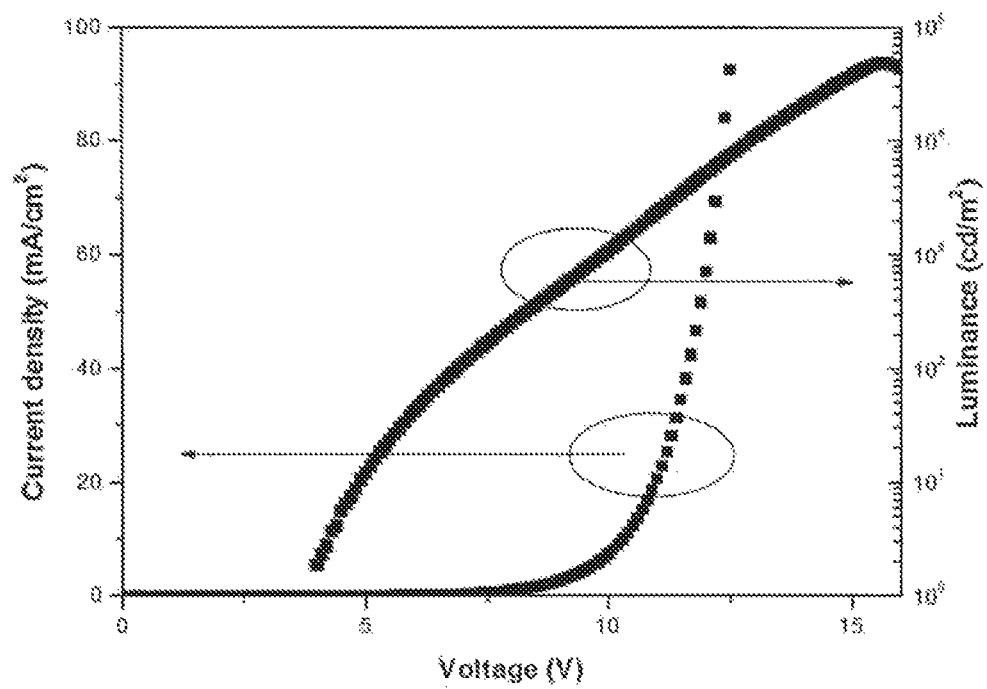
FIG. 64 is a graph showing the voltage-current density-luminance characteristics of the organic electroluminescent device of the compound 32 in Example 19.
Figure 65:
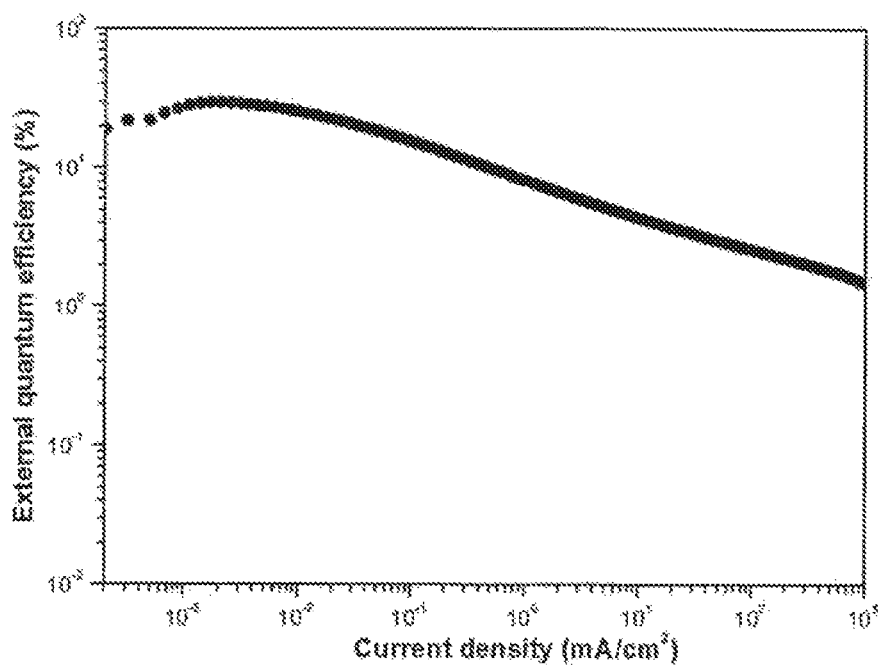
FIG. 65 is a graph showing the current density-external quantum efficiency characteristics of the organic electroluminescent device of the compound 32 in Example 19.

FIG. 63 shows the light emission spectrum at 10 mA/cm$^2$ of the organic electroluminescent device thus produced, FIG. 64 shows the voltage-current density-luminance characteristics thereof, and FIG. 65 shows current density-external quantum efficiency characteristics thereof. The organic electroluminescent device using the compound 32 as a light-emitting material achieved a high external quantum efficiency of 29.64%.

TABLE 1

|  | On voltage $V_{on}$ (V) | Maximum luminance $L_{max}$ (cd/m$^2$) | External quantum efficiency EQE (%) |
|---|---|---|---|
| Example 10 | 4.0 | 17,400 | 21.3 |
| Example 12 | 3.8 | 38,000 | 23.1 |

TABLE 2
| | Light emission wavelength $\lambda_{EL}$ (nm) | On voltage $V_{on}$ (V) | Maximum luminance $L_{max}$ (cd/m²) | External quantum efficiency EQE (%) | Maximum electric power efficiency Max PE (lm/W) |
|---|---|---|---|---|---|
| Example 15 | 511 | 5.3 | 41,800 | 6.3 | 10.1 |
| Example 18 | 505 | 3.1 | 82,200 | 30.6 | 92.6 |
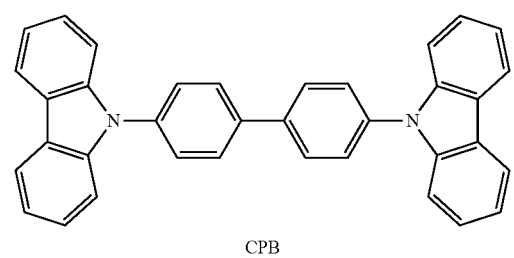
CPB
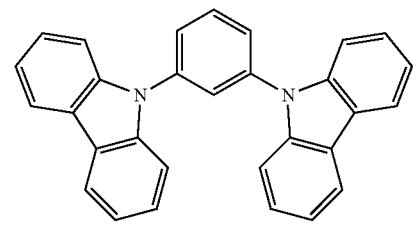
mCP
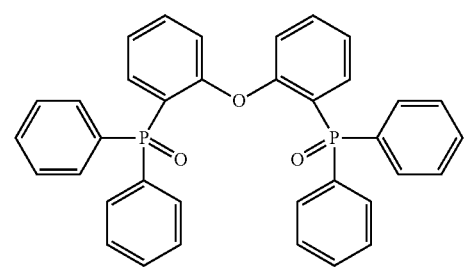
DPEPO
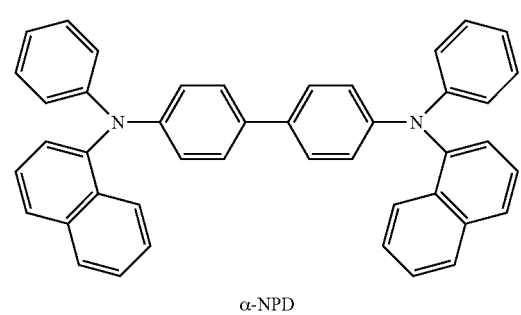
α-NPD
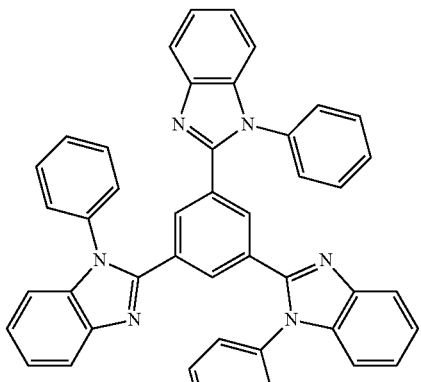
TPBi
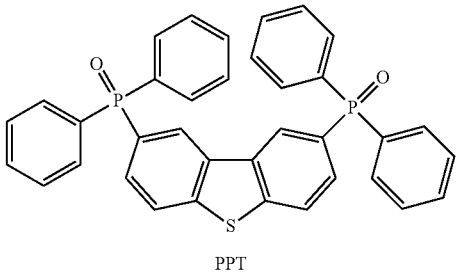
PPT
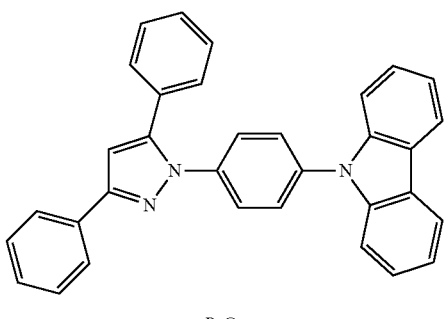
PzCz
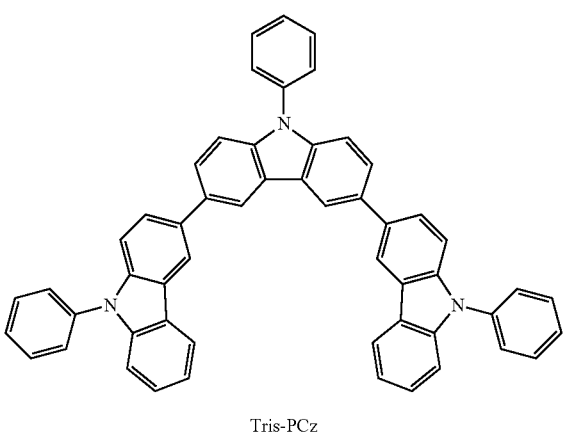
Tris-PCz

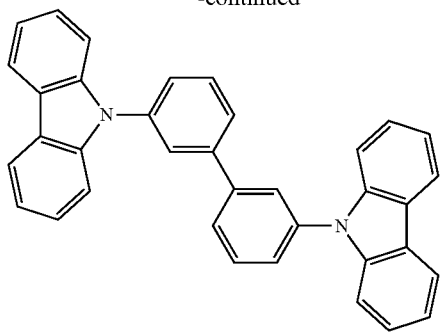

mCBP

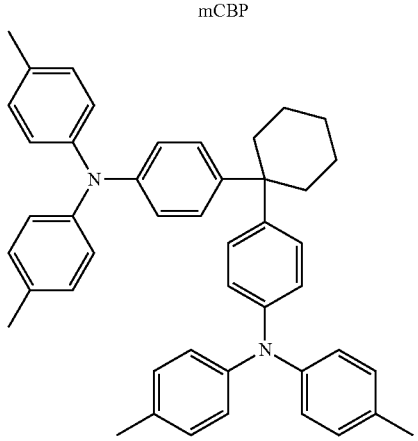

TAPC

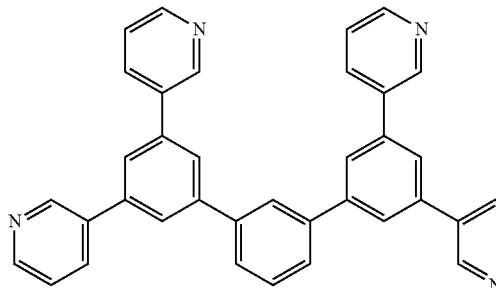

BmPyPbB

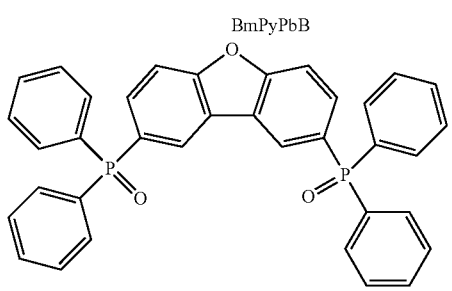

PPF

INDUSTRIAL APPLICABILITY

The compound of the invention is useful as a light-emitting material. Accordingly, the compound of the invention may be effectively used as a light-emitting material of an organic light-emitting device, such as an organic electroluminescent device. The compound of the invention includes a compound that emits delayed fluorescent light, and thus may be capable of providing an organic light-emitting device having a high light emission efficiency. Thus, the invention has high industrial applicability.

REFERENCE SIGNS LIST 1 substrate
2 anode
3 hole injection layer
4 hole transporting layer
5 light-emitting layer 5
6 electron transporting layer
7 cathode

The invention claimed is:

1. A light-emitting material containing a compound represented by the following general formula (1):

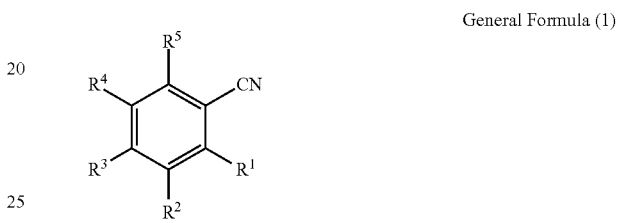

General Formula (1)

wherein in the general formula (1), from 0 to 1 of $R^1$ to $R^5$ represents a cyano group, from 2 to 5 of $R^1$ to $R^5$ each represent a group represented by the following general formula (2) or the following general formula (7), and the balance of $R^1$ to $R^5$ each represent a hydrogen atom or a substituent other than above, provided that when $R^1$ is a group represented by the following general formula (2), then $R^5$ is a hydrogen atom or a cyano group and that when $R^{15}$ and $R^{16}$ in the following general formula (2) are bonded to each other to form a single bond, one of $R^1$ to $R^5$ is a cyano group:

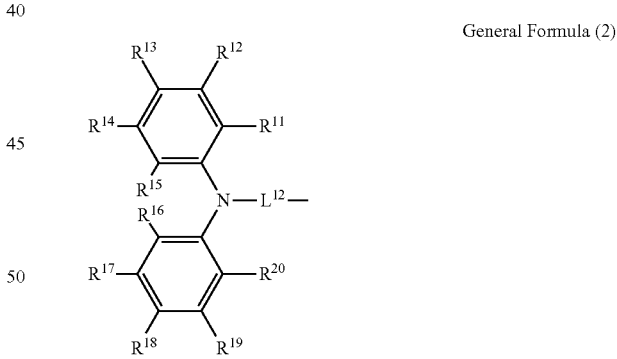

General Formula (2)

wherein in the general formula (2), $R^{11}$ to $R^{20}$ each independently represent a hydrogen atom or a substituent, provided that $R^{11}$ and $R^{12}$, $R^{12}$ and $R^{13}$, $R^{13}$ and $R^{14}$, $R^{14}$ and $R^{15}$, $R^{15}$ and $R^{16}$, $R^{16}$ and $R^{17}$, $R^{17}$ and $R^{18}$, $R^{18}$ and $R^{19}$, and $R^{19}$ and $R^{20}$ each may be bonded to each other to form a cyclic structure; and $L^{12}$ represents a substituted or unsubstituted arylene group or a substituted or unsubstituted heteroarylene group, provided that when $R^{15}$ and $R^{16}$ are not taken together to form a cyclic structure or $R^{15}$ and $R^{16}$ are taken together with an oxy group (—O—) to form a cyclic structure, then $L^{12}$ is a monocyclic arylene or monocyclic heteroarylene group, General Formula (7)

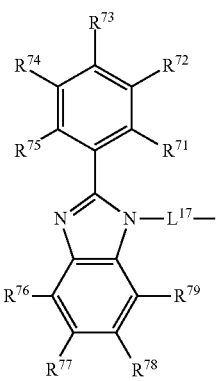

wherein in the general formula (7), $R^{71}$ to $R^{79}$ each independently represent a hydrogen atom or a substituent, provided that $R^{71}$ and $R^{72}$, $R^{72}$ and $R^{73}$, $R^{73}$ and $R^{74}$, $R^{74}$ and $R^{75}$, $R^{76}$ and $R^{77}$, $R^{77}$ and $R^{78}$, $R^{78}$ and $R^{79}$ each may be bonded to each other to form a cyclic structure; and $L^{17}$ represents a substituted or unsubstituted arylene group or a substituted or unsubstituted heteroarylene group.

2. The light-emitting material according to claim 1, wherein the group represented by the general formula (2) is a group represented by any one of the following general formulae (3) to (6) and (8):

General Formula (3)

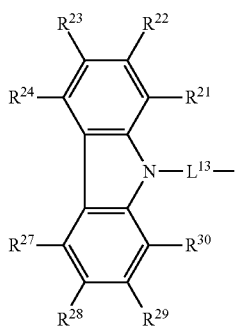

General Formula (4)

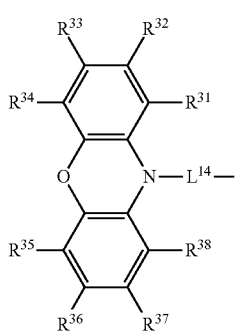

General Formula (5)

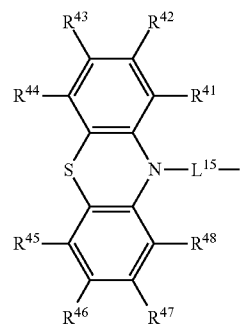

General Formula (6)

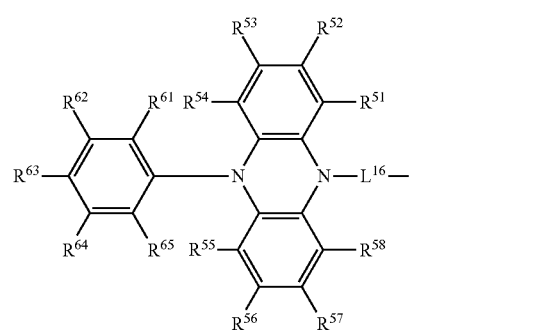

General Formula (8)

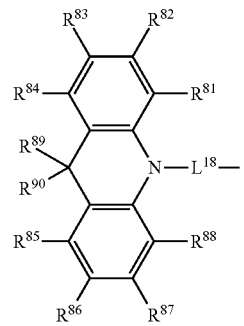

wherein in the general formulae (3) to (6) and (8), $R^{21}$ to $R^{24}$, $R^{27}$ to $R^{38}$, $R^{41}$ to $R^{48}$, $R^{51}$ to $R^{58}$, $R^{61}$ to $R^{65}$, and $R^{81}$ to $R^{90}$ each independently represent a hydrogen atom or a substituent, provided that $R^{21}$ and $R^{22}$, $R^{22}$ and $R^{23}$, $R^{23}$ and $R^{24}$, $R^{27}$ and $R^{28}$, $R^{28}$ and $R^{29}$, $R^{29}$ and $R^{30}$, $R^{31}$ and $R^{32}$, $R^{32}$ and $R^{33}$, $R^{33}$ and $R^{34}$, $R^{35}$ and $R^{36}$, $R^{36}$ and $R^{37}$, $R^{37}$ and $R^{38}$, $R^{41}$ and $R^{42}$, $R^{42}$ and $R^{43}$, $R^{43}$ and $R^{44}$, $R^{45}$ and $R^{46}$, $R^{46}$ and $R^{47}$, $R^{47}$ and $R^{48}$, $R^{51}$ and $R^{52}$, $R^{52}$ and $R^{53}$, $R^{53}$ and $R^{54}$, $R^{55}$ and $R^{56}$, $R^{56}$ and $R^{57}$, $R^{57}$ and $R^{58}$, $R^{61}$ and $R^{62}$, $R^{62}$ and $R^{63}$, $R^{63}$ and $R^{64}$, $R^{64}$ and $R^{65}$, $R^{54}$ and $R^{61}$, $R^{55}$ and $R^{65}$, $R^{81}$ and $R^{82}$, $R^{82}$ and $R^{83}$, $R^{83}$ and $R^{84}$, $R^{85}$ and $R^{86}$, $R^{86}$ and $R^{87}$, $R^{87}$ and $R^{88}$, and $R^{89}$ and $R^{90}$ each may be bonded to each other to form a cyclic structure; and $L^{13}$ to $L^{16}$ and $L^{18}$ each independently represent a substituted or unsubstituted arylene group or a substituted or unsubstituted heteroarylene group.

3. The light-emitting material according to claim 1, wherein in the general formula (1), $R^3$ represents a cyano group.

4. The light-emitting material according to claim 1, wherein in the general formula (1), $R^1$ and $R^4$ each represent a group represented by the general formula (2).

5. The light-emitting material according to claim 1, wherein in the general formula (2), $L^{12}$ represents a phenylene group.

6. The light-emitting material according to claim 2, wherein the group represented by the general formula (2) is a group represented by the general formula (3).

7. The light-emitting material according to claim 6, wherein in the general formula (3), $L^{13}$ represents a 1,3-phenylene group.

8. The light-emitting material according to claim 2, wherein the group represented by the general formula (2) is a group represented by the general formula (4).

9. The light-emitting material according to claim 8, wherein in the general formula (4), $L^{14}$ represents a 1,4-phenylene group.

10. The light-emitting material according to claim 2, wherein the group represented by the general formula (2) is a group represented by the general formula (8).

11. The light-emitting material according to claim 10, wherein in the general formula (8), $L^{18}$ represents a 1,4-phenylene group.

12. The light-emitting material according to claim 2, wherein in the general formula (1), $R^1$ represents a group that satisfies the following condition A, and $R^2$ represents a substituted or unsubstituted aryl group; or in the general formula (1), $R^2$ represents a group that satisfies the following condition A, and at least one of $R^1$ and $R^3$ represents a substituted or unsubstituted aryl group; or in the general formula (1), $R^3$ represents a group that satisfies the following condition A, and at least one of $R^2$ and $R^4$ represents a substituted or unsubstituted aryl group:
condition A: a group represented by the general formula (2), provided that $R^{15}$ and $R^{16}$ are not bonded to each other, or a group represented by the general formula (3).

13. The light-emitting material according to claim 2, wherein in the general formula (1), $R^1$ represents a group represented by the general formula (4), (5), (6), or (8), and $R^2$ represents a hydrogen atom; or in the general formula (1), $R^2$ represents a group represented by the general formula (4), (5), (6), or (8), and at least one of $R^1$ and $R^3$ represents a hydrogen atom; or in the general formula (1), $R^3$ represents a group represented by the general formula (4), (5), (6), or (8), and at least one of $R^2$ and $R^4$ represents a hydrogen atom.

14. An organic light-emitting device containing the light-emitting material according to claim 1.

15. The organic light-emitting device according to claim 14, wherein the organic light-emitting device emits delayed fluorescent light.

16. The organic light-emitting device according to claim 14, wherein the organic light-emitting device is an organic electroluminescent device.

17. A compound represented by the following general formula (1'):

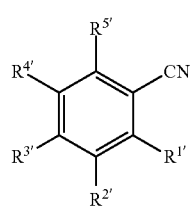

General Formula (1')

wherein in the general formula (1'), from 0 to 1 of $R^{1'}$ to $R^{5'}$ represents a cyano group, from 2 to 5 of $R^{1'}$ to $R^{5'}$ each represent a group represented by the following general formula (2') or the following general formula (7), and the balance of $R^{1'}$ to $R^{5'}$ each represent a hydrogen atom or a substituent other than above, provided that when $R^{1'}$ is a group represented by the following general formula (2), then $R^{5'}$ is a hydrogen atom or a cyano group:

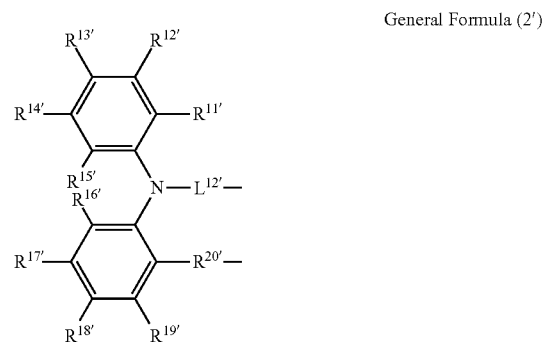

General Formula (2')

wherein in the general formula (2'), $R^{11'}$ to $R^{20'}$ each independently represent a hydrogen atom or a substituent, provided that $R^{11'}$ and $R^{12'}$, $R^{12'}$ and $R^{13'}$, $R^{13'}$ and $R^{14'}$, $R^{14'}$ and $R^{15'}$, $R^{15'}$ and $R^{16'}$, $R^{16'}$ and $R^{17'}$, $R^{17'}$ and $R^{18'}$, $R^{18'}$ and $R^{19'}$, and $R^{19'}$ and $R^{20'}$ each may be bonded to each other to form a cyclic structure; and $L^{12'}$ represents a substituted or unsubstituted arylene group or a substituted or unsubstituted heteroarylene group, provided that when $R^{15'}$ and $R^{16'}$ are not taken together to form a cyclic structure or $R^{15'}$ and $R^{16'}$ are taken together with an oxy group (—O—) to form a cyclic structure, then $L^{12'}$ is a monocyclic arylene or monocyclic heteroarylene group, and that when $R^{15'}$ and $R^{16'}$ in general formula (2') are bonded to each other to form a single bond, one of $R^{1'}$ to $R^{5'}$ is a cyano group;

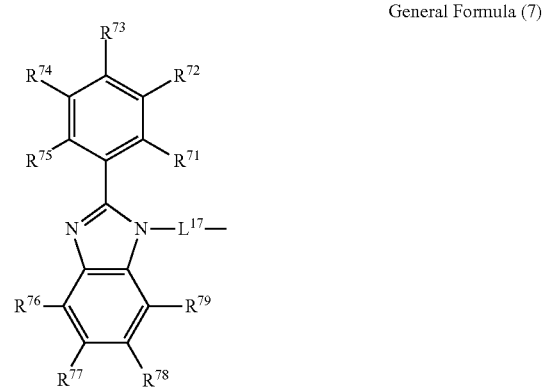

General Formula (7)

wherein in the general formula (7), $R^{71}$ to $R^{79}$ each independently represent a hydrogen atom or a substituent, provided that $R^{71}$ and $R^{72}$, $R^{72}$ and $R^{73}$, $R^{73}$ and $R^{74}$, $R^{74}$ and $R^{75}$, $R^{76}$ and $R^{77}$, $R^{77}$ and $R^{78}$, $R^{78}$ and $R^{79}$ each may be bonded to each other to form a cyclic structure; and $L^{17}$ represents a substituted or unsubstituted arylene group or a substituted or unsubstituted heteroarylene group.

18. The light-emitting material according to claim 1, wherein when $R^{15}$ and $R^{16}$ in the general formula (2) are not bonded to each other, one of $R^1$ to $R^5$ is a cyano group.

* * * * *